(12) United States Patent
Carl et al.

(10) Patent No.: US 8,486,078 B2
(45) Date of Patent: Jul. 16, 2013

(54) SYSTEMS, DEVICES AND APPARATUSES FOR BONY FIXATION AND DISK REPAIR AND REPLACEMENT METHODS RELATED THERETO

(75) Inventors: Allen Carl, Slingerlands, NY (US); Josef K. Winkler, Wayland, MA (US); Robert F. Beisel, Robesonia, PA (US); Spanky A. Raymond, Uniontown, OH (US); Daniel S. Savage, Brecksville, OH (US); Jason J. Gromek, Chesterland, OH (US); Carl M. Nilsson, Cleveland Heights, OH (US); Nathan J. Pierce, Millville, UT (US)

(73) Assignee: Highgate Orthopedics, Newton, MA (US)

( * ) Notice: Subject to any disclaimer, the term of this patent is extended or adjusted under 35 U.S.C. 154(b) by 559 days.

(21) Appl. No.: 12/087,912

(22) PCT Filed: Jan. 17, 2007

(86) PCT No.: PCT/US2007/001402
§ 371 (c)(1),
(2), (4) Date: Jun. 2, 2010

(87) PCT Pub. No.: WO2007/084649
PCT Pub. Date: Jul. 26, 2007

(65) Prior Publication Data
US 2010/0268237 A1    Oct. 21, 2010

Related U.S. Application Data

(63) Continuation-in-part of application No. 10/968,867, filed on Oct. 18, 2004, and a continuation-in-part of application No. 10/601,014, filed on Jun. 20, 2003, which is a continuation of application No. 09/536,732, filed on Mar. 28, 2000, now Pat. No. 6,607,530.

(60) Provisional application No. 60/759,718, filed on Jan. 17, 2006, provisional application No. 60/133,356, filed on May 10, 1999, provisional application No. 60/512,134, filed on Oct. 17, 2003.

(51) Int. Cl.
*A61B 17/56* (2006.01)

(52) U.S. Cl.
USPC .......................................................... 606/87

(58) Field of Classification Search
USPC ... 606/79–85, 86 R, 87–89; 623/17.11–17.16
See application file for complete search history.

(56) References Cited

U.S. PATENT DOCUMENTS

| 3,426,364 A | 2/1969 | Lumb |
| 4,059,115 A | 11/1977 | Jumashev et al. |

(Continued)

FOREIGN PATENT DOCUMENTS

| WO | WO-9111962 A1 | 8/1991 |
| WO | WO-0067651 A1 | 11/2000 |
| WO | WO-2005037082 A2 | 4/2005 |

OTHER PUBLICATIONS

Supplemental European Search Report and written opinion for corresponding European application No. EP06849057.2, issued Jul. 2, 2012.

(Continued)

*Primary Examiner* — Kevin T Truong
*Assistant Examiner* — Christopher Beccia
(74) *Attorney, Agent, or Firm* — Edwards Wildman Palmer LLP; Brian S. Matross; Joshua L. Jones

(57) ABSTRACT

The present invention features new methods, apparatuses and devices for fixing adjacent bone segments, segments of a bony structure and adjacent vertebrate of a spine. The methods, apparatuses and devices utilize an apparatus for forming a channel in a surface of the bone or bony structure segments or adjacent vertebra or a channel submerged within the bone or bony structure segments or adjacent vertebra. In more particular embodiments such apparatuses and methods including forming an arcuate channel and which channel can receive therein a curved rod or implant member. Also featured are systems, apparatuses and methods for removably suspending a spacer in the intervertebral space while forming such a channel as well as systems, apparatuses and methods for use of dynamized implant members.

26 Claims, 69 Drawing Sheets

U.S. PATENT DOCUMENTS

| | | | |
|---|---|---|---|
| 4,135,506 A | 1/1979 | Ulrich | |
| 4,335,715 A | 6/1982 | Kirkley | |
| 4,773,402 A | 9/1988 | Asher et al. | |
| 4,790,303 A | 12/1988 | Steffee | |
| 4,834,757 A | 5/1989 | Brantigan | |
| 4,907,577 A | 3/1990 | Wu | |
| 4,941,466 A | 7/1990 | Romano | |
| 5,352,224 A | 10/1994 | Westermann | |
| 5,355,588 A | 10/1994 | Brandenburg, Jr. et al. | |
| 5,415,661 A | 5/1995 | Holmes | |
| 5,423,826 A | 6/1995 | Coates et al. | |
| 5,425,772 A | 6/1995 | Brantigan | |
| 5,445,639 A | 8/1995 | Kuslich et al. | |
| 5,509,918 A | 4/1996 | Romano | |
| 5,527,316 A | 6/1996 | Stone et al. | |
| 5,545,164 A | 8/1996 | Howland | |
| 5,591,165 A | 1/1997 | Jackson | |
| 5,591,235 A | 1/1997 | Kuslich | |
| 5,700,265 A | 12/1997 | Romano | |
| 5,765,289 A | 6/1998 | Schulz et al. | |
| D401,335 S | 11/1998 | Koros et al. | |
| 5,895,183 A | 4/1999 | McDaniel et al. | |
| 5,899,908 A | 5/1999 | Kuslich et al. | |
| 5,928,267 A | 7/1999 | Bonutti et al. | |
| 5,974,674 A | 11/1999 | Kelly | |
| 6,056,749 A | 5/2000 | Kuslich | |
| 6,241,769 B1 | 6/2001 | Nicholson et al. | |
| RE37,479 E | 12/2001 | Kulich | |
| 6,342,056 B1 | 1/2002 | Mac-Thiong et al. | |
| 6,425,919 B1 | 7/2002 | Lambrecht | |
| 6,558,390 B2 | 5/2003 | Cragg | |
| 6,575,979 B1 | 6/2003 | Cragg | |
| 6,592,559 B1 | 7/2003 | Pakter et al. | |
| 6,607,530 B1 * | 8/2003 | Carl et al. | 606/914 |
| 6,805,697 B1 | 10/2004 | Helm et al. | |
| 6,923,811 B1 | 8/2005 | Carl et al. | |
| 2002/0090999 A1 | 7/2002 | Romano | |
| 2003/0220641 A1 | 11/2003 | Thelen et al. | |
| 2004/0039384 A1 | 2/2004 | Boehm et al. | |
| 2004/0059333 A1 | 3/2004 | Carl et al. | |
| 2004/0092933 A1 | 5/2004 | Shaolian et al. | |
| 2004/0092993 A1 * | 5/2004 | Teitelbaum et al. | 606/180 |
| 2004/0158325 A1 * | 8/2004 | Errico et al. | 623/17.11 |
| 2005/0177168 A1 | 8/2005 | Brunnett et al. | |
| 2005/0203624 A1 * | 9/2005 | Serhan et al. | 623/17.11 |
| 2005/0267481 A1 * | 12/2005 | Carl et al. | 606/79 |
| 2007/0167951 A1 * | 7/2007 | Ainsworth et al. | 606/90 |
| 2009/0187191 A1 * | 7/2009 | Carl et al. | 606/80 |

OTHER PUBLICATIONS

Supplemental European Search Report and written opinion for related European application No. EP07716784.9, issued dated Apr. 19, 2012.

International Search Report and International Preliminary Report on Patentability for International Application No. PCT/US 07/01402, dated Oct. 18, 2007 and corresponding to related European application No. EP07716784.9.

International Search Report and International Preliminary Report on Patentability for International Application No. PCT/US 06/49619, dated Oct. 17, 2007 and corresponding to related European application No. EP06849057.2.

* cited by examiner

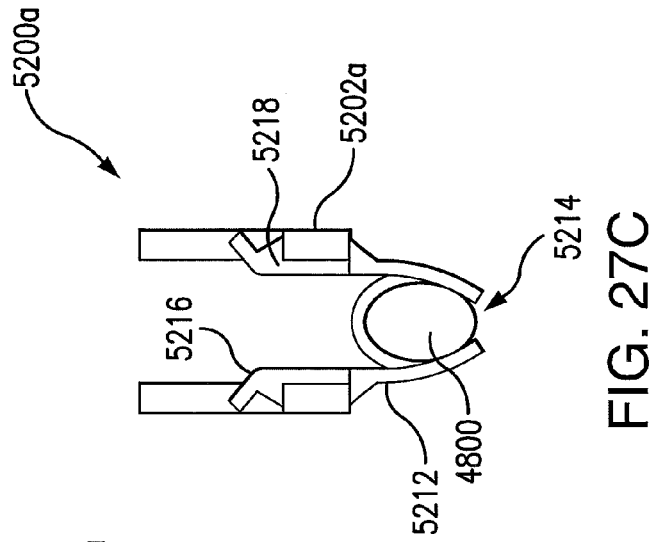
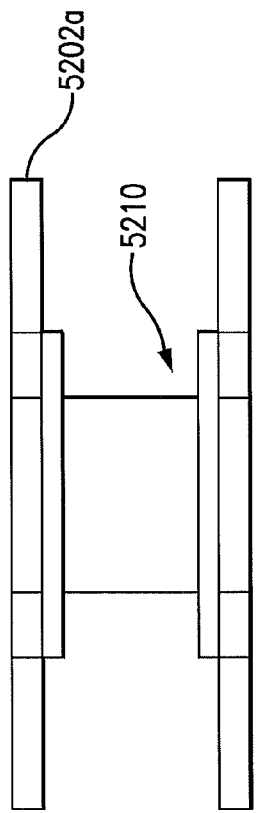
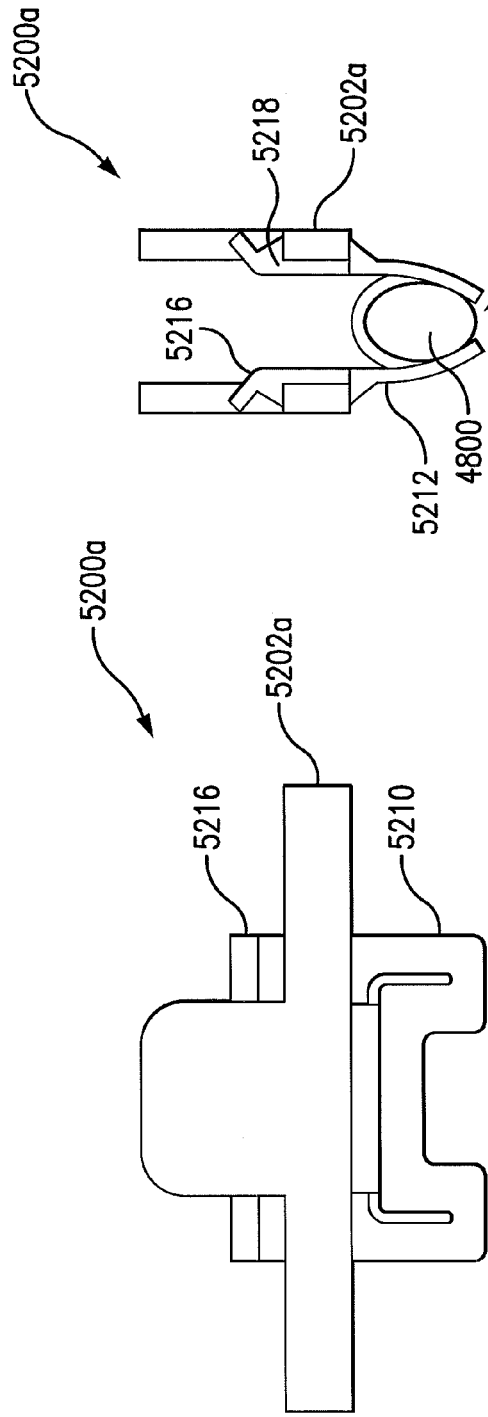

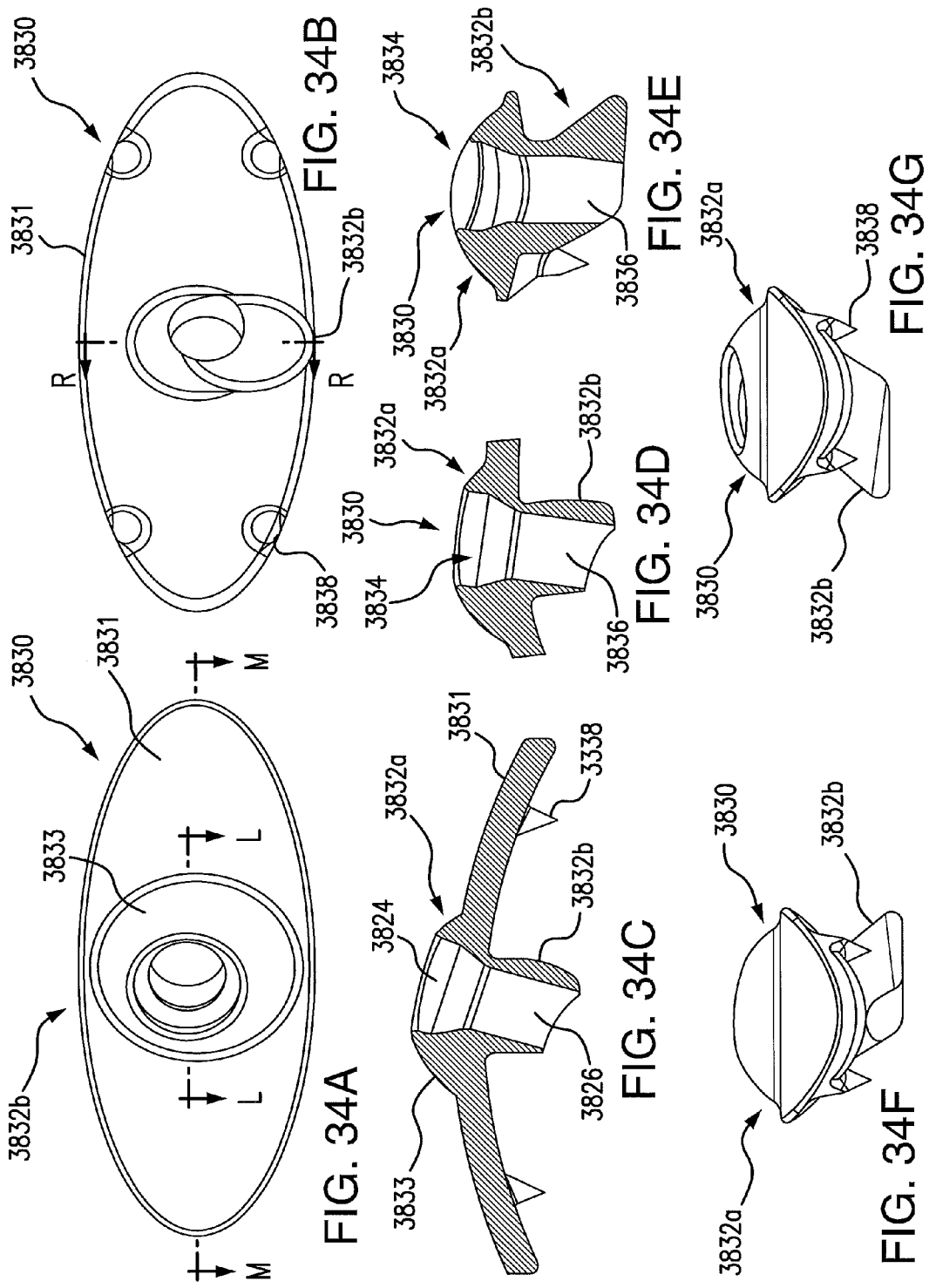

SYSTEMS, DEVICES AND APPARATUSES FOR BONY FIXATION AND DISK REPAIR AND REPLACEMENT METHODS RELATED THERETO

This application is a National Stage Filing of PCT Application No. PST/US2007/001402, filed Jan. 17, 2007, which application claims the benefit of U.S. Provisional Application Ser. No. 60/759,718 filed Jan. 17, 2006. This application also is a continuation-in-part of U.S. application Ser. No. 10/968,867 filed Oct. 18, 2004, which claims the benefit of U.S. Provisional Application Ser. No. 60/512,134 filed Oct. 17, 2003. This application also is a continuation-in-part of U.S. application Ser. No. 10/601,014 filed Jun. 20, 2003, which application is a continuation of U.S. application Ser. No. 09/536,732 filed Mar. 28, 2000 (now U.S. Pat. No. 6,607,530), which application claims the benefit of U.S. Provisional Application Ser. No. 60/133,356 filed May 10, 1999. The teachings of all of the foregoing are incorporated herein by reference.

FIELD OF INVENTION

The present invention generally relates to methods, systems and apparatuses for bony fixation and more particularly to methods, systems and apparatuses adapted for fixing the bones of the spine. The present invention also generally relates to methods, systems and devices for augmenting, repairing or replacing the nucleus and/or annulus of an intervertebral disk of a spine, such as the spine of a mammalian body.

BACKGROUND OF THE INVENTION

Fixation or fusion of vertebral columns with bone or material, rods or plates is a common, long practiced surgical method for treating a variety of conditions. Many of the existing procedures involve the use of components that protrude outwardly, which may contact and damage a body part, such as the aorta, the vena cava, the sympathetic nerves, the lungs, the esophagus, the intestine and the ureter. Also, many constructions involve components that may loosen and cause undesirable problems, often-necessitating further surgical intervention. Additionally, limiting the success of these procedures are the biomechanical features of the spine itself, whose structure must simultaneously provide support to regions of the body, protect the vertebral nervous system and permit motion in multiple planes.

As indicated above, spinal surgery for spine fusion generally involves using implants and instrumentation to provide support to the affected area of the spine while allowing the bones thereof to fuse. The technology initially evolved using bone chips around and on top of an area of the spine that had been roughened to simulate a fracture in its consistency. The area, having encountered the bone chips, would then proceed to heal like a fracture, incorporating the bone chips. However, surgical procedures dealing with the spine present notable challenges. For example, bioengineers have been required to identify the various elements of the complex motions that the spine performs, and the components of the complex forces it bears. This complexity has made it difficult to achieve adequate stability and effective healing in surgical procedures directed to the spine.

One surgical technique provided by Cloward, involves cutting a dowel type hole with a saw across or through the moveable intervertebral disc and replacing it with a bone graft that was harvested from the hip bone. This procedure results in a fusion of the adjacent vertebral bodies and limits motion and mobility. However, as a result of the complex motions of the spine, it is often difficult to secure the dowel from displacing. Further, it has become apparent over time, however, that this particular technique does not always yield a secure fusion.

Other techniques have been developed that involve the placement of various hardware elements, including rods and hooks, rods and screws and plates and screws. The dowel technique also has advanced over the past five years or so, with dowels being fabricated from cadaver bone or metals such as titanium or stainless steel. These techniques, whether using hardware, dowels or some combination thereof, have a common goal to enhance stability by diminishing movement, thereby resulting in or enhancing the potential of a fusion of adjacent vertebral bones. For example, in one of these other techniques, the disc is removed and adjacent vertebrae are positioned in a stable position by placing a plate against and traversing them, which plate is secured or anchored to each by means of screws.

In another procedure, cages in the form of two parallel circular or rectangular devices are made out of a material such as titanium or stainless steel and these devices are fenestrated. Bone is packed in the center of the devices that will heal to adjacent bone through each fenestration. In this procedure, the disc space is distracted so all ligamentous structures are taut and the bones are held in their normal maximal position of distraction. Because the cages are implanted in spongy bone, they are more likely to collapse the surrounding bone, thus resulting in loss of distraction and subsequently cage dislodgment.

U.S. Pat. No. 5,591,235 reports a certain spinal fixation device and technique for stabilizing vertebrae. In this technique, a hollow screw is inserted into a hole, preferably a hole saw recess, in each adjoining vertebrae. A channel is cut into the vertebrae, which is lined up with corresponding axial slots in the screw. A rod is inserted into the channel and so as to pass through the axial slots in the screw. The rod is secured to each of the screws by means of a locking cap. The rod also is arranged so as to provide a bridge between the hollow screws in the adjoining vertebrae. Certain disadvantages have been surmised using such a device and technique. For example, it has become apparent that the trough in the vertebral bodies destabilizes some of the cortex of the vertebrae body wall, which is the strongest component.

In addition to fixation or fusion of vertebral columns, the prior art also describes methods or other spinal repair procedures, such as discectomy wherein an artificial disc or prosthetic device is placed within the vertebrae of the spine. For such prior art methods and related devices, there have been short comings such as having difficulty in securing the prostheses within the vertebral space or resulting in significant modification or damage to the load bearing surfaces of the vertebrae in an effort to secure the prosthesis.

Another method or other spinal repair technique involves augmentation of the nucleus of an intervertebral disk of the spine. The intervertebral disk is a flexible cartilaginous structure that is disposed between adjacent vertebrae. These disks form joints between the bodies of the vertebrae, which serve to unite adjacent vertebrae and to permit movement between them. These disks also play a role as shock absorbers when force is transmitted along the vertebral column during standing and movement.

Each disk is formed of two parts, a central mass called the nucleus pulpsous (herein the nucleus) and a surrounding fibrous layer, the annulus fibrosus (herein the annulus). The nucleus has a semi-gelatinous consistency, which allows it to become deformed when pressure is placed upon it, enabling the disk to change shape as the vertebral column moves.

There is described in U.S. Pat. Nos. 5,047,055; 5,824,093, 6,264,695; the teachings of which are incorporated herein by references, various techniques and/or prosthetics for use in replacing or augmenting a spinal disc nucleus. Given the structure of the disk and its location between adjacent vertebrae, it is not a simple task to access the nucleus for the insertion of such prosthetics or materials to augment the nucleus. One technique for accessing the nucleus contemplates using the defect in the annulus, however, in practice the defect usually needs to be enlarged to allow the insertion of the prosthetic. Another technique contemplates having the surgeon drill through one of the adjacent bodies using a lateral approach. This another technique relies heavily on the skill and dexterity of the surgeon not to damage surrounding tissues, nerves and blood vessels. Also, the holed formed by such drilling is not easily sealed because of its shape and configuration.

Conventional techniques relating to fixation of the spine and bony structure rely in great part on the skill and dexterity of the surgeon to control the devices and instrumentalities being used to protect surrounding tissues, muscles, nerves and blood vessels from damage during the procedure. This is so because the devices and/or instrumentalities that the surgeon uses during such techniques, themselves do not provided the surgeon with a mechanism to protect the tissues, muscles, nerves and blood vessels surrounding the treatment or target area within the body from coming into contact with the device or instrumentality during the procedure. Consequently, the surgeon must use surgical techniques to relocate tissues, muscles, nerves and blood vessels from the surgical field, if that is possible, and for those which it is not possible, the surgeon must take care in the use of the device or instrumentality to prevent injury. It should be recognized that the surgeon while inserting and retracting or removing the device or instrumentality from the bony structure or spine must exercise such care to prevent injury.

Thus, it would be desirable to provide a new apparatus, system and methods for bony fixation that enhances healing of the bone while providing structural support therefore. It would be particularly desirable to provide such an apparatus, system and method that would involve the use of open surgical or minimally invasive surgical techniques as well as a technique in which the implant burrows in the structure of the bone; more particularly a technique in which the implant burrows in the bone spine, traverses across the disk space, and ends in an adjacent or neighboring vertebrae or vertebras, providing limited or no protrusions. It also would be desirable to provide such an apparatus, system and method where the implant is retained within the bone without requiring external fixation including contour-varying external vertebral wall fixation as compared to conventional devices, as such a device would avoid many of the problems associated with conventional devices such as blood vessel injury, erosion into organs, as well as placement near nerves. It also would be desirable for such apparatuses and systems to be adaptable for use in a wide range of procedures and techniques, including but not limited to augmentation of the nucleus such as by use of prosthetics.

SUMMARY OF THE INVENTION

The present invention features new methods, apparatuses and devices for fixing adjacent bone segments, segments of a bony structure and adjacent vertebrate of a spine. The methods, apparatuses and devices utilize a new apparatus for forming a channel in a surface of the bone or bony structure segments or adjacent vertebra or a channel submerged within the bone or bony structure segments or adjacent vertebra. In more particular embodiments such apparatuses and methods include forming an arcuate channel. Also the channel formed can receive therein a curved rod or implant member, which also preferably is arcuate, and avoids the associated problems with prior cage or straight rod and screw systems. Also featured are devices used in connection with such apparatuses and methods.

According to an aspect of the present invention there is featured a method for forming a channel, an arcuate channel in adjacent bone segments, adjacent segments of a bony structure or adjacent vertebra of a spine, the bone segments, bony structure and spine more particularly being those of a mammalian body (e.g., human body). Such a method includes positioning a frame assembly proximal the treatment or surgical site, securing the frame assembly to the adjacent segments of the bone or bony structure or adjacent vertebra and rotating a drill bit in fixed relation to the frame assembly to form the channel in the surface or sub-surface of the bone, bony structure or vertebra. In further embodiments, the method further includes mechanically engaging a securing mechanism to the frame assembly so that the frame is maintained in fixed relation by such mechanical engagement alone or in combination with the lateral stiffness of the securing mechanism.

In more specific embodiments, the frame assembly includes a frame having a plurality of through apertures, each through aperture including a constricted portion and a plurality of securing members. Each of the plurality of securing members are driven through the through apertures and the constricted portion and into the bone, bony structure or vertebra at the site such that the frame is secured in fixed relation to the bone, bony segments or vertebra by the engagement of the constricted portion with the securing member and by the lateral stiffness of the securing members.

In further embodiments, the method further includes attaching a drill assembly to the frame assembly so a drill bit of the drill assembly follows a predetermined path, more particular a predetermined circular path, in fixed relation with respect to the frame and moving the drill bit through the predetermined path while the drill bit is rotating so as to cut the channel. In more particular embodiments, the method further includes providing a pivot arm assembly having a pivot arm that rotates in fixed relation to the frame, securing a portion of the drill assembly including the drill bit to the pivot arm assembly and rotating the drill bit using the pivot arm assembly so the drill bit traverses the predetermined path, more specifically the predetermined circular path.

Such a method further includes determining if the rotation of the drill bit in a first direction formed a complete channel or a partial channel and in the case where it is determined that a partial channel was formed, reconfiguring the drill assembly so as to be rotatable in a second rotational direction that is different from the first direction and rotating the drill bit in the second rotational direction to form the complete channel.

Such methods further include locating and attaching an implant in the channel so formed and securing the implant therein using any of a number of techniques known to those skilled in the art. In more particular embodiments, such a method include securing the implant to the bone, bony structure or vertebra using a plurality or more of securing devices, more specifically using a plurality of threaded members.

Such methods further include forming a plurality or more channels in one or more surfaces of the bone or bony structure segments or adjacent vertebra or a channel submerged within the bone or bony structure segments or adjacent vertebra. In particular embodiments, two channels are formed submerged within the bone or bony structure segments or adjacent vertebra. In further embodiments, such methods include locating an implant in each of the plurality or more channels so formed and securing the implant therein using any of a number of techniques known to those skilled in the art. In more particular embodiments, such methods include securing the implant to the bone, bony structure or vertebra using a plurality or more of securing devices, more specifically using a plurality of threaded members. It should be noted that the term adjacent vertebrae includes the sacrum.

In further embodiments, such implants include a sliding implant device comprising two implant members, one of which is disposed in sliding relation with respect to the other. Thus, such methods further include implanting the sliding implant device such that one member is securably retained to, or within, one of the adjacent vertebrae; such that the other member is securably retained to, or within, the other of the adjacent vertebrae; and such that the sliding interconnection between the two members is located in the intravertebral space between the adjacent vertebrae.

In further embodiments, the two implant members also are configured so as to include stops, elements or surface artifacts in opposing surfaces of the two members that cooperate so as to restrain further relative movement between the two members. More particularly, such stops, elements or surface artifacts are arranged so as to prevent the two members from being displaced in a direction that would allow the said one member to slide out an end of said other member, thereby breaking the sliding interconnection between the two members. In illustrative embodiments, each such stop comprises a vertically extending member that extends upwardly from each of the opposing surfaces and which extends at least partially about the circumference of each member.

In further embodiments, such implants include a dynamized implant device comprising two implant members and a compressive segment compressibly interconnecting the two implant members. Thus, such methods further include implanting the dynamized implant device such that one member is securably retained to, or within, one of the adjacent vertebrae; such that the other member is securably retained to, or within, the other of the adjacent vertebrae; and such that the compressive segment is located in the intravertebral space between the adjacent vertebrae. In particular embodiments, the compressive segment further includes a resilient element or feature (e.g., spring or compressible material) that in effect controls or limits the amount of compression or movement between the two members.

According to further aspects of the present invention there is featured a method for forming a channel, an arcuate channel in adjacent vertebra of a lower portion of the spine, more particularly between the lumbar vertebrae and more specifically, between the lowest lumbar vertebrae (L-5) and the sacrum. Such a method includes positioning a frame assembly proximal the treatment or surgical site, securing the frame assembly to the adjacent segments of the adjacent vertebra including the lumbar vertebrae L-5 and the sacrum and rotating a drill bit in fixed relation to the frame assembly to form the channel in the surface or sub-surface of the bone, bony structure or vertebra. In further embodiments, the method further includes mechanically engaging a securing mechanism to the frame assembly so that the frame is maintained in fixed relation by such mechanical engagement alone or in combination with the lateral stiffness of the securing mechanism.

In further embodiments, the provided frame assembly is configured to accommodate relative differences in the surface and the height or elevation between the adjacent vertebrae including the lumbar vertebrae L-5 and the sacrum so the channel being formed follows a desired path through the adjacent vertebrae. In more particular embodiments, a portion of the frame assembly is configured so the pivot point of the rotating drill point is in fixed relation with respect to the desired path.

According to further aspects, such methods further includes removably attaching a spacer element to the frame assembly so as to maintain alignment of the spacer with respect to the frame as well as with respect to the channel being formed in adjacent vertebrae and releasing the spacer element from the frame assembly following forming of the channel in the adjacent vertebrae using any of the methods described herein. In one embodiment, the spacer element includes a preformed aperture and said attaching includes attaching the spacer element to the frame assembly so as to maintain alignment of the preformed aperture with respect to the frame as well as with respect to the channel being formed in adjacent vertebrae. In another embodiment, said method includes forming an aperture in the spacer element, preferably when forming the channel in the adjacent vertebrae. Such spacers can be formed from any of a number of materials, including bone, metal, allograft or autologous as well as using any of a number of techniques known to those skilled in the art. It also is contemplated that such spacers remain in the intervertebral disc space following the procedure being performed that embodies the methodologies of the present invention as well as devices, apparatuses and systems of the present invention.

Also featured is a system or apparatus embodying the frame, pivot arm assembly and drill assembly herein described. In addition there is featured devices or tools for use with such systems, apparatuses and methods to drive the securing members or the remove the securing members after the channel has been formed in the surface or sub-surface of the bone, bony structure or adjacent vertebras.

In further aspects of the present invention, there are featured systems, apparatuses and methods for augmenting, repairing or replacing the nucleus and/or the annulus that embody the frame, pivot arm assembly and drill assembly herein described as well as other such systems and apparatuses described in U.S. Pat. No. 6,607,530 and U.S. Ser. No. 10/019,265 (the teachings of which are incorporated herein by reference). In such systems, apparatuses and methods, the drill is rotated as described herein to form a channel or passage through one of the vertebrae that is adjacent to the disk to be repaired so that the nucleus of the disk can be accessed through the vertebral end plate. The size of the channel or passage formed can be controlled so as to provide the desired or needed amount of access for the surgeon to insert for example, the material or prosthetic into the nucleus as well as other devices or mechanisms (e.g., a patch) that can be used to form a seal or closure at the defect on the annulus. Such control is achieved for example, by adjusting the size of the drill bit to fit a given application. Such a disk repair procedure also can include sealing of the channel, passage or hole formed in the vertebrae using any of a number of techniques known to those skilled in the art, such as for example, inserting bone or bony material into the channel.

It should be recognized that the drilling apparatus, methods and systems of the present invention can be used anteriorally or posteriorally and so that the drill bit of such systems or apparatuses can penetrate or enter the vertebral body through the pedicles.

Other aspects and embodiments of the invention are discussed below.

BRIEF DESCRIPTION OF THE DRAWING

For a fuller understanding of the nature and desired objects of the present invention, reference is made to the following detailed description taken in conjunction with the accompanying drawing figures wherein like reference character denote corresponding parts throughout the several views and wherein:

FIGS. 27A-C are top, side and cross-sectional end views respectively of another embodiment of the illustrative frame according to said another aspect of the present invention;

FIGS. 34A-B and F-G are top, bottom and side views respectively of second illustrative embodiment of a cap according to the present invention;

FIG. 34C is a cross-section view along section M-M of FIG. 33A;

FIG. 34D is a cross-section view along section L-L of FIG. 34A;

FIG. 34E is a cross-section view along section R-R of FIG. 34B; and

DESCRIPTION OF THE PREFERRED EMBODIMENT

Figure 1:
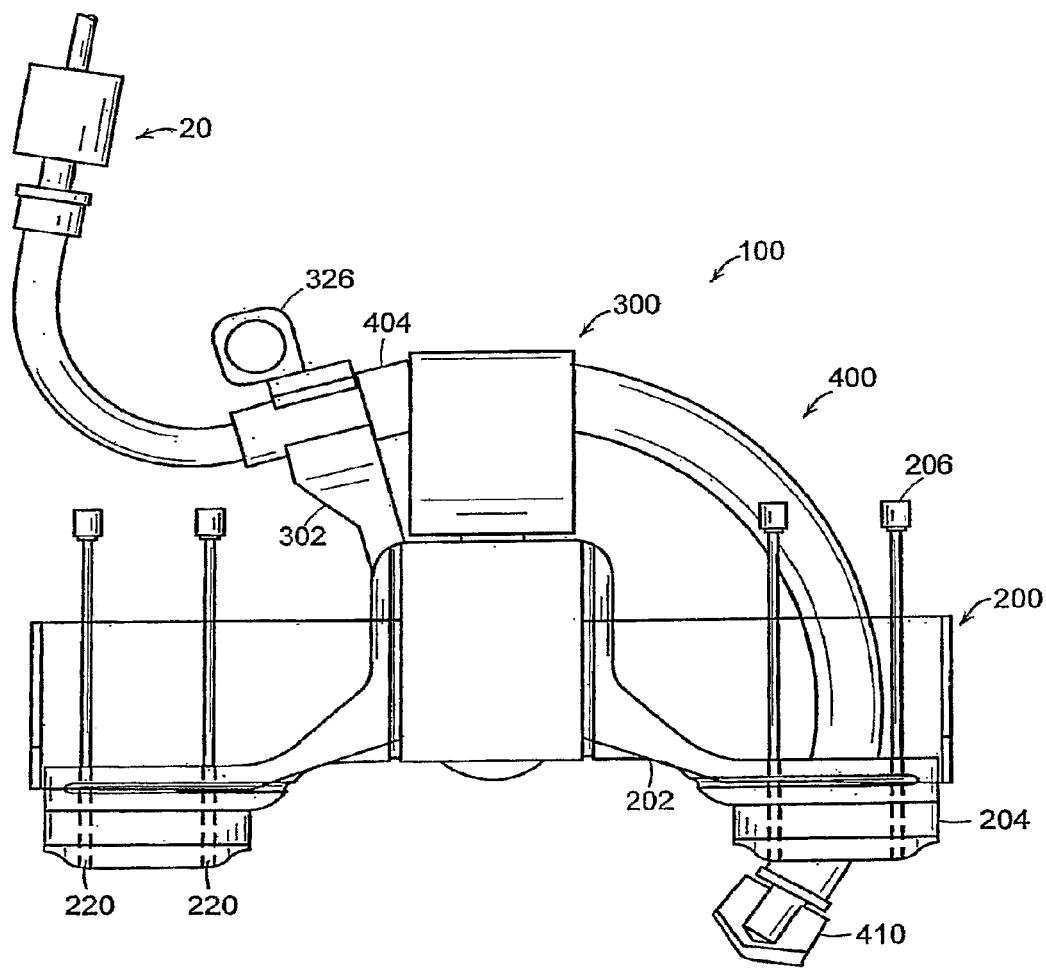
FIG. 1 is a side view of a drilling apparatus according to an aspect of the present invention.
Figure 2:
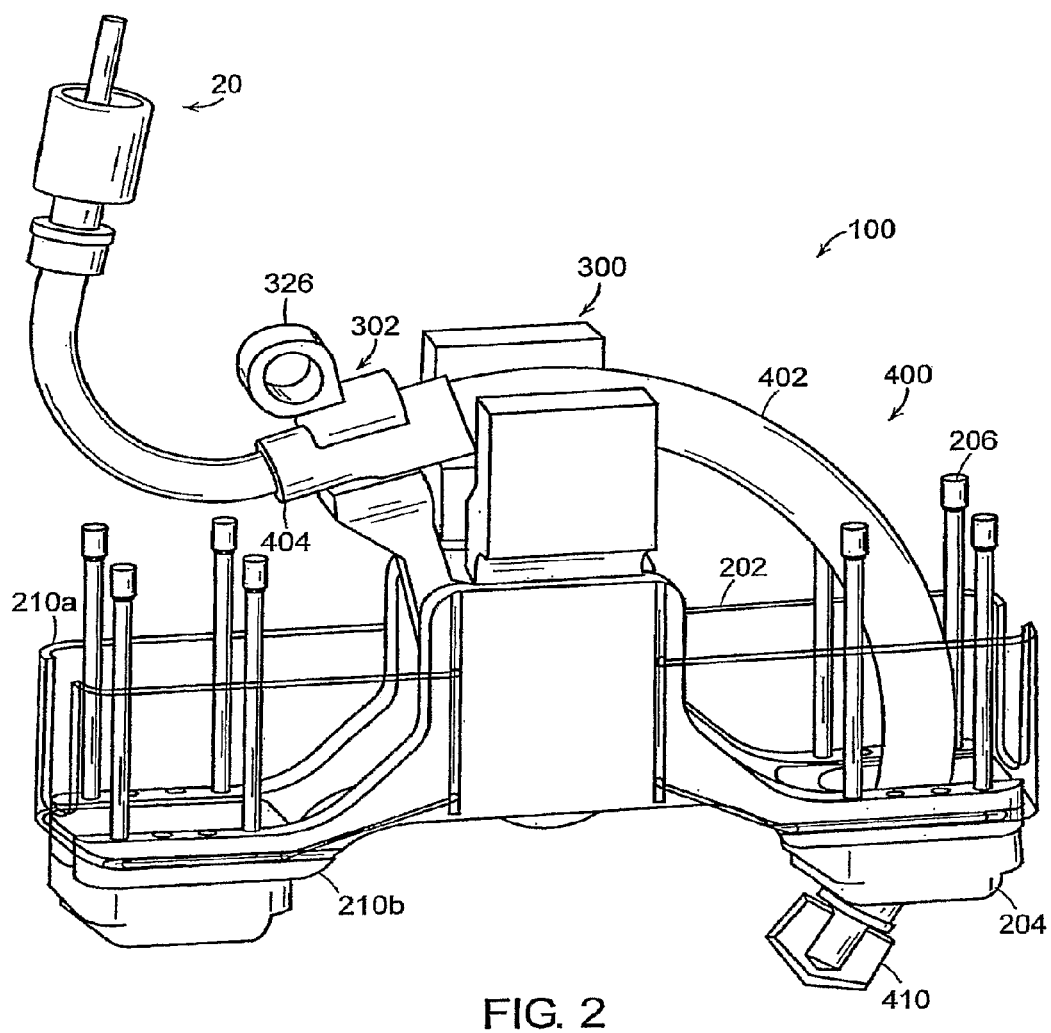
FIG. 2 is one perspective view of the drilling apparatus of FIG. 1.
Figure 3:
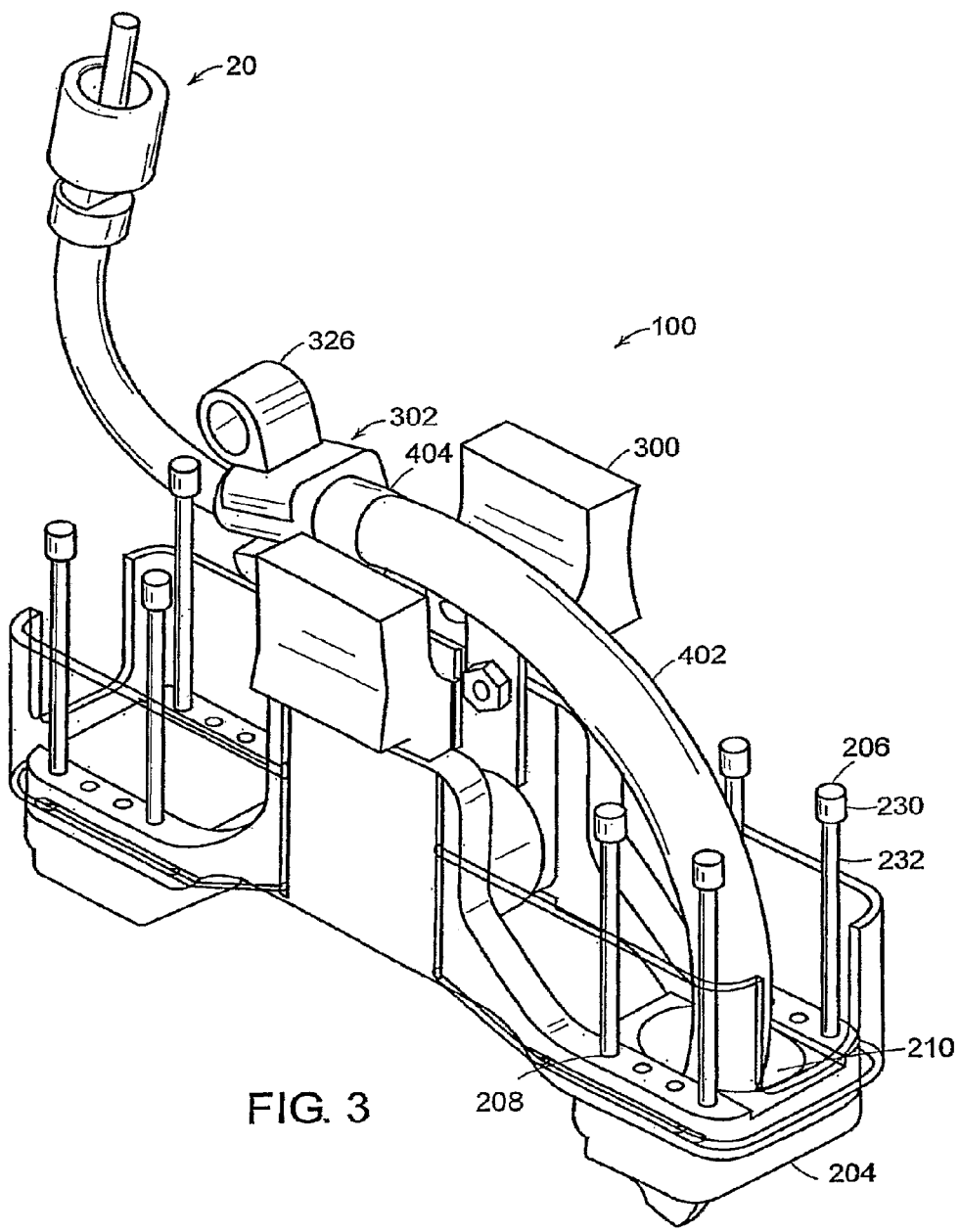
FIG. 3 is another perspective view of the drilling apparatus of FIG. 1.

Referring now to the various figures of the drawing wherein like reference characters refer to like parts, there is shown in FIGS. 1-3 various views of a drilling apparatus 100 according to an aspect of the present invention that is generally comprised of a platform assembly 200, a pivot arm assembly 300 and drill assembly 400. As hereinafter described in more detail, the pivot arm assembly 300 is removably secured to the platform assembly 200 and the platform assembly is removably secured to the bone or bony structure so as to maintain the pivot point of the pivot arm assembly in general fixed relation to the bone or bony structure. The drill assembly 400 is removably secured to the pivot arm assembly 300 so as to maintain the end of the drill assembly including the bit 410 or drill end in fixed relation with respect to the pivot arm 302 of the pivot arm assembly. Consequently, as the pivot arm 302 is rotated about the pivot point, the bit 410 follows a predetermined arcuate, curved or circular path in the bone or bony structure as defined by the length of the pivot arm.

For purposes of illustrating the drilling apparatus 100 of the present invention, reference hereinafter is generally made to the structure and structural features or elements of a mammalian spine (e.g., human spine), however, this shall not be construed as limiting the use and application of the drilling apparatus of the present invention to these applications. It is contemplated and as such within the scope of the present invention to adapt the drilling apparatus of the present invention and the methods related thereto so the drilling apparatus is used so as to form grooves or arcuate passages in bones or bony structures of the mammalian body in which grooves is received a curved rod or other member as is hereinafter described thereby stabilizing and/or supporting the bone or bony structure.

The platform assembly 200 includes a frame 202, a plurality of first path guards 204 and a mechanism for securing the frame to the bone or bony structure. In the illustrated embodiment, the securing mechanism comprises a plurality of nail members 206 that each pass respectively through each of the frame 202 and the first path guards and so as to be disposed in the bone or bony structure as herein described. In further embodiments, and as hereinafter described, the platform assembly 200 can further include a second path guard 204b, in cases where the drilling apparatus 100 is used to form a groove or recess in an outer surface of the bone or bony structure thereby providing a protective structure between the moving and rotating drill bit 410 and the tissues or other structures or features of the mammalian body (e.g., nerves, blood vessels) that are proximal the bone or bony structure outer surface.

The frame 202 is configured and arranged so as to form an essentially rigid structure and frame work to which the pivot arm assembly 300 is removable attached and at least one and more particularly two through passages 210 that communicate with a corresponding passage in the first path guards 204. The through passages 210 and the corresponding passage in the first path guards 204 are each configured and arranged so as to allow the outer tube member 402 of the drill assembly to pass there through as the pivot arm 302 is being rotated or pivoted about the pivot point. The frame 202 is composed of any one of number of materials known to those skilled in the art that is appropriate for the intended use and the anticipated structural loads that can be imposed during use. In an exemplary embodiment, the frame 202 is made from stainless steel such as a stainless steel bar stock.

The first path guards 204 are secured to the frame 202 so as to extend downwardly from a bottom surface 210b therefrom. Each of the first path guards 204 are arranged so as to include a generally centrally located through passage, through which the outer tube member 402 and the drill bit 410 or burr of the drill assembly 400 are passed. In addition, each of the first path guards 204 are configured and arranged so as to include a plurality of through passages 220, one for each of the nail members 206. Each of the nail member through passages 220 also are preferably formed in the first guard member so as to present constricted holes that firmly grab the nail member within the corresponding through passage. In this way, the gripping action of the through passages and the lateral stiffness of the nail members 206 provides a mechanism for supporting and fixing the frame 202, and in turn the pivot point's relation with respect to the bone, bony structure or spine. In use, each of the nail members 206 are passed through the through aperture 208 in the frame 202 and driven through the through passage 220 of the first path guard 204.

In more particular embodiments, each through passage 220 is configured and arranged so that the passages are over sized with respect to the diameter of the nail members 206 and a portion of the through passage forms a land or raised region comprising a constriction region. More particularly, the constricted region is located above or from the lower end of the through passage such that the pointed ends of each nail member 206 are not exposed when the nail members 206 are initially pressed into the platform assembly 200. In this way, each of the nail members 206 are confined within the first path guard 204 prior to positioning of the platform assembly 200 in the surgical field amidst vital structures or features of the mammalian body.

The first path guards 204 are constructed from any of a number of materials known to those skilled in the art that are appropriate for the intended use and so as to provide a medium that can form a protective barrier between the drill path and the tissues including nerves and blood vessels that are proximal the site of the bone, bony structure or spine to be drilled. In exemplary embodiments, the first path guards 204 are made form a plastic material such as, but not limited to, polycarbonate. In further embodiments, the end of the first path guard 204 proximal the bone, bony structure or spine is configured and arranged so as to include a soft conformal region that contact and seal against the surface of the bone, bony structure or spine. Alternatively, a conformable material may be disposed in the space, if any, between the base or bottom surface of each first path guard 204 and the opposing surface of the bone, bony structure or spine (e.g., vertebral cortex).

The nail members 206 are configured and arranged so that each extends from a top surface 210a of the frame 200, through the frame and the first path guard 204 and a sufficient distance into the bone, bony structure or spine to fix and secure the frame thereto. In addition, each of the nail members 206 also is configured and arranged so at least a portion thereof has a diameter that is set so that this portion of the nail member is gripped within the constricted region of the through passage 220 of the first path guards 204 as herein described.

Each of the nail members 206 includes a head portion 230 and a shaft portion 232 one end of which is mechanically coupled to the head portion using any of a number of techniques known to those skilled in the art that yields a nail member that is capable of being driven into the bone, bony structure or spine and removed therefrom. In further embodiments, the nail member 206 is formed such that the head portion 230 is integral with the shaft portion 232. In particular embodiments, the head portion 230 is configured and arranged so as to allow the nail member 206 to be driven through and into the bone, bony structure or spine and later removed therefrom. In further embodiments, the head portion 230 is further configured so as to include a through aperture or hole extending generally laterally or radially through the head portion, the through aperture being configured to receive one or more suture lines therein for interoperative locating.

The other end of the shaft portion 232 is configured so as to form a pointed end that is appropriately configured and shaped for insertion into the bone, bony structure or spine and for securing the pointed end and a portion of the shaft member in such bone, bony structure or spine. In illustrative embodiments, the pointed end is configured to form a non-cutting pencil point end that wedges the end into the bone, bony structure or spine.

In the illustrated embodiment, four nail members 206 are driven through each of the first guard members 204 and into the bone or bony structure or spine. This shall not be construed as a limitation as the number and placement of the nail members is not so particularly limited as each end of the frame 202 can be secured to the bone or bony structure using one or more and more particularly two or more nail members 206. It also should be recognized that other mechanisms known to those skilled in the art, such as screws or threaded devices, are contemplated for use with the present invention.

Each of the nail members 206 is composed of any one of number of materials known to those skilled in the art that is appropriate for the intended use and the anticipated structural loads that can be imposed during use. In an exemplary embodiment, the nail member 206 is made from a metal such as stainless steel.

Figure 4A:
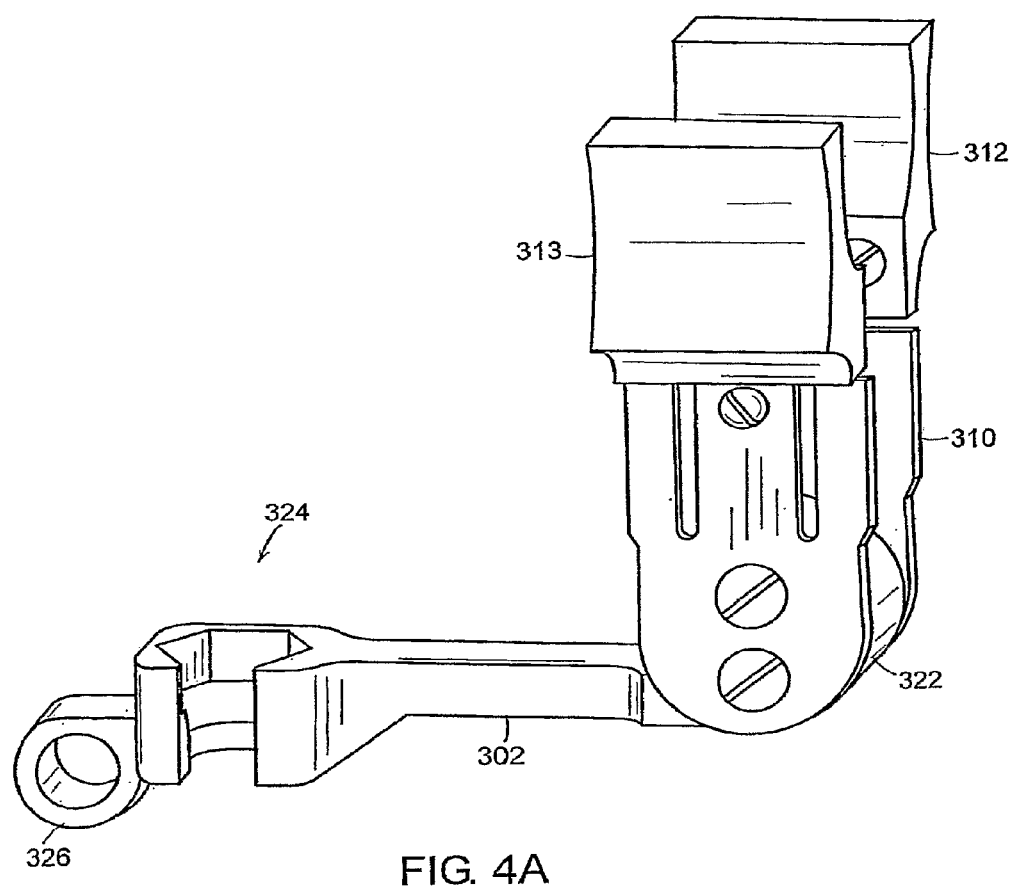
FIGS. 4A,B are various perspective views of the pivot arm assembly of the drilling apparatus of FIG. 1.
Figure 4B:
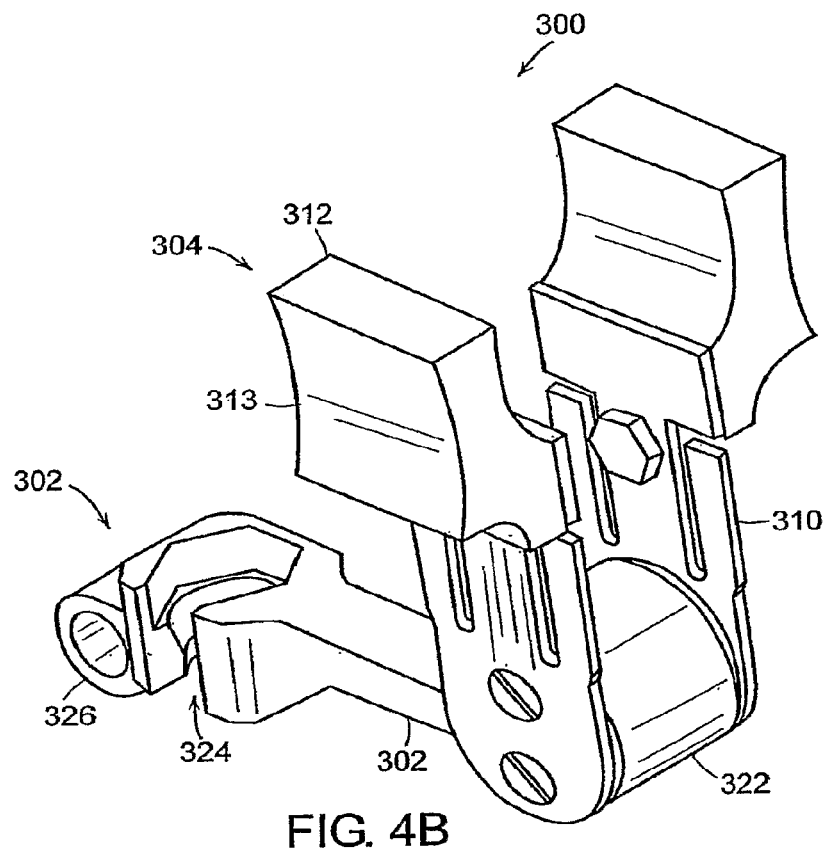
Figure 5:
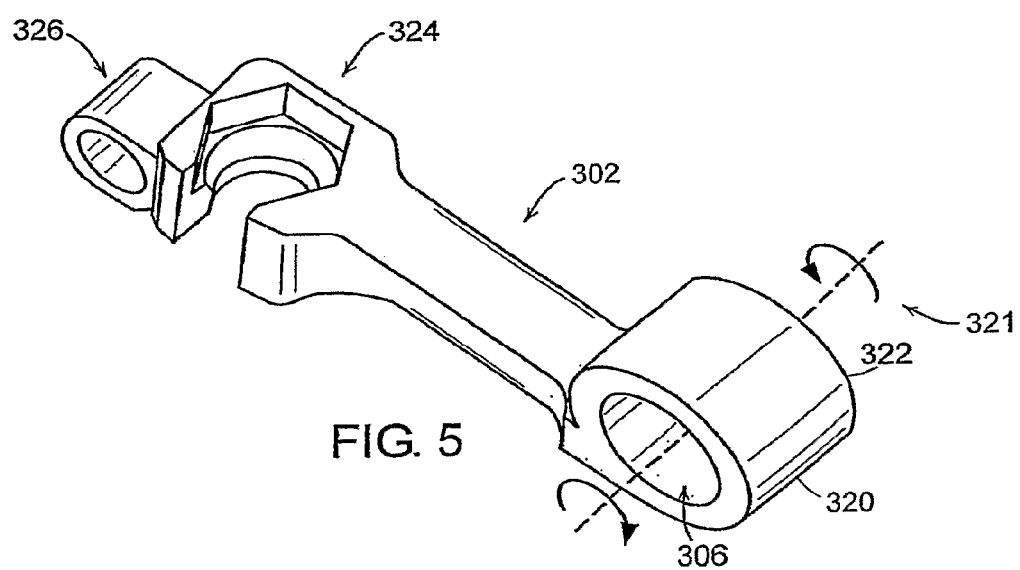
FIG. 5 is a perspective view of the pivot arm of the pivot arm assembly.

Referring now also to FIGS. 4-5, the pivot arm assembly 300 includes a radial arm or pivot arm 302, a pivot pin bracket 304 and a pivot pin 306. The pivot pin bracket 304 includes side plates 310 and finger pads 312 that are secured to the side plates, where the pivot pin extends between the side plates. The pivot pin 306 is received within an aperture 320 in the pivot arm such that the pivot arm can rotate about a pivot axis 321.

The pivot pin bracket 304, more particularly the side plates 310 thereof, is generally configured and arranged so as to secure the pivot arm assembly 300 to the platform assembly 200 so as to prevent the disengagement of the pivot arm assembly and correspondingly the drill assembly 400 from the platform assembly when it is being rotated from the fully retracted position of the pivot arm. More particularly, the side plates thereof are configured and arranged such that the bracket can be removed from the platform assembly 200 when the pivot arm is in the fully retracted position.

In particular embodiments, the side plates 310 are configured so as to form spring members that can slide in mating grooves provided on opposing inside surfaces of the platform assembly frame 202. In addition, the side plates 310 further include binding head screws that engage complimentary holes within the mating grooves to lock the pivot pin bracket 304 in place. A finger pad 312 is secured to an end of each side plate so as to facilitate placement and removal of the pivot pin bracket 304 in the platform assembly. In illustrative embodiments, the finger pads 312 are configured so as to include concavities 313 that the fingertips of the user can engage to thereby facilitate placement and removal of the pivot pin bracket 304.

The pivot arm 302 is configured and arranged so an end 322 thereof includes an aperture 320 so the pivot arm can be mounted upon the pivot pin 306 such that it can rotate or swing about the pivot pin 306. The pivot arm 302 also is configured and arranged so as to include a mating portion 324 that receives therein and mates with a feature of the drill assembly 400 so as to removably secured the drill assembly to the pivot arm. The mating portion 324 is located distal from the end 322 of the pivot arm 302 that is mounted upon the pivot pin 306. Also, the length of the pivot arm 304, more particularly the distance between the pivot axis 321 and the mating portion 324, establishes or controls the radius of curvature of the hole or recess being formed in the bone, bony structure or spine by the rotation of the pivot arm. It should be noted that this radius of curvature or diameter is different from the diameter of the hole or recess formed by the rotating drill bit 410 or bur. As such, it is contemplated that pivot arms 302 will be provided that have lengths set that are appropriate for the given geometry and physical make-up of the mammalian body.

The platform assembly 200 and pivot arm assembly 300 of the present invention advantageously creates a mechanism that allows tissue, muscle, blood vessels (e.g., aorta) and nerves to pass under and around the platform assembly and also to localize the drilling elements of the drill assembly 400 within the structure of the platform assembly. In addition, the pivot arm assembly 300 in combination with the platform assembly provides a mechanism to control the radial movement or radial motion of the drilling elements of the drill assembly 400 from their insertion into the bone or bony structure as well as the retraction from the bone or bony structure such that the drilling elements traverse a specific radius of curvature during such insertion and retraction. In this way, the drilling apparatus of the present invention also controls the maximum depth within the bone or bony structure the drilling elements can attain during use. Thus, and in contrast to conventional techniques, devices and instrumentalities, the drilling apparatus 100 of the present invention provides a mechanism that protects tissues, blood vessels and nerves from damage while the drilling elements of the drill assembly 400 are being inserted into and withdrawn from the bone or bony structure as well as assuring that the drilling elements will follow a generally fixed path such that the drilling elements do not come into contact with nor damage the tissues, blood vessels and nerves proximal to and surrounding the bone or bony structure while the hole or recess is being formed in the bone or bony structure. Consequently, the drilling apparatus 100 of the present invention minimizes the potential for damage without having to rely solely on the dexterity or skill of the surgeon, as is done with conventional techniques and devices.

In further embodiments, at least a segment or a part of the mating portion 324 is configured and arranged so as to complement the shape of the drive assembly feature being received therein. For example, and as illustrated, a portion or part of the key 404 of the drill assembly is configured so as to be polygonal in shape and the mating portion 324 is configured so as to include a polygonal shaped recess for receiving therein the hexagonal surfaces of the key. Such polygonal shapes includes but are not limited to a square, triangular, rectangular or hexagonal shapes.

In yet further embodiments, the pivot arm 302 is configured and arranged so as to include a finger grip 326 at or proximal and end of the pivot arm that is opposite to the end 322 mounted upon the pivot pin 306. The finger grip 326 presents a structural element or feature that is configured to allow the thumb and/or fingers of the user to grasp the finger grip so as to thereby control rotation of the pivot arm and to also control the drilling pressure (i.e., pressure being exerted by the drill bit 410 on the bone or bony structure while drilling the hole or recess therein). In illustrated embodiments, the finger grip 326 presents a small tab having bilateral concavities that allow the finger tips to grasp it or a through aperture.

Each of the pivot arm 302, pivot pin 306, side plates 310 and finger pads 312 is composed of any one of number of materials known to those skilled in the art that is appropriate for the intended use and the anticipated structural loads that can be imposed during use. In an exemplary embodiment, any one or more of the foregoing elements of the pivot arm assembly 300 is made from a metal such as stainless steel.

Figure 6:
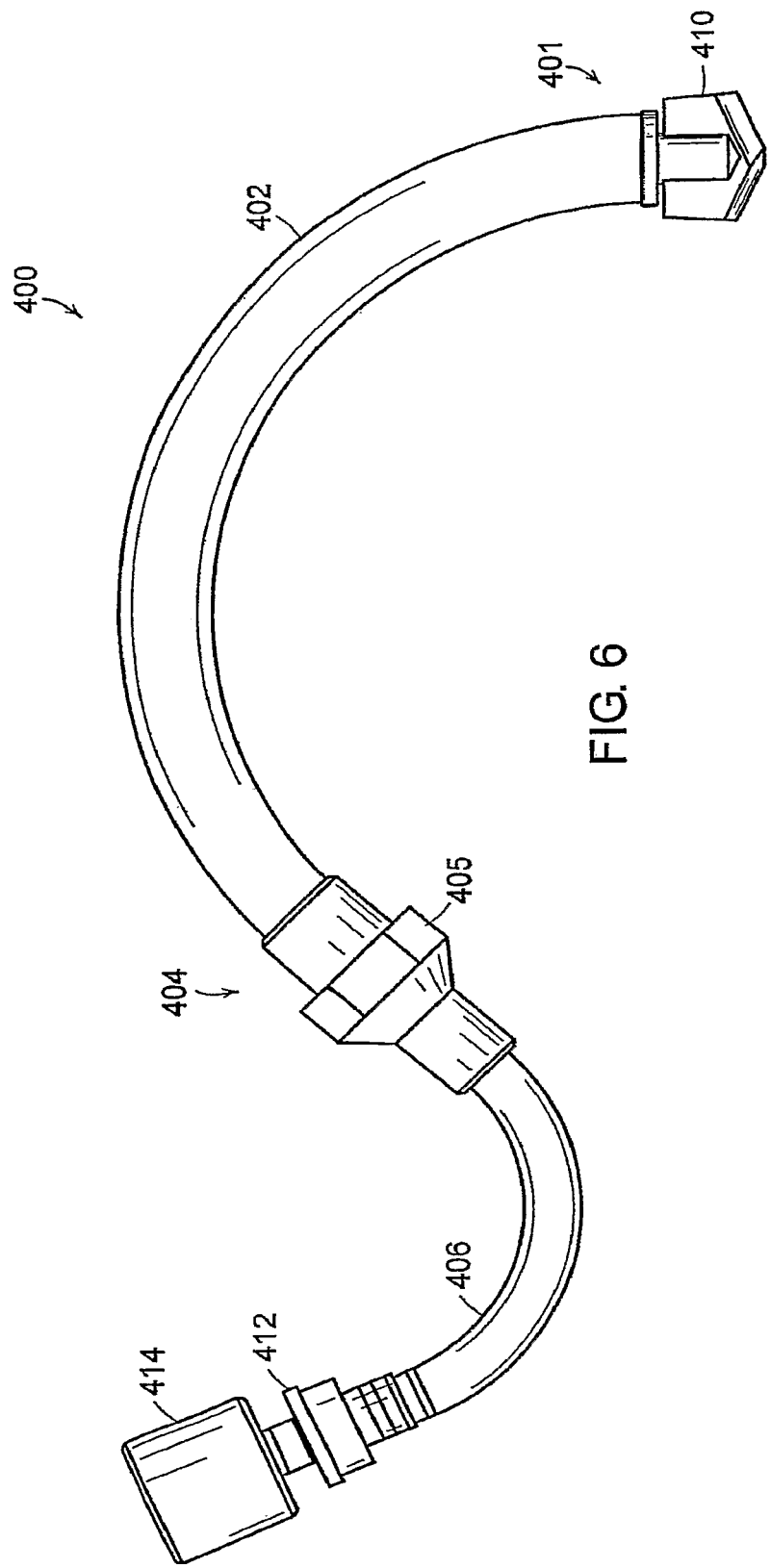
FIG. 6 is a perspective view of the drill assembly of the drilling apparatus and a drive motor connected thereto.
Figure 7:
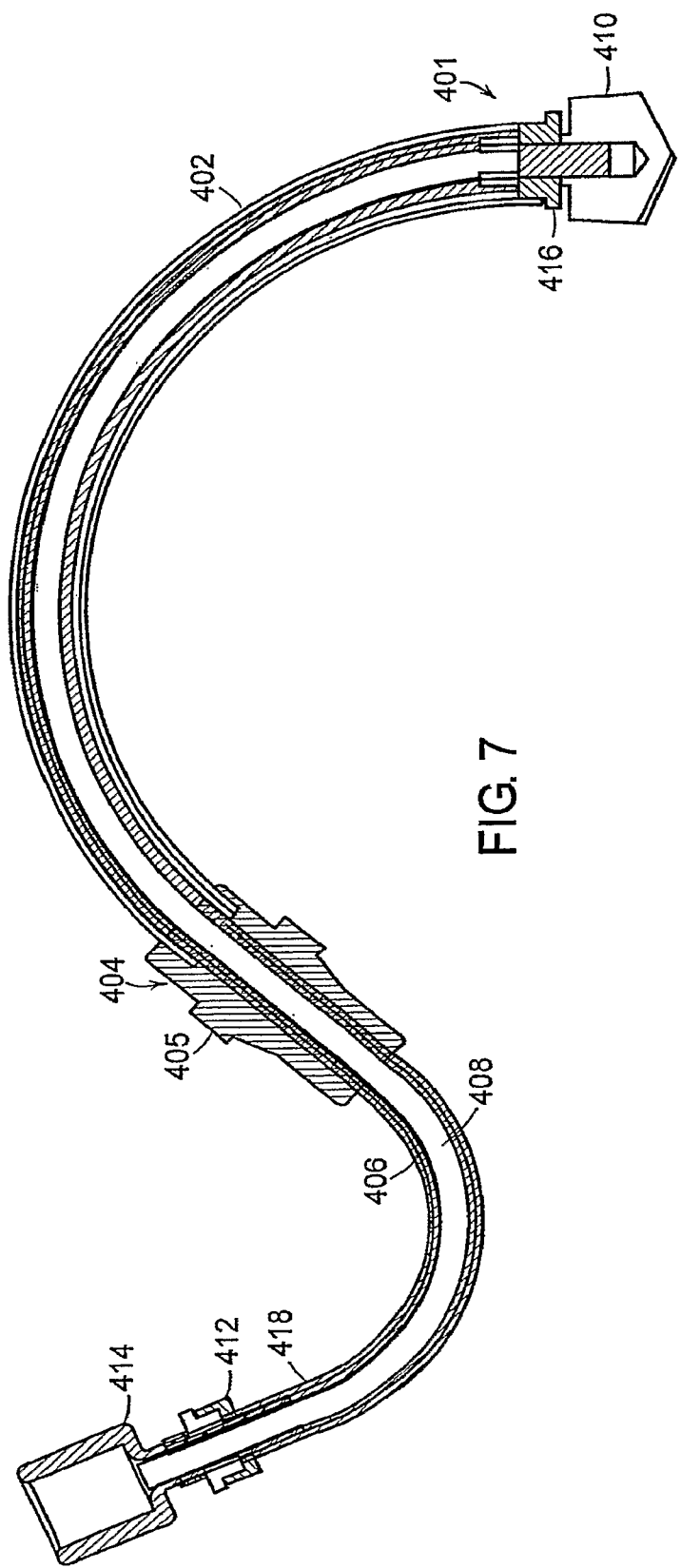
FIG. 7 is a cross-sectional side view of the drill assembly of FIG. 6.
Figure 8:
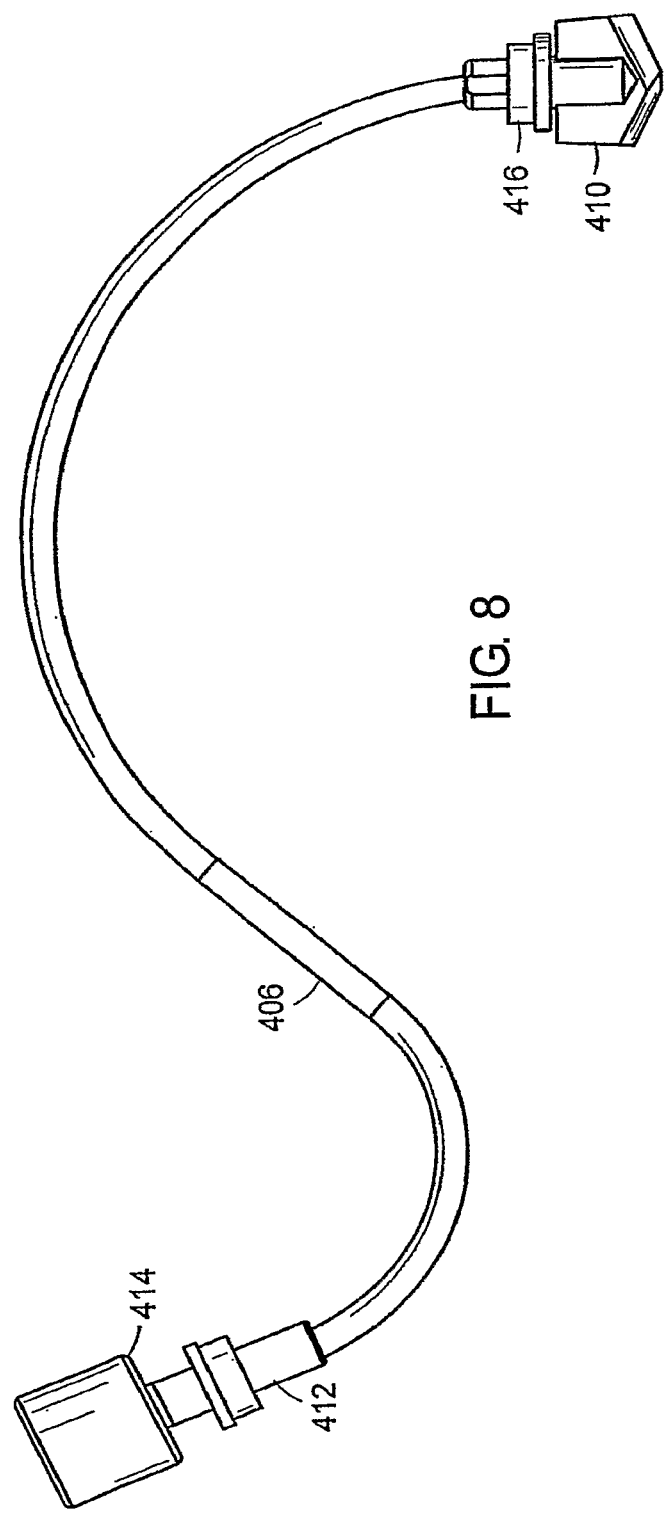
FIG. 8 is a side view of the bit, bearing and drive cable sub-assembly of the drill assembly.
Figure 9:
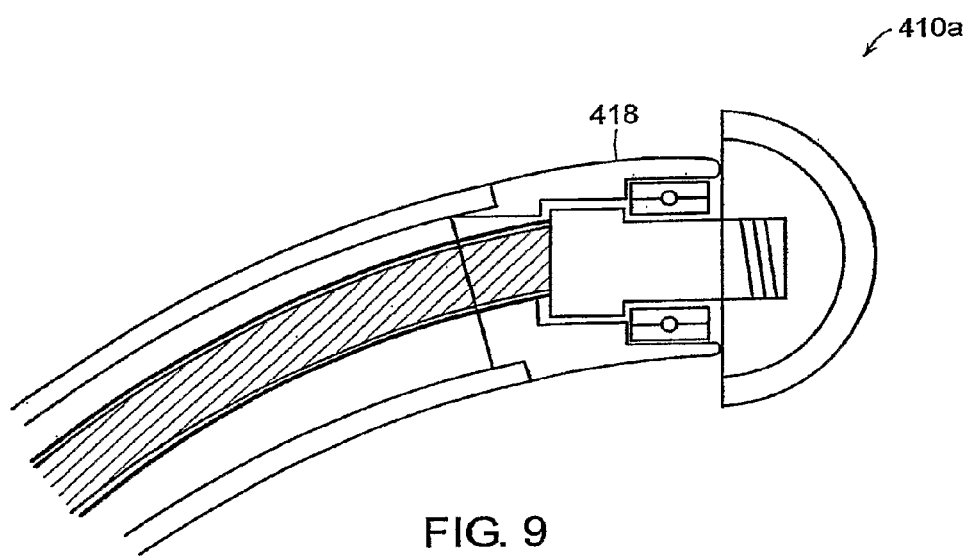
FIG. 9 is a cross-sectional view of the drill assembly end including the bit, illustrating another exemplary bit.

Referring now also to FIGS. 6-7 there is shown a perspective view and a cross-sectional view of drill assembly 400 of the present invention. There also are shown in FIGS. 8-9 various views of portions or segments of such a drill assembly and/or embodiments thereof. The drill assembly 400 generally forms a curved structure, more particularly a curved tubular structure, that is attached to the pivot arm 302 as herein described and which thus swings around the pivot point or pivot axis 321. In use, the drill bit 410 rotates about its axis while this axis is held tangent to and swept along an arc of constant radius as defined by the distance between the mating portion 324 of the pivot arm 302 and the pivot axis 321. This movement results in or yields a toroidal hole.

The drill assembly includes an outer tube member 402, a key 404, a flexible inner housing 406, a drive cable 408, a drill bit 410 or bun, a barbed fitting 412, a drive adapter 414. In further embodiments, the drill assembly includes a distal drive cable bearing 416 and a proximal drive cable bearing 418. Any one of a number of motors 20 or motor drive assemblies as is known in the art having sufficient power (e.g., torque) and rotational speed are coupled to the drive adapter 414 including but not limited to the Micro100 (Linvatech/Hall Surgical 5053-009) or Blachmax (Anspach Blackmax-KT-0). The drive adapter 414 is a swage-type of fitting that is configured and arranged so it can be swaged upon one end of the drive cable 408. The drive adapter 414 also is configured and arranged so as to provide an input end arrangement that can be mechanically coupled to the output end of a variety of motors or motor drive assemblies or drills including those identified herein.

The outer tube member 402 is curved to a predetermined radius of curvature so that the centerline thereof is a set distance from the pivot axis 321 of the pivot arm 302. The key 404 and the distal cable bearing 416 are secured to the outer tube using any of a number of techniques known to those skilled in the art that is appropriate for the materials comprising these elements or features. In exemplary embodiments, the key 404 and the distal cable bearing 416 are secured to the outer tube member by brazing or soldering. In more particular embodiments, the distal drive cable bearing 416 is secured to the outer tube member 402 such that the outer edge of the outer race of the bearing lies in a radial plane from the pivot point, whereby the axis of the drill bit 410 or burr is arranged so as to tangent to the centerline of the arc of the outer tube member.

The key 404 is generally cylindrical in construction and serves to align and anchor the outer tube member 401 to the pivot arm assembly 300, more particularly the pivot arm 302. As indicated herein, a portion 405 of the key 404 is configured so as to provide a surface feature, artifact or contour that complements at least a part of the mating portion 324 of the pivot arm. In the illustrated embodiment, the portion 405 of the key 404 forms an external polygonal feature that mates to the internal polygonal feature provided in the pivot arm mating portion. The key 404 also is configured and arranged so as to be secured to the mating portion using any of a number of techniques known to those skilled in the art. In an exemplary embodiment, a portion of the key is configured so as to include a external thread and a part of the mating portion 324 is configured so as to include a complementary threaded element or feature in an aperture thereof. In use, the key is articulated so as to threadably secure or lock the key 404 to the pivot arm 302. Other techniques for securing, such as brazing, soldering and adhesives are contemplated for use with the present invention.

The key 404 includes a through aperture that is coupled to the inner region or area of the outer tube member 402. The diameter of the key through aperture and the outer tube member are set so as to at least allow the flexible inner housing 406 and the drive cable 408 to pass there through. The flexible inner housing 406 extends from the distal end 401 of the outer tube member 402 to the barbed fitting 412. The flexible inner housing 406 is a generally tubular member of flexible construction, such as Teflon for example, for housing the drive cable 408. In particular embodiments, the flexible inner housing 406 is a small diameter tubular member (i.e., smaller than the inner diameter of the outer tube member) and is secured the key 404 using any of a number of techniques known to those skilled in the art, which are appropriate for the materials of use. In an exemplary embodiment, the flexible inner housing is secured to the key 404 using an adhesive, such as a medical grade adhesive.

The barbed fitting 412 is secured to the end of the flexible inner housing that is opposite to the drill bit 410 using any of a number of techniques known to those skilled in the art, which are appropriate for the materials of use. The end of the barbed fitting 412 being secured to the flexible inner housing 406 also is received within the flexible inner housing. In particular embodiments, the barbed fitting 412 is configured and arranged so the end being received in the flexible inner housing 406 is secured thereto by an interference fit. In further exemplary embodiments, the interference fit is augmented by use of an adhesive, such as a medical grade adhesive.

The proximal drive cable bearing 418 is disposed within the barbed fitting 412 in which is received the drive cable 408. In particular embodiments, the proximal drive cable bearing 418 is retained within the barbed fitting 412 using any of a number of techniques known to those skilled in the art. In an exemplary embodiment, the proximal drive cable bearing is secured to the barbed fitting using one of soldering, brazing or adhesives.

The distal and proximal drive cable bearings 416, 418 are any of a number of bearing assemblies known to those skilled in the art and appropriate for the intended use. In particular embodiments, the distal and proximal drive cable bearing 416, 418 are miniature ball bearing assemblies as is known to those skilled in the art (e.g., SR133zz MSC 35380799, 0.9375" bore, 0.1875" OD, 0.0937" width, double shielded).

In an alternative embodiment, the inner housing is a double curved inner tube of a fixed non-flexible construction. The double curved inner tube has two radii of curvature, the first radius of curvature involves all but the most distal section of the inner tube and the second radius of curvature involves a smaller portion of the inner tube. The second radius of curvature is set so as to bring the path of the drive cable 408 around so as to enter the proximal end of the distal drive cable bearing 416 in the correct direction. In this way, the fixed inner tube can be configured and arranged so as to swing wide and make a turn to enter essentially parallel to the axis of an end fitting being swaged to the end of the inner tube. In this way, fatiguing of the drive cable 408 can be minimized and misalignment of the drive cable and the inner tube proximal the end of the inner tube can be minimized.

Although specific embodiments are described herein for the outer tube member 402 and the inner tube member or flexible inner housing 406 this shall not be considered as particularly limiting. The present invention contemplates adapting the present invention using any of a number of techniques known to those skilled in the art whereby a cable is generally turned through a protected series of rigid or flexible cannulas or tubes such that a bit operably coupled to one end of the cable can turn at an end of the outer tube or cannula.

The drill bit 410 or burr is any of a number of cutting tools or implements known to those skilled in the art and appropriate for the intended use, speed and power developed by the drive motor 20 and the material to be drilled. In particular illustrative embodiments, the drill bit 410 or burr is a spade bit such as that shown in FIGS. 6-8, alternatively and with reference to FIG. 9, the drill bit is a hemispherical bit 410a.

The drive cable 408 is a flexible cable that is more particularly comprised of a large number of smaller strands of an appropriate material, including but not limited to steel, stainless steel, and titanium, that are compound wound using any of a number of techniques known to those skilled in the art so as to yield a flexible cable having the desired width, length, flexibility and strength characteristics. In a particularly illustrative embodiment, the drive cable 408 is a custom wound 1.8 mm (0.072 in.) diameter 7×19 left regular lay strand wound cable. In more particular aspects, the drive cable 408 is manufactured so as to be capable of being rotated or turned at a high rate of speed or revolution while maintaining its flexibility and such that right hand turning of the cable should not result in the unwinding or loosening of construction.

In particular embodiments, the length ("Ldc") of the drive cable 408 shall be controlled so as to maintain a relationship with the length of the portion of the drive cable ("Ldci") that is disposed within the outer cannula or outer tube 402 or correspondingly the arc length of the outer tube. In more particular embodiments, the relationship between the length of the drive cable 408 and the length of the portion of the drive cable within the outer tube 402 satisfies the following relationship $Ldc \leqq 4 \times Ldci$; more particularly satisfies the relationship $Ldc \leqq 3 \times Ldci$, and more specifically satisfies the relationship $Ldc \leqq 2 \times Ldci$. In more specific embodiments, the length of the drive cable 408 is set based on the particular application or material to be drilled. For example, the overall cable length is shortened or lengthened based on the relative hardness of the material in which the channel or opening is to be formed in the bone or bony structure. In further embodiments, the flexible inner housing 406 is configured and arranged so as to have a length that satisfies the foregoing relationships.

Figure 17:
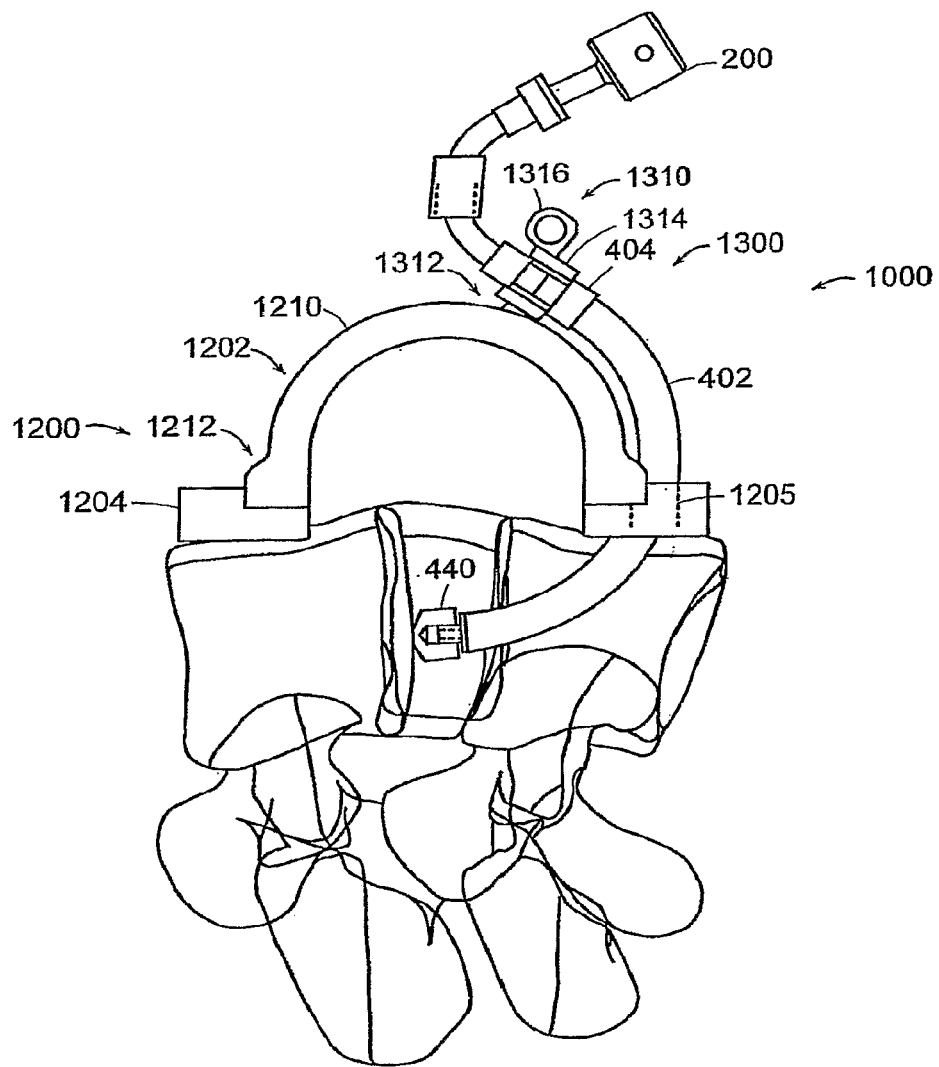
FIG. 17 is a side view of a drilling apparatus according to another aspect of the present invention illustrated disposed upon adjacent vertebral bodies.

Referring now to FIG. 17 there is shown a side view of a drilling apparatus 1000 according to another aspect of the present invention that is illustrated being disposed upon adjacent vertebral bodies. Reference shall be made to FIGS. 1-3 and 6-9 and the discussion related thereto for features and functions not provided in the following discussion. Such a drilling apparatus 1000 includes a platform assembly 1200 and a drill assembly 1300.

The platform assembly 1200 includes a frame member 1202 and a plurality of path guard members 1204 and a mechanism for securing the frame to the bone or bony structure. As with the drilling apparatus illustrated in FIG. 1, the securing mechanism comprises a plurality of nail members 206 that each pass respectively through each of the path guard members 1204 so as to be disposed in the bone or bony structure as herein described. In further embodiments, and as hereinafter described, the platform assembly 1200 can further include a second path guard 205, in cases where the drilling apparatus 1000 is used to form a groove or recess in an outer surface of the bone or bony structure thereby providing a protective structure between the moving and rotating drill bit 410 and the tissues or other structures or features of the mammalian body (e.g., nerves, blood vessels) that are proximal the bone or bony structure outer surface.

The frame member 1202 and the first guard members 1204 are configured and arranged so as to form an essentially rigid structure and frame work to which the drill assembly 1300 is removable attached and at least one and more particularly two through passages 1205. Each of the through passages 1205 are configured and arranged so as to allow the outer tube member 402 of the drill assembly 1300 to pass there through as drill bit 410 is being is being rotated or pivoted about the pivot point. The frame member 1202 is composed of any one of number of materials known to those skilled in the art that is appropriate for the intended use and the anticipated structural loads that can be imposed during use. In an exemplary embodiment, the frame member 1202 is made from stainless steel such as a stainless steel bar stock.

The first path guard members 1204 are secured to the frame member 1202 using any of a number of techniques known to those skilled in the art so that the through aperture 1205 extends downwardly towards a bottom surface thereof. As indicated above, the though passage 1205 in each of the first path guard members 1204 are arranged so the outer tube member 402 and the drill bit 410 or burr of the drill assembly 1300 are passed there through. In addition, each of the first path guard members 1204 are configured and arranged so as to include a plurality of through passages, one for each of the nail members. Reference shall be made to the foregoing discussion for the nail member through passages 220 of FIG. 1 for further detail and characteristics of these nail member through apertures.

The frame member 1202 also is configured and arranged so as to provide a mechanism for guiding the drill assembly 1300 such that the drill bit 410 thereof follows a predetermined arc or radius of rotation. In illustrative embodiments, the frame member 1202 is configured so as to include a web portion 1210 that extends width wise along the circumferential length of the frame member. In further embodiments, the frame member 1202 is configured and arranged so as to form a step region or a discontinuous radial region 1212 at the ends of the frame member proximal the first guard members 1204 so as to form in effect a radial stop.

The drill assembly 1300 generally forms a curved structure, more particularly a curved tubular structure, that is coupled to the frame member 1202 as herein described and which thus swings around a pivot point or pivot axis that is defined by the frame member 1202. In use, the drill bit 410 rotates about its axis while this axis is held tangent to and swept along an arc of constant radius as defined by the pivot pint. This movement results in or yields a toroidal hole in the bone or bony structure.

The drill assembly includes an outer tube member 402, a key 404, a flexible inner housing 406, a drive cable 408, a drill bit 410 or burr, a barbed fitting 412, a drive adapter 414 and moveable mount member 1310. In further embodiments, the drill assembly includes a distal drive cable bearing 416 and a proximal drive cable bearing 418. As indicated above reference shall be made to FIGS. 1-3 and 6-9 for details and characteristics of the drill assembly 1000 not otherwise shown in FIG. 17 or described hereinafter.

The moveable mount member 1310 includes a frame member mounting portion 1312 and a drill assembly mating portion 1314 that form an integral structure. The frame member mounting portion 1312 is configured and arranged so as to be slidably mounted upon the frame member 1202, more specifically the web portion 1210 thereof. Thus, motion of the frame member mounting portion 1312 along the circumference of the frame member 1202 causes the drill bit 410 to in effect rotate about a fixed point, the pivot point defined by the arcuate portion of the frame member.

As with the mating portion 324 of the pivot arm 302, the drill assembly member mating portion 1314 is configured and arranged so as to receive therein the drill assembly key 404. Reference shall be made to the discussion herein for the pivot arm mating portion 324 and the drill assembly key 404 for further details and characteristics of the drill assembly mating portion 1314.

In further embodiments, the moveable mount member 1310 is configured and arranged so as to include a finger grip 1316 at or proximal an end of the mount member 1310 that is opposite to the end frame member 1302. The finger grip 1316 presents a structural element or feature that is configured to allow the thumb and/or fingers of the user to grasp the finger grip so as to thereby control movement of the moveable mount member 1310, rotation of the drill bit 410 and to also control the drilling pressure (i.e., pressure being exerted by the drill bit 410 on the bone or bony structure while drilling the hole or recess therein. In illustrated embodiments, the finger grip 1316 presents a small tab having bilateral concavities that allow the finger tips to grasp it or a through aperture.

In an alternative embodiment, the frame member 1202 is configured and arranged so as to comprise two sub-members being spaced from each other. The two sub-members further include a slot or other feature in opposing surfaces of the sub-members, which slot or other feature extends in the circumferential direction. In this embodiment, the frame mounting portion 1312 of the movable mount member 1310 is configured and arranged so as to be received in and slide within the slot in each of the opposing surfaces. In this way, the drill bit 410 can be rotated about a fixed point defined by the circumferentially arranged slots in the two sub-members. The foregoing is illustrative of a couple of techniques for configuring the frame member 1302 and the frame member mount portion 1312 so the drill bit 410 can be rotated about a fixed point being defined by the structure of the frame member, however, the foregoing shall not be considered limiting as it is within the scope of the present invention to adapt the drilling apparatus of the present inventions so as to provide a mechanism by which the drill bit can be rotated about a fixed point and/or such that the drill bit follows a fixed path during the drilling process.

Figure 18A:
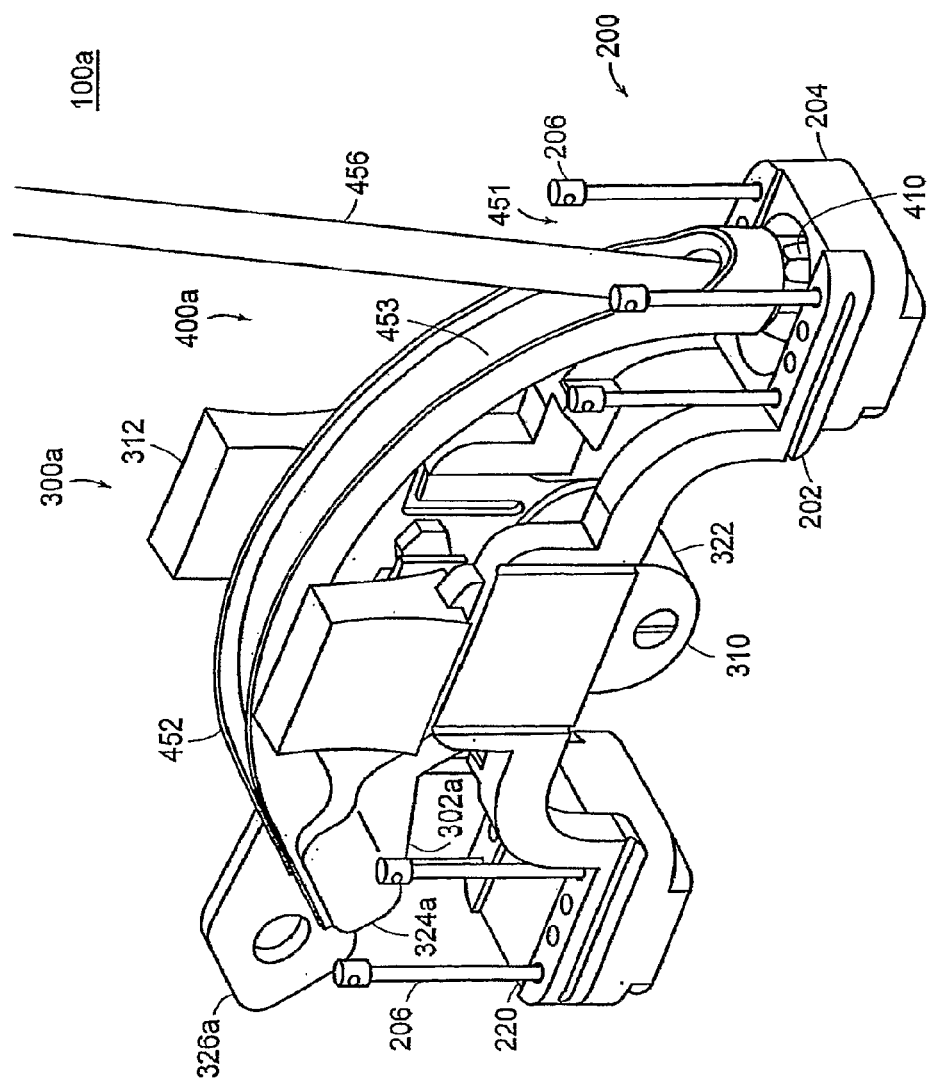
FIG. 18A is a perspective view of drilling apparatus according to yet another aspect of the present invention.
Figure 18B:
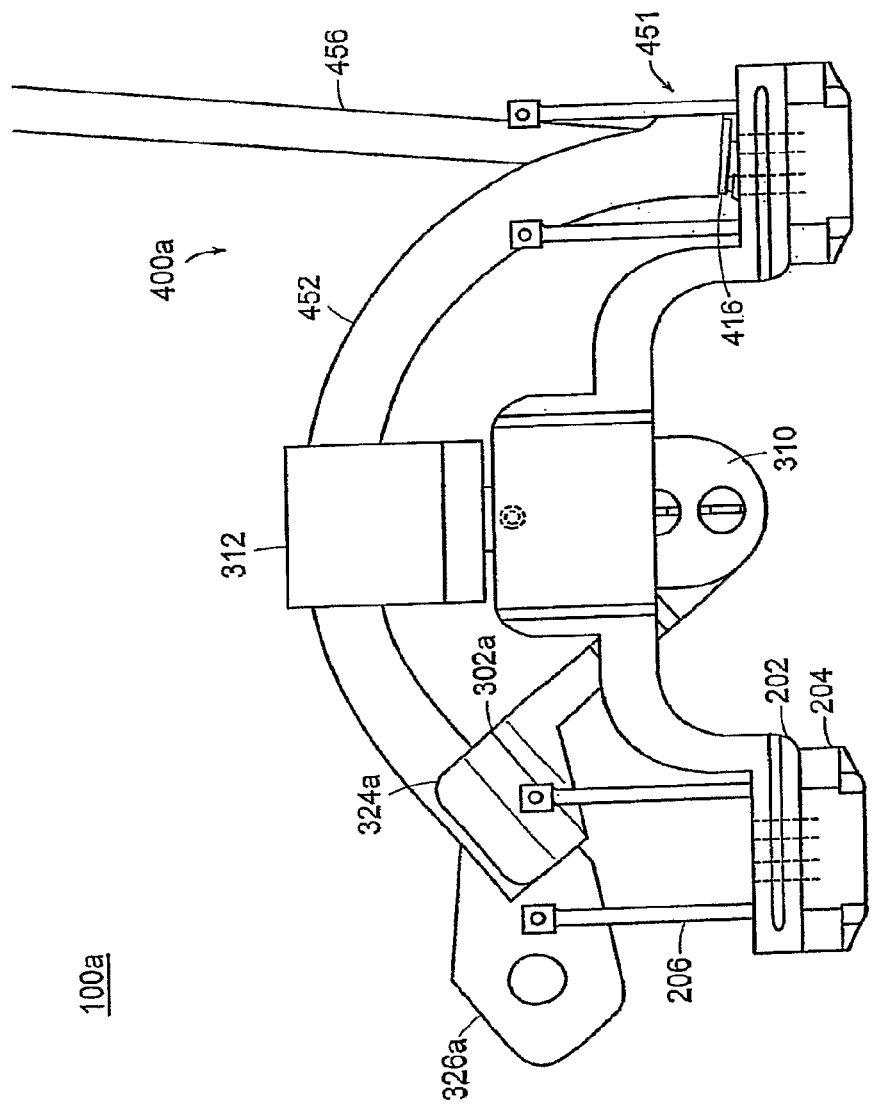
FIG. 18B is side view of the drilling apparatus of FIG. 18A.
Figure 18C:
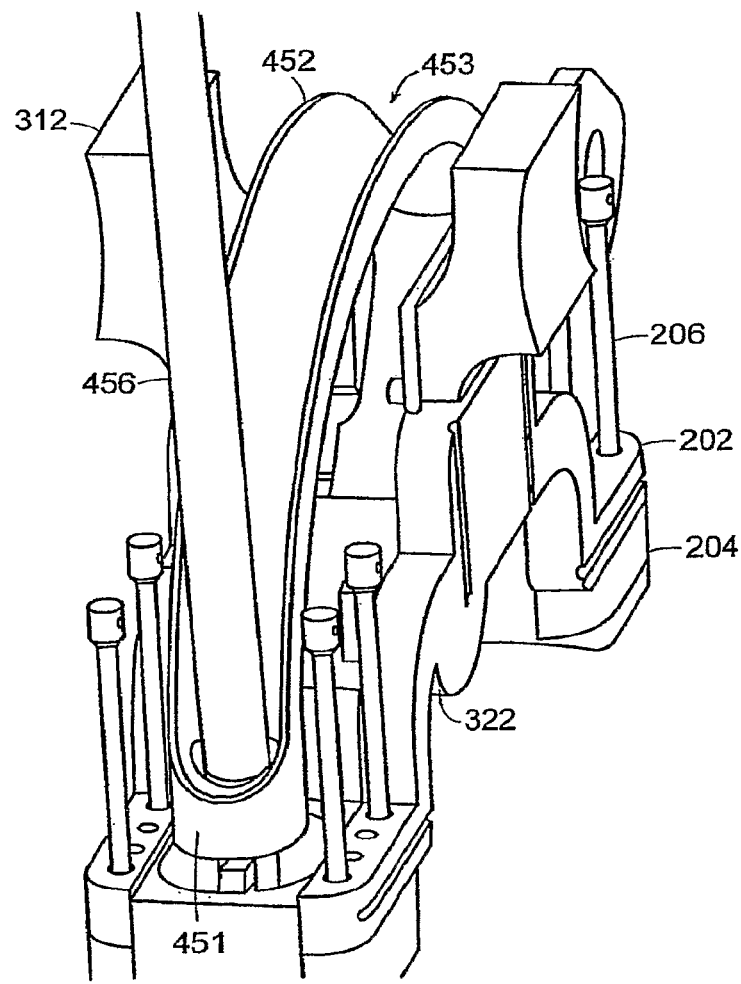
FIG. 18C is another perspective view from a different perspective of the drilling apparatus of FIG. 18A.

Referring now to FIGS. 18A-C there are shown various views of a drilling apparatus 100a according to yet another aspect of the present invention that is generally comprised of a platform assembly 200, a pivot arm assembly 300a and a drill assembly 400a. Reference shall be made to FIGS. 1-9 and the discussion related thereto for features and functions in common with the above-described drilling apparatus 100 shown thereon and not more particularly provided in the following discussion or shown in FIGS. 18A-C. Reference also shall be made to FIGS. 1-9 and the discussion related thereto for details concerning the removably attachment of the pivot arm 300a to the platform assembly 200 and the removable securing of the platform assembly 200 to the bone or bony structure.

The pivot arm assembly 302a includes a radial arm or pivot arm 302a, a pivot pin bracket 304 and a pivot pin 306. The pivot pin bracket 304 includes side plates 310 and finger pads 312 that are secured to the side plates, where the pivot pin extends between the side plates. The pivot pin 306 is received within an aperture 320 in the pivot arm 302a such that the pivot arm can rotate about a pivot axis 321. The pivot arm 302a is configure and arranged so as to include a mating portion 324a that is distal from the end 322 of the pivot arm that is mounted upon the pivot pin. In further embodiments, the pivot arm includes a finger grip 326a. Reference shall be made to the foregoing discussion for FIGS. 1-9 for further details of the pivot pin bracket 304, the pivot pin 306, and certain features of the pivot arm 302a not described further below. Reference also shall be made to the discussion above for the pivot arm 302 and the finger grip 326 for further details regarding the construction other characteristics for the pivot arm 302a and finger grip 326 features not expressly described below or shown in FIGS. 18A-C.

The drill assembly includes a curved or arcuate member 452, a drive cable 456, a drill bit 410 or burr, a drive adapter 414 and a distal drive cable bearing 416. Reference shall be made to the foregoing discussion for FIGS. 1-9 for further details of the drill bit 410, the drive adapter 414 and the distal drive cable bearing 416 not otherwise provided below or shown on FIGS. 18A-C. Reference also shall be made to the discussion above for the drive cable 408 for further details regarding the construction, width and other features not expressly described below.

As indicated herein any one of a number of motors 20 or motor drive assemblies as is known in the art having sufficient power (e.g., torque) and rotational speed are coupled to the drive adapter 414 including but not limited to the Micro100 (Linvatech/Hall Surgical 5053-009) or Blachmax (Anspach Blackmax-KT-0). The drive adapter 414 is a swage-type of fitting that is configured and arranged so it can be swaged upon one end of the drive cable 456. The drive adapter 414 also is configured and arranged so as to provide an input end arrangement that can be mechanically coupled to the output end of a variety of motors or motor drive assemblies or drills including those identified herein.

The pivot arm mating portion 324a is secured to a portion of the drill assembly curved or arcuate member 452 using any of a number of techniques known to those skilled in the art that are appropriate for the use and materials used in the construction of these features. In a specific embodiment, the arcuate member 452 is removably secured to the pivot arm-mating portion 324*a* (e.g., mechanical fasteners, adhesives) and in other embodiment the arcuate member is secured to the pivot arm-mating portion (e.g., adhesives, soldering, brazing) so as to form an integral structure. In further embodiments, at least a segment or portion of the pivot arm-mating portion 324*a* is configured and arranged so as to complement the shape of the portion of the arcuate member 452 being received therein. For example and as illustrated in FIGS. 18A-B, the arcuate member 324 also has a curved or arcuate cross-section. Thus, the pivot arm mating portion 324*a* is configured so as to receive therein a curved member having a curved or arcuate cross section. This shall not be considered limiting as the arcuate member 452 can be configured and arranged so as to have any of a number of external cross-sectional shapes.

As indicated above, the arcuate member 452 forms a curved structure that is attached to the pivot arm 302*a* as herein described and which thus swings around the pivot point or pivot axis 321. In use, the drill bit 410 rotates about its axis while this axis is held tangent to and swept along an arc of constant radius as defined by the distance between the mating portion 324*a* of the pivot arm 302*a* and the pivot axis 321. This movement results in or yields a toroidal hole.

The arcuate member 452 is curved to a predetermined radius of curvature so that the centerline thereof is a set distance from the pivot axis 321 of the pivot arm 302*a*. In further embodiments, the arcuate member 452 is a tubular like member having a portion of the tubular structure removed so the arcuate member 452 includes a dished area or depressed region 453 in which is received the drive cable 456 as hereinafter described. In an illustrative embodiment, the dished area or depressed region 453 is generally curved or circular in cross-section as more clearly illustrated in FIGS. 18 A, C. This, however, shall not be limiting as other geometric shapes are within the scope of the present invention that do not unduly impair the rotational capability of the drive cable 456 when received in the depressed region 453. In further embodiments, the dished area or depressed region 453 of the arcuate member 452 is sized and arranged so as to be capable of removably receiving therein the drive cable 456 and, more particularly so external surfaces of the drive cable are within an envelope or boundary defined by the depressed region 453 of the arcuate member.

The distal end 451 of the arcuate member 452 provides a structure in which the distal distal cable bearing 416 can be secured therein using any of a number of techniques known to those skilled in the art that is appropriate for the materials comprising these elements or features. In exemplary embodiments, the distal cable bearing 416 is secured within the arcuate member distal end 451 by brazing or soldering. Such a structure also provides a fixed point of attachment for the drive cable 456 such that that end of the drive cable and the drill bit 410 moves with the rotation of the arcuate member about the pivot axis 321. In more particular embodiments, the distal drive cable bearing 416 is secured within the arcuate member 452 such that the outer edge of the outer race of the bearing lies in a radial plane from the pivot point, whereby the axis of the drill bit 410 or burr is arranged so as to be tangent to the centerline of the arc of the arcuate member.

When drilling of an aperture or hole in the bone or bony structure is desired, the surgeon or medical personnel applies a force to the finger portion 326*a* so as to cause the arcuate member 452 to rotate about the pivot axis 321 and so as to cause the distal end 451 of the arcuate member to also rotate about the pivot axis. As the arcuate member distal end 451 rotates through the platform assembly 200, the drive cable 456 also is drawn along with the distal end and also is received in the depressed region 453 of the arcuate member (e.g., as the cable passes below the platform assembly 200). In this way, the rotating drive cable 456 is caused to lie within the depressed region 453 while the drive cable 456 is disposed within the bone or bony structure as the channel or aperture is being formed in the bone or bony structure as hereinafter described.

The arcuate member 452 according to this aspect of the present invention minimizes stress on the drive cable and reduces the amount of access required by the surgeon to perform the surgical procedure. The arrangement, however, also yields an apparatus that advantageously creates a mechanism that allows tissue, muscle, blood vessels (e.g., aorta) and nerves to pass under and around the platform assembly 200 and also to localize the drilling elements of the drill assembly 400*a* within the structure of the platform assembly. In addition, the pivot arm assembly 300*a* in combination with the platform assembly 200 provides a mechanism to control the radial movement radius or motion of the drilling elements of the drill assembly 400*a* from their insertion into the bone or bony structure as well as the retraction from the bone or bony structure such that the drilling elements traverse a specific radius of curvature during such insertion and retraction. In this way, the drilling apparatus 100*a* according to this aspect of the present invention also controls the maximum depth within the bone or bony structure the drilling elements can attain during use. Thus, and in contrast to conventional techniques, devices and instrumentalities, the drilling apparatus 100*a* of the present invention provides a mechanism that protects tissues, blood vessels and nerves from damage while the drilling elements of the drill assembly 400*a* are being inserted into and withdrawn from the bone or bony structure as well as assuring that the drilling elements will follow a generally fixed path such that the drilling elements do not come into contact with nor damage the tissues, blood vessels and nerves proximal to and surrounding the bone or bony structure while the hole or recess is being formed in the bone or bony structure. Consequently, the drilling apparatus 100*a* of the present invention minimizes the potential for damage without having to rely solely on the dexterity or skill of the surgeon as is done with conventional techniques and devices.

In general, the drilling path follows a desired path through the adjacent vertebrae or bony segments because the drilling apparatus, in particular the frame assembly thereof, is maintained in fixed relation with respect to the adjacent vertebral bodies or bony segments. However, the physical structure of the bony segments or the adjacent vertebral bodies in some cases creates a configuration in which the drilling assembly needs to be adapted to suit the particulars of the physical structure (e.g., the surface of the sacrum is at an angle with respect to the surface of the L-5 vertebrae).

Figure 21A:
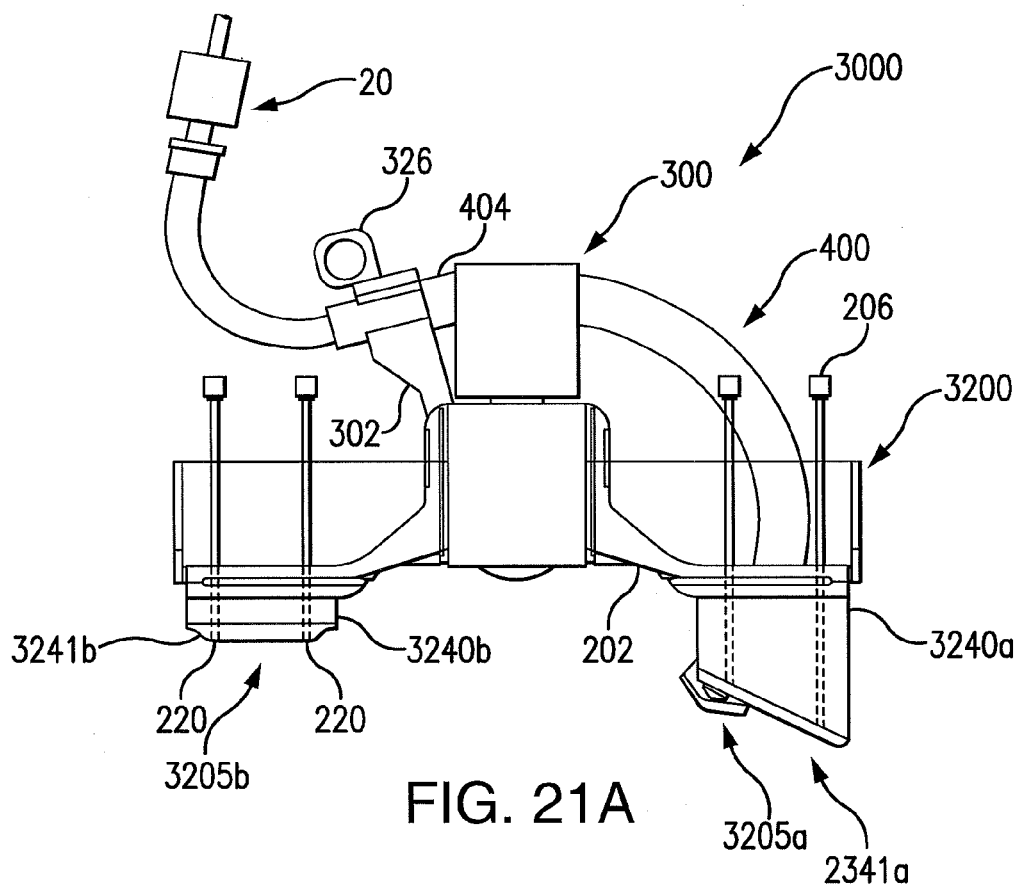
FIGS. 21A,B are side views of a drilling apparatus according to another aspect of the present invention where FIG. 21B includes a partial cutaway.
Figure 21B:
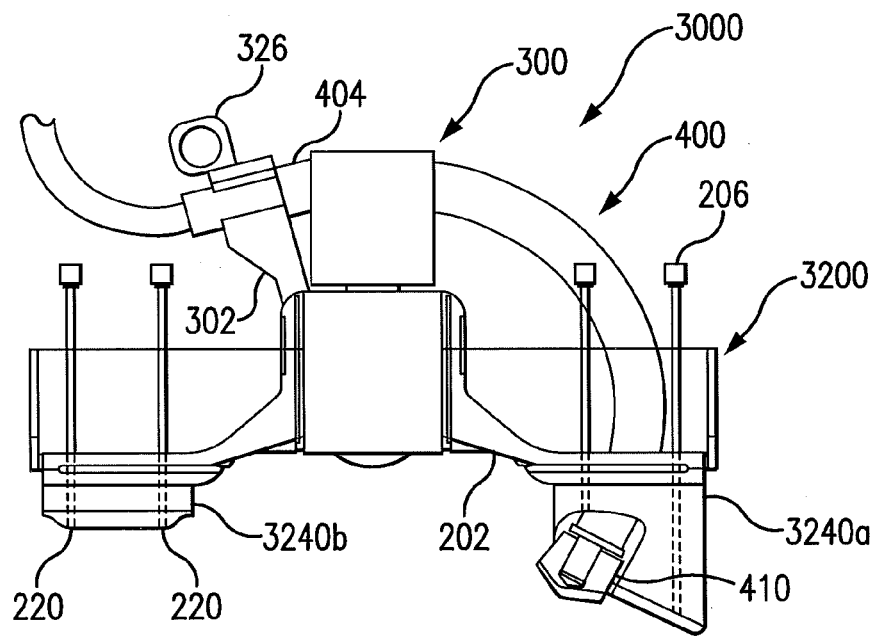
FIG. 21C is a perspective view of a lower portion of a spine including the sacrum on which is mounted a drilling apparatus of FIGS. 21A,B.
Figure 21C:
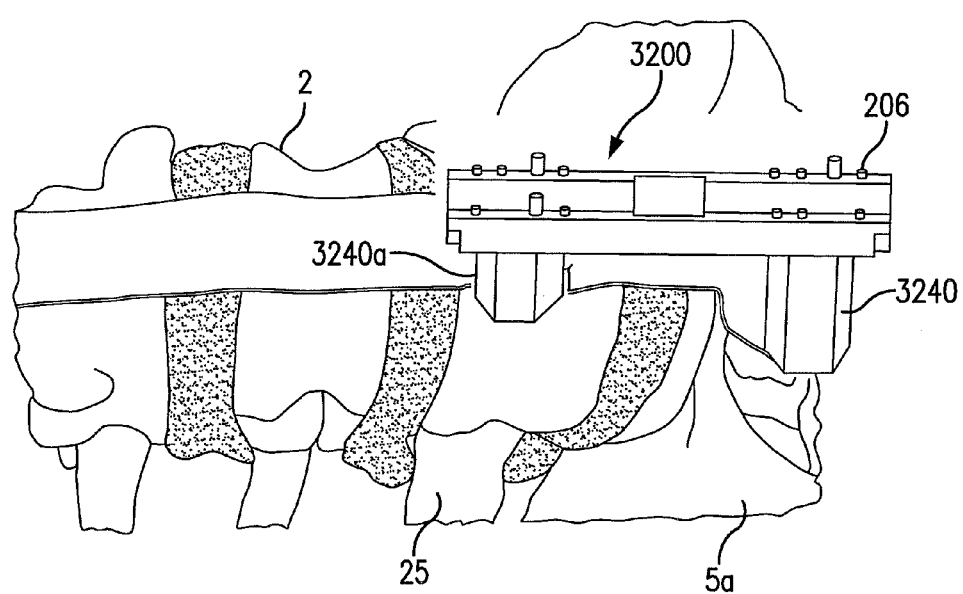
Figure 23A:
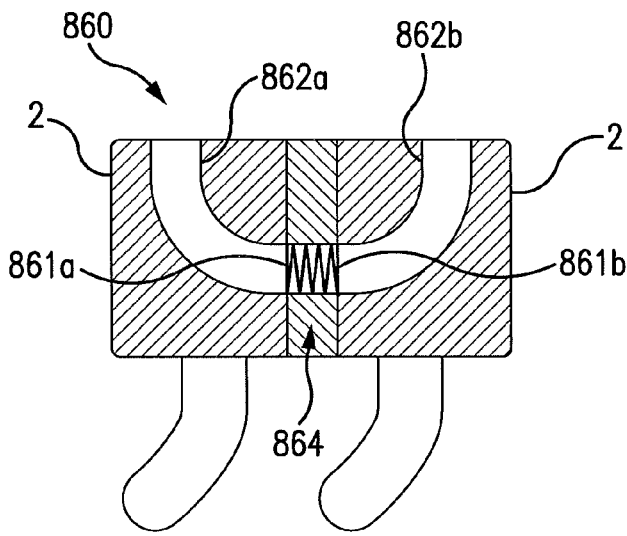
FIG. 23A is a cross-sectional side view that illustrates implanting or attaching a compressible implant device of the present invention in the through apertures and across the adjacent vertebrae.
Figure 23B:
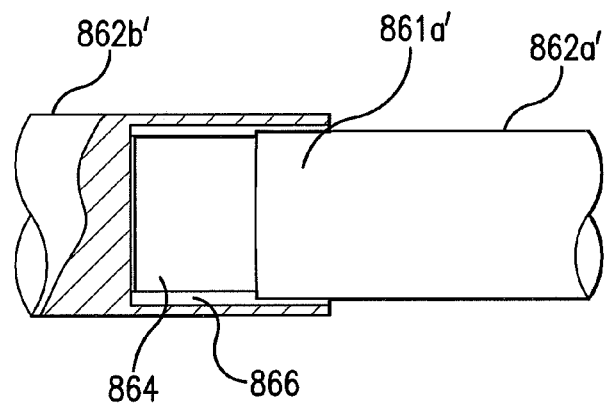
FIGS. 23B-C are illustrations of embodiments of the compressive segment for a compressible implant device of the present invention.
Figure 23C:
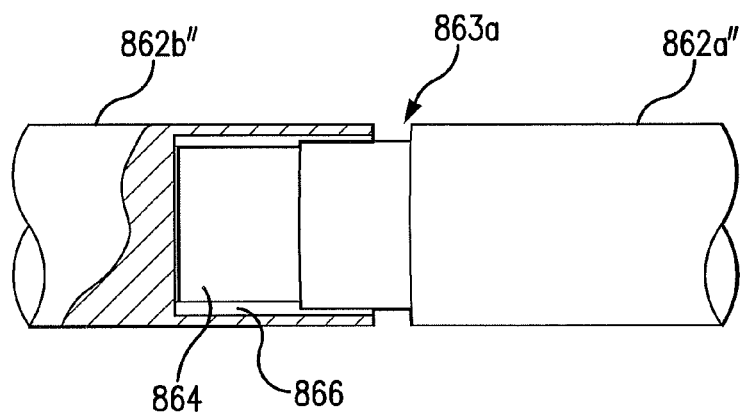

Referring now to FIGS. 21A-B there is shown a side view of a drilling apparatus 3000 according to another aspect of the present invention and in FIG. 23C there is shown a perspective view that illustrates the frame assembly 3200 thereof being disposed upon adjacent vertebral bodies 2. Such a drilling apparatus 3000 includes a platform assembly 3200, a pivot arm assembly 300 and a drill assembly 400. It should be recognized that the frame assembly 3200 is illustrative and that it is contemplated that any of the other frame assemblies herein described are adaptable so as to embody the specifics of the platform assembly of this aspect of the present invention. Such a drilling apparatus 3000 is particularly adaptable to accommodate the physical structure and so as to allow channels to be formed in adjacent bony segments or adjacent vertebral bodies while minimizing the risk of injury or damage to nearby nerves, tissues, muscles and/or blood vessels. Reference shall be made to FIGS. 1-9 and 17-18 and the discussion related thereto for features and functions in common with the below-described drilling apparatus 3000 shown thereon and not more particularly provided in the following discussion or shown in FIGS. 21A-B.

The platform assembly 3200 includes a frame member 202 and a plurality of path guard members 3204a,b and a mechanism for securing the frame to the bone or bony structure. As with the drilling apparatus illustrated in FIG. 1, the securing mechanism comprises a plurality of nail members 206 that each pass respectively through each of the first path guard members 3204a,b so as to be disposed in the bone or bony structure as herein described. In further embodiments, and as hereinafter described, the platform assembly 3200 can further include a second path guard 205, in cases where the drilling apparatus 3000 is used to form a groove or recess in an outer surface of the bone or bony structure thereby providing a protective structure between the moving and rotating drill bit 410 and the tissues or other structures or features of the mammalian body (e.g., nerves, blood vessels) that are proximal the bone or bony structure outer surface.

The frame member 202 and the first guard members 3204a,b are configured and arranged so as to form an essentially rigid structure and framework to which the drill assembly 300 is removable attached and at least one and more particularly two through passages 3205a,b. Each of the through passages 3205a,b are configured and arranged so as to allow the outer tube member of the drill assembly 300 to pass there through as drill bit 410 is being is being rotated or pivoted about the pivot point. The frame member 202 is composed of any one of number of materials known to those skilled in the art that is appropriate for the intended use and the anticipated structural loads that can be imposed during use. In an exemplary embodiment, the frame member 202 is made from stainless steel such as a stainless steel bar stock.

The first path guard members 3204a,b are each configured and arranged so the frame assembly 3200 is maintained in a desired orientation with respect to the adjacent bony segments or adjacent vertebral bodies for formation of the channel. In particular embodiments, the bottom surface 3241a,b of each first path guard members is configured and arranged so as to correspond generally to the opposing surface of the adjacent bony segment or vertebrae. In an illustrative exemplary embodiment, a bottom surface 3241a for one first path guard member 3240a is formed at an angle with respect to a longitudinal axis of the first path guard member when the opposing surface is at an angle with respect to the desired orientation of the frame assembly (e.g., the angled surface of the sacrum) such as illustrated in FIG. 23C. In further embodiments, the length of each first path guard member is adjusted so as to compensate for differences in relative heights between the frame assembly attachment point of one adjacent bony segment or vertebral body and the frame assembly attachment point of the other adjacent bony segment or vertebral body. In an illustrative exemplary embodiment, one first path guard member 3240a is made longer than the other first path guard member 3240b so the frame 202 is maintained in a particular orientation with respect to the target are such as illustrated in FIG. 23C. In this way, the frame 202 is oriented so that the channel formed by the rotation of the drill bit 410 is along the desired path in the adjacent vertebrae.

The foregoing is illustrative of a couple techniques for maintaining the frame assembly 3200 at a desired orientation with respect to the adjacent bony segments or adjacent vertebral bodies. However, this shall not be construed as limiting as other techniques can be utilized to address the described angular and length as well as other differences that may arise because of the physical structure (e.g., adjusting for surfaces being at angles with respect to more that one axis).

The first path guard members 3204a,b are secured to the frame member 202 using any of a number of techniques known to those skilled in the art so that the through apertures 3205a,b in the first path guard members 3204a,b extend generally downwardly towards a bottom surface 3241a,b thereof. In further embodiments, particularly when a first path guard member 3240b has a different length than the other first path guard member 3240a as well as having a bottom surface 3241a that is at angle with respect to a longitudinal axis of the guard member, the through aperture 3205b may comprise an opening through a side of such a first path guard member 3204b or such an opening that extends through the side and into the bottom surface. These openings are generally established based on the geometry between the frame assembly 3200 when it is secured to the adjacent bony segments or adjacent vertebral bodies and the pivot point for forming the desired channel.

As indicated above, the though passage 3205a,b in each of the first path guard members 1204 are arranged so the outer tube member 402 and the drill bit 410 or burr of the drill assembly 300 are passed there through. In addition, each of the first path guard members 3204a,b are configured and arranged so as to include a plurality of through passages, one for each of the nail members. Reference shall be made to the foregoing discussion for the nail member through passages 220 of FIG. 1 for further detail and characteristics of these nail member through apertures.

The arrangement of the drilling apparatus 3000 yields an apparatus that advantageously creates a mechanism that allows tissue, muscle, blood vessels (e.g., aorta) and nerves to pass under and around the platform assembly 3200, to localize the drilling elements of the drill assembly 400 within the structure of the platform assembly and to provide a mechanism to compensate for any differences between the adjacent bony structure or adjacent vertebrae. In addition, the pivot arm assembly 300 in combination with the platform assembly 3200 provides a mechanism to control the radial movement radius or motion of the drilling elements of the drill assembly 400 from their insertion into the bone or bony structure as well as the refraction from the bone or bony structure such that the drilling elements traverse a specific radius of curvature during such insertion and retraction. In this way, the drilling apparatus 3200 according to this aspect of the present invention also controls the maximum depth within the bone or bony structure the drilling elements can attain during use. Thus, and in contrast to conventional techniques, devices and instrumentalities, the drilling apparatus 3200 of the present invention provides a mechanism that protects tissues, blood vessels and nerves from damage while the drilling elements of the drill assembly 400 are being inserted into and withdrawn from the bone or bony structure as well as assuring that the drilling elements will follow a generally fixed path such that the drilling elements do not come into contact with nor damage the tissues, blood vessels and nerves proximal to and surrounding the bone or bony structure while the hole or recess is being formed in the bone or bony structure. Consequently, the drilling apparatus 3200 of the present invention minimizes the potential for damage without having to rely solely on the dexterity or skill of the surgeon as is done with conventional techniques and devices.

Figure 10B:
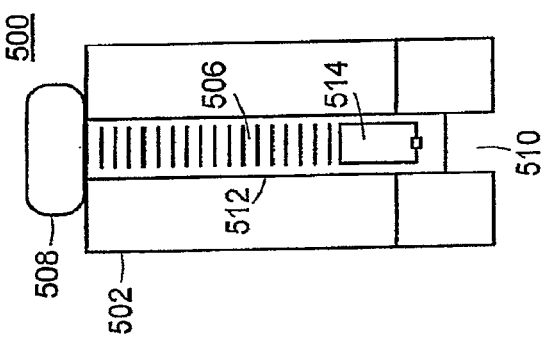
FIG. 10B is an end view of the nail removal tool.
Figure 10A:
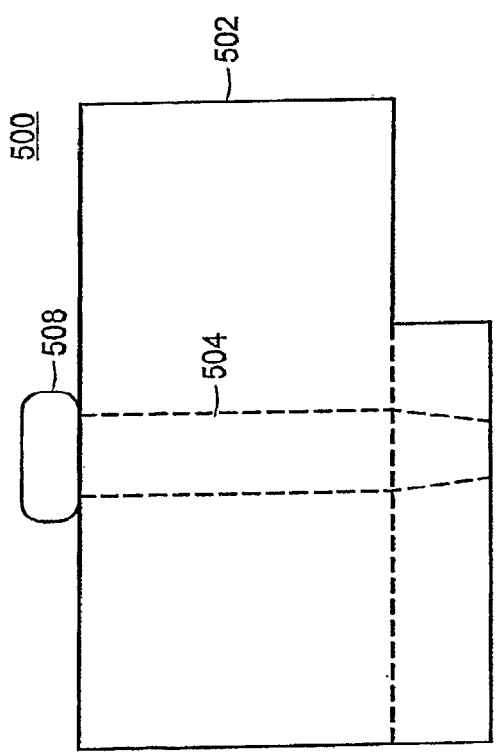
FIG. 10A is a side view of a nail removal tool according to one embodiment of the present invention.
Figure 11:
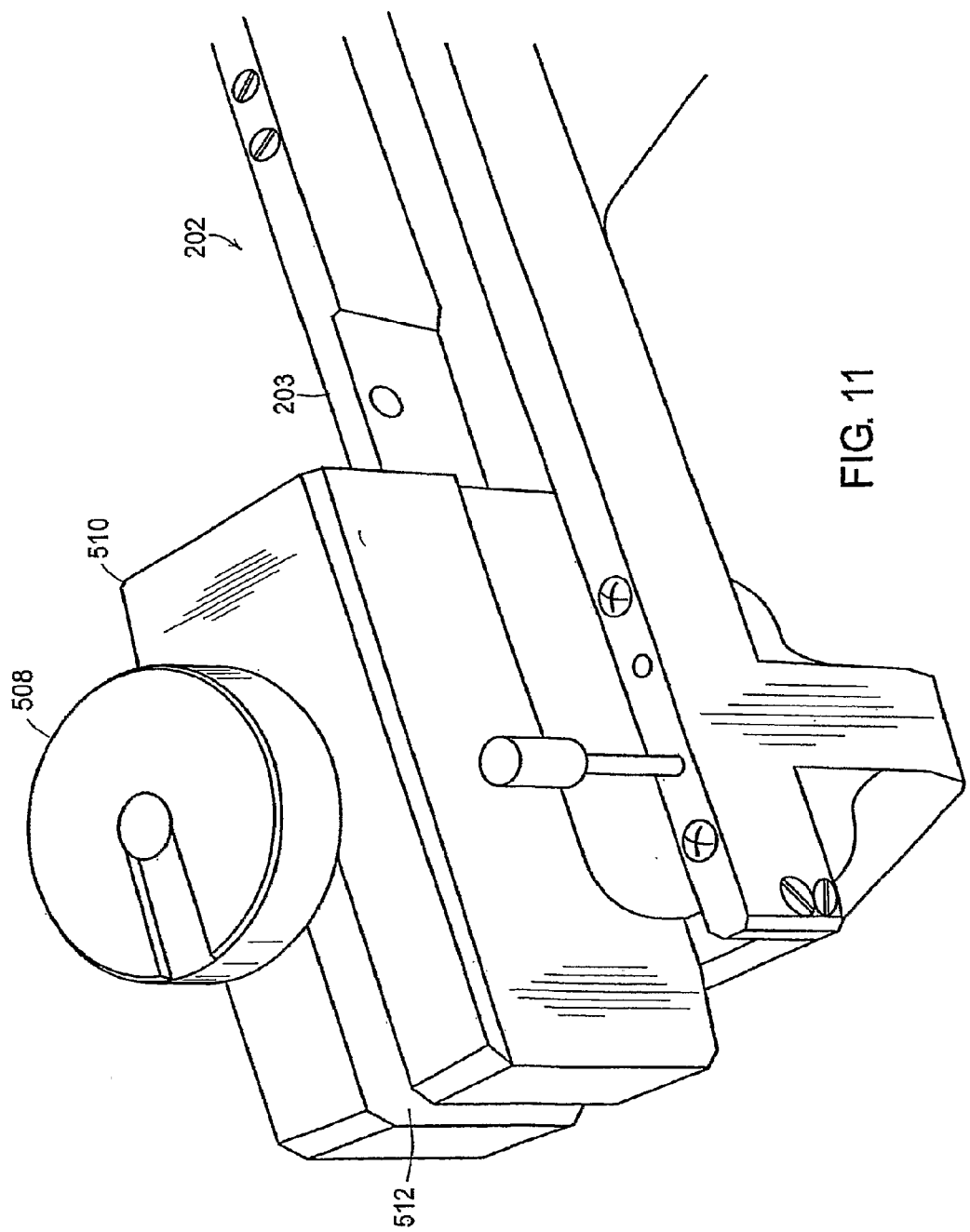
FIG. 11 is a perspective view of the nail removal tool mounted on the platform assembly of the drilling apparatus.

Upon completion of the procedure involving use of the drill assembly 100 of the present invention, and as described herein, the nail members 206 are acted upon so as to remove each of the nail members from the bone or bony structure or spine. This removal can be accomplished using any of a number of techniques or devices known those skilled in the art. In particular embodiments of the present invention, and with reference to FIGS. 10A,B, there is shown a side view and an end view respectively of a nail member removal device 500 according to the present invention. Reference also should be made to FIG. 11, which illustrates the removal technique using such a nail member removal device 500.

The nail member removal device 500 includes a block member 502 and a knurled screw member 506. The block member 502 includes a through passage that extends lengthwise in the block member so as to form a saddle structure that can straddle and slide along side rails 203 of the frame 202. In further embodiments, the block member 502 includes a slotted passage 512 that extends from a bottom surface to a top surface of the block member and extends partially lengthwise to a surface of the through aperture 504 or hole that is formed in the block member. The slotted passage 512 also is generally sized so to allow the block member to slide past the head portion 230 that is sticking up above the top surface 210a of the frame, more particularly the side rails thereof.

The threaded aperture 504 or hole is positioned within the block member 502 so that it can be centered over one of the head portions 230 of the nail members 206. In use, the nail members 206 are typically driven into the bone or bony structure such that a bottom surface of the head portion 230 is proud of or above the frame top surface 210a. As such a lower portion of the knurled screw member 506 is machined so as to include a side pocket 514 therein. The side pocket 514 is made in the screw member 506 so as to have sufficient depth (e.g., width) and length to accommodate the head portion coaxially therein. The bottom segment of the screw member 506 also includes a notch that extends generally radially to allow the nail member shaft portion 232 to be received therein and so as to be also coaxial with the screw member.

In particular embodiments, when the screw member 506 is rotated in one direction (e.g., clockwise) the side pocket 514 can be aligned with the slotted through passage 512 and thus be ready to receive therein a nail member head portion 230. The block member 502 is slide along the frame side rail 203 until the head portion is contained within the side pocket 514. After the head portion is disposed in the side pocket, the screw is rotated in the opposite direction (e.g., counterclockwise) thereby causing the screw to rotate in an upwardly direction drawing the notched bottom surface of the side pocket into contact with the bottom surface of the head portion. When the notched bottom surface of the side pocket 514 engages the bottom surface of the head portion, continued rotation of the screw member 506 also causes the head portion to be moved upwardly. In this way, the pointed end of the shaft portion is withdrawn from the bone or bony structure.

In more particular embodiments, the block member 502 and the slotted passage 512 therein are formed such that a portion of the block member is disposed over an end portion of the end rail of the frame 203. This establishes a configuration whereby the pulling load is applied between two support points, thereby minimizing the potential for tipping of the nail member removal device 500 due to unbalanced force couples.

Figure 12:
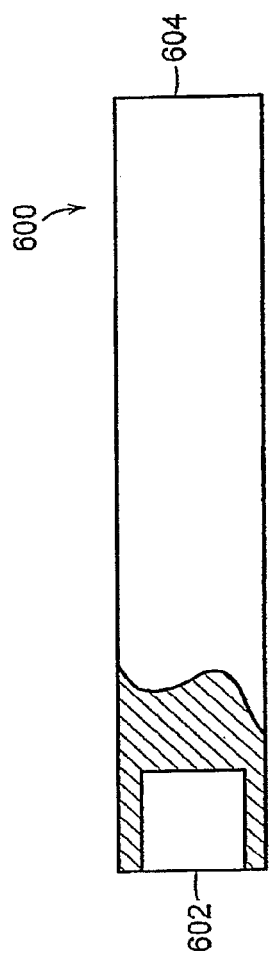
FIG. 12 is a side view with a partial cut away of a nail drive tool according to an embodiment of the present invention.

As indicated herein, prior to use of the drilling capabilities of the drilling assembly 100 of the present invention, the nail members are driven into contact with the constricted regions of the first path guards 204 and into engagement with the bone or bony structure or spine. This driving of the nail members can be accomplished using any of a number of techniques or devices known those skilled in the art. In particular embodiments of the present invention, and with reference to FIG. 12 there is shown a side view with a partial cut-away of a nail member drive tool 600 according to the present invention.

The drive tool 600 is a generally cylindrical member having a blind hole 602 or aperture in one end thereof. The blind hole 602 is sized so as to receive therein a head portion 230 of a nail member 206. The drive tool 600 is constructed so that an impact load, such as that imparted by a hammer, at the opposite end 604 thereof drives the nail member 206 disposed in the blind hole 602. In further embodiments, the blind hole 602 also is sized so as to generally prevent the tool from slipping off the head portion. In yet further embodiments, the depth of the blind hole 602 is set so that the bottom surface of the head portion 230 remains a predetermined distance above the frame top surface 210a so as to allow the head portion to be later received in the side pocket of the screw member 506 of the nail member removal device 500.

As indicated herein the drilling apparatus 100 of the present invention is adaptable for use for forming recesses or holes in bones, bony structures or the spine of a mammalian body. The following describes the use of the drilling apparatus in connection with two different techniques (i.e., anterior approach and medial approach) for forming a recess or an aperture in adjacent vertebral bodies of a spine. Although the following discussion specifically refers to the drilling apparatus 100 shown in FIG. 1 it shall be understood that the below described techniques can be used in conjunction with the drilling apparatus 1000, 100a shown in FIGS. 17-18 as well as other embodiments of such apparatuses 100, 100a, 1000. Referring now to FIGS. 13A-L there is shown a series of views illustrating the process for the anterior approach. Reference shall also be made to FIGS. 1-11 and 17-18 and the discussion related thereto for features and functions not provided in the following discussion.

Figure 13A:
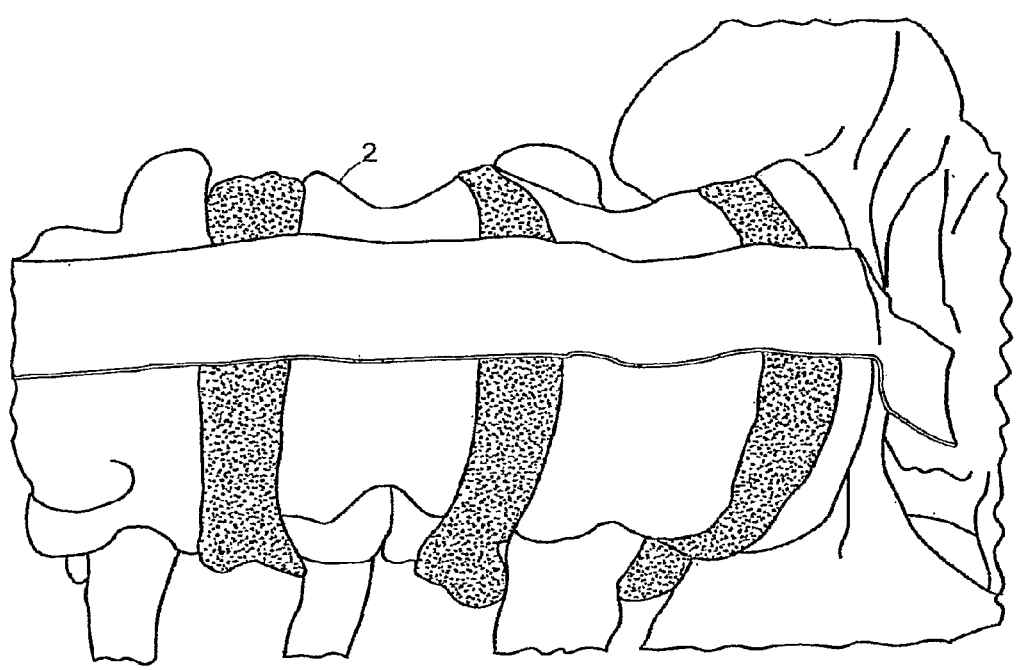
FIGS. 13A-L are illustrations of the process for forming a recess in adjacent vertebral bodies.
Figure 13B:
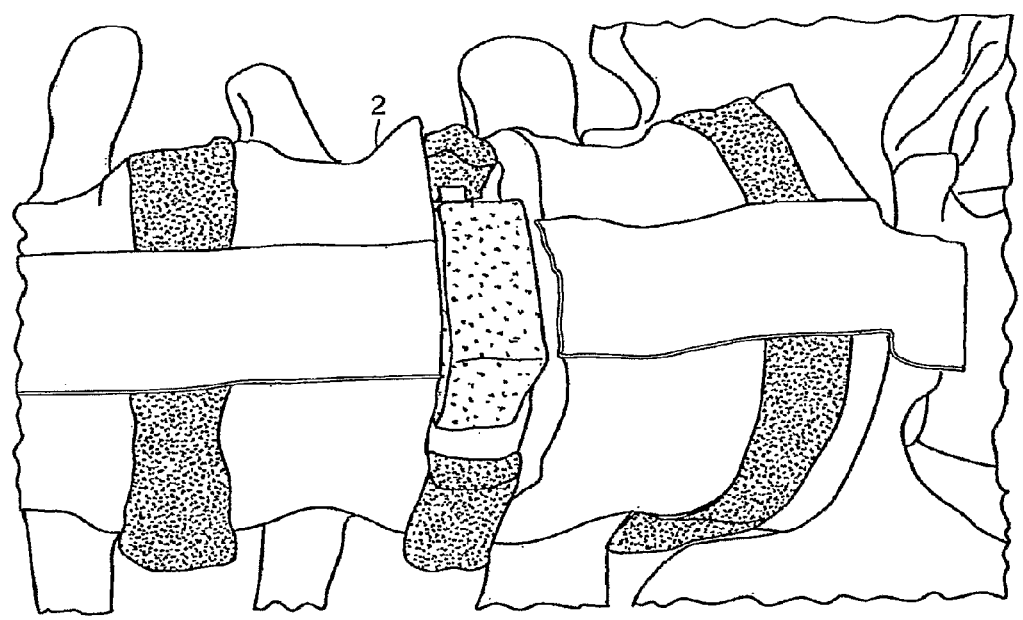
Figure 13C:
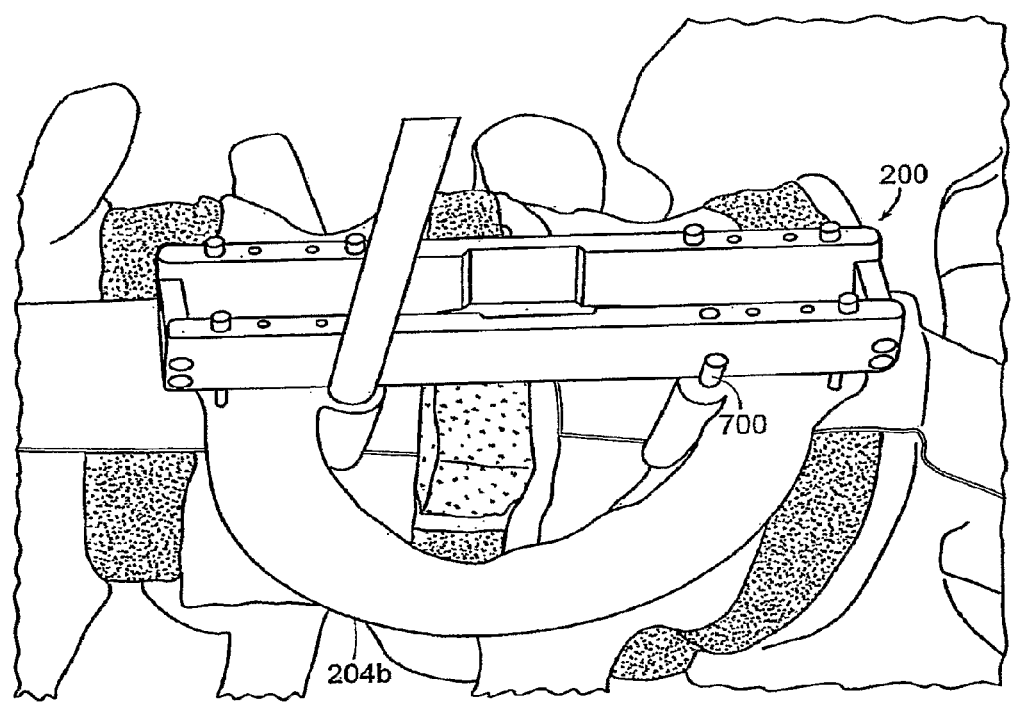
Figure 13D:
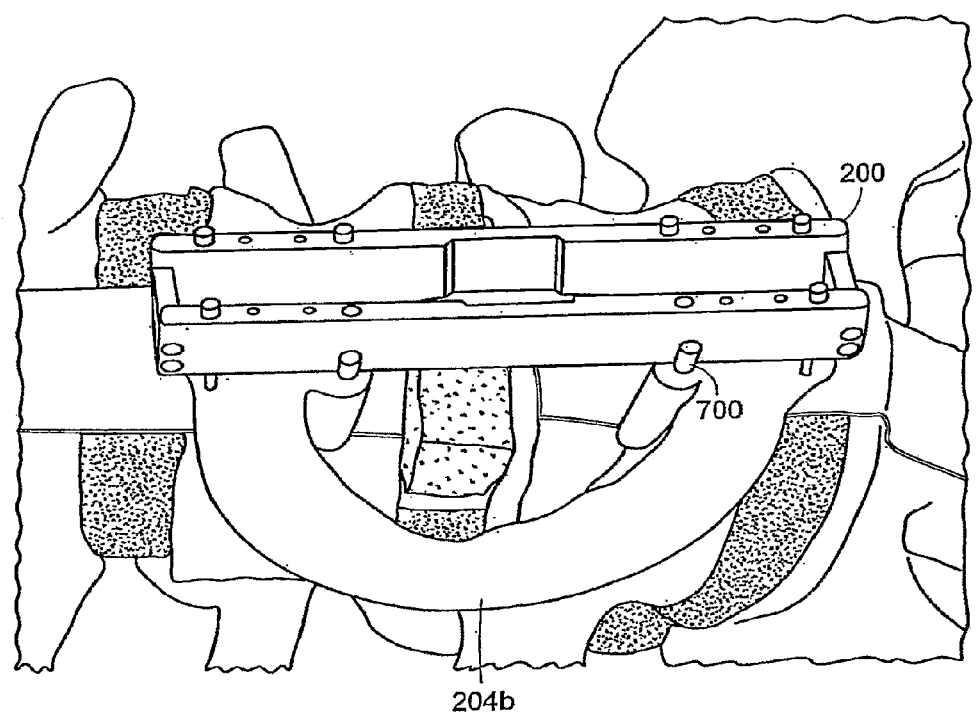
Figure 13E:
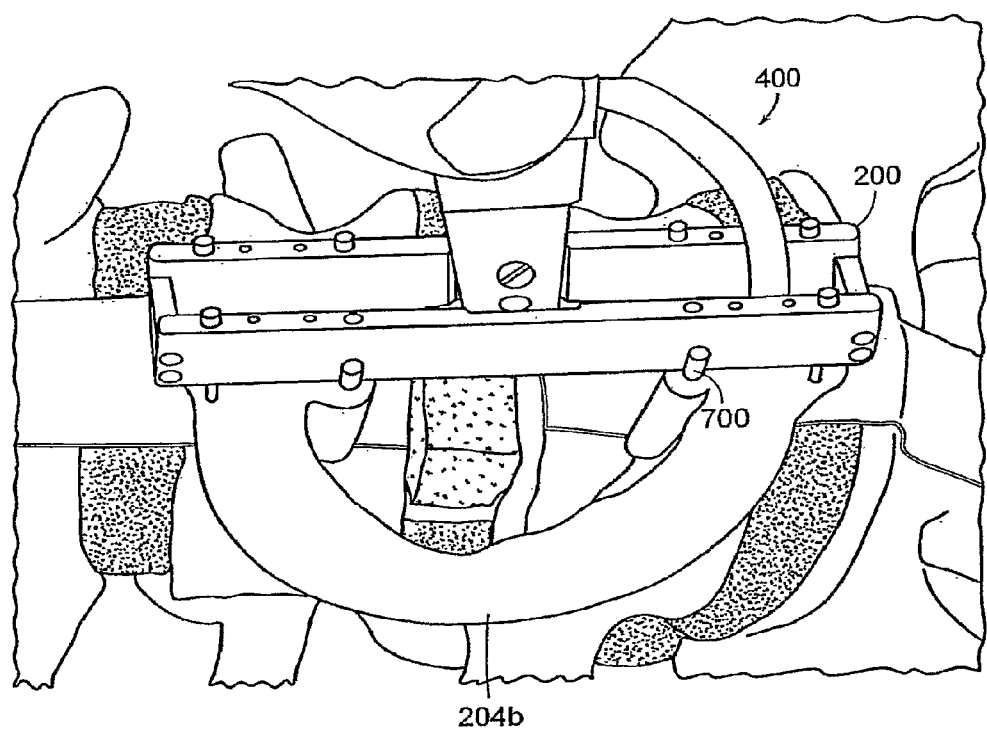
Figure 13F:
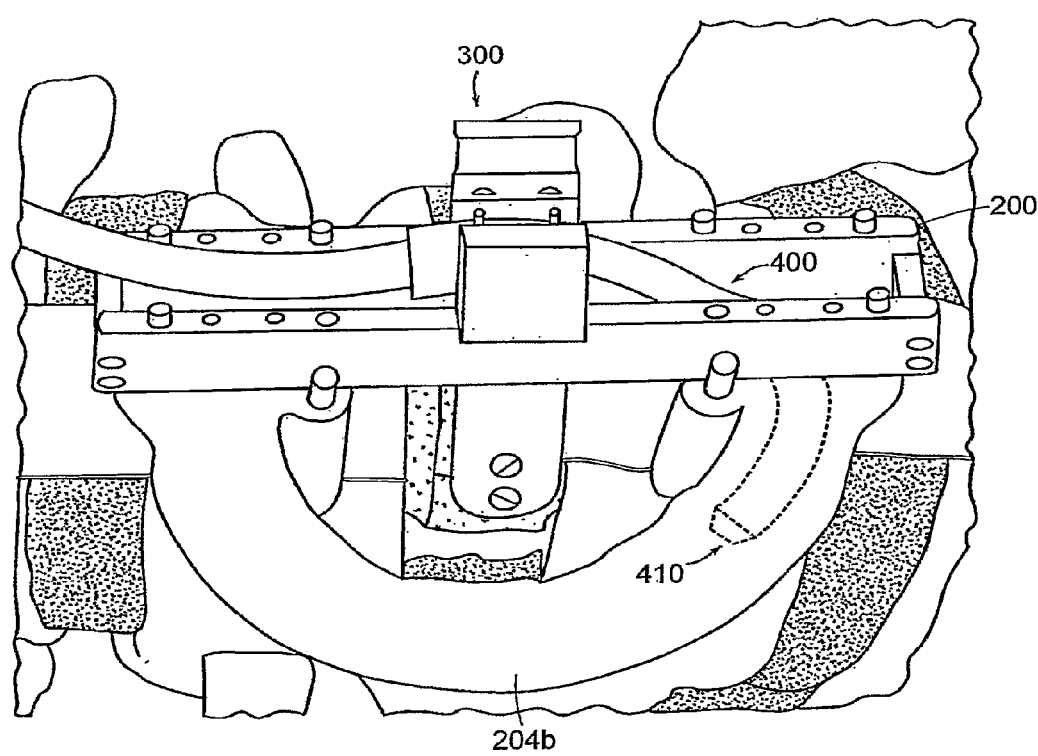

The area of concern is exposed by a surgeon using one of a transperitoneal or retroperitoneal approach, as shown in FIG. 13A and a discetomy is performed at the level to be instrumented and immobilized. After placing a support (e.g., a femoral ring allograft) in the disc space, lateral stabilization is performed (see FIG. 13B).

The drilling apparatus frame 202 is aligned such that it is vertical in an anteroposterior orientation and placed as far lateral as possible on the anterolateral aspect of the vertebrae across the operative level. Temporary placement pins 700 are driven into the vertebral cortex to hold the frame 202 in place while creating the channel or recess. In addition, the present invention contemplates the addition of a second path guard 204b that extends between the first path guards 204. The second path guard 204b is arcuate or curved having a radius that generally corresponds to the path of the drill bit 410. The second path guide 204b also is configured so as to extend outwardly from the vertebral cortex so as to provide a barrier between the drill bit travel path and tissues, nerves and blood vessels proximal the site. The second path guard 204b is constructed of similar materials as the first path guards 204. See FIGS. 13D-E.

When the frame 202 is positioned in the intended fashion, the pivot arm assembly 300 is located and secured within the frame 202, thereby also securing the drill assembly 200 in the frame. See FIG. 13E. The drive motor 20 or drive motor assembly is then secured to the adapter 414. The pivot arm 302 is then positioned so the drill assembly/drill bit is in the starting position so the channel or recess can be cut. See FIG. 13F.

Figure 13G:
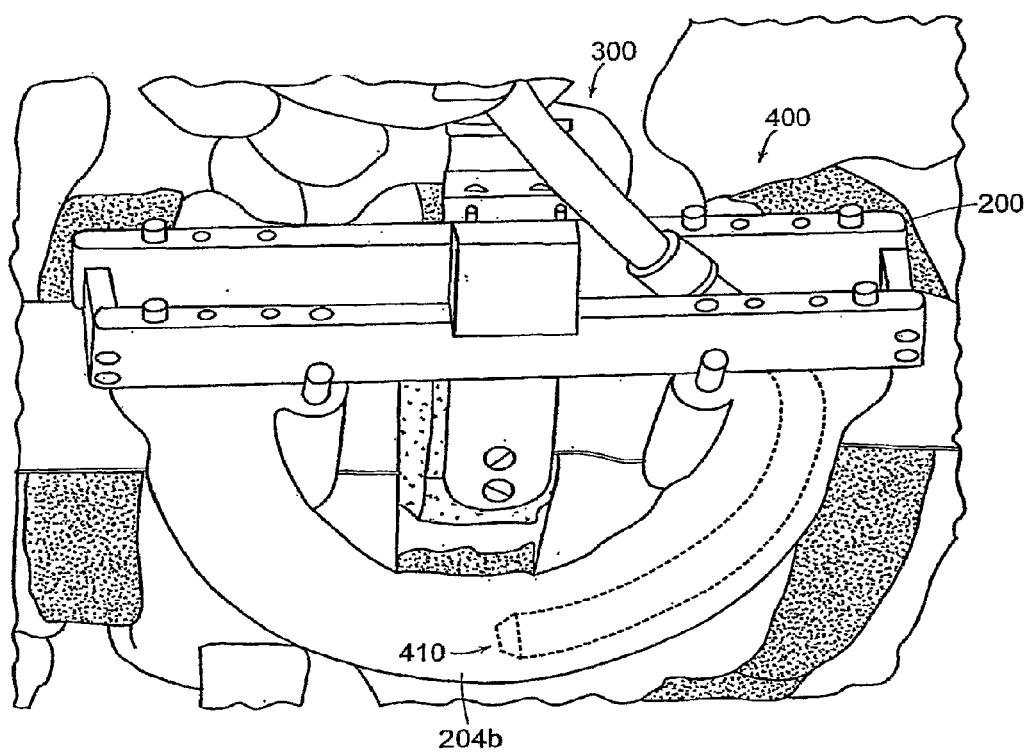
Figure 13H:
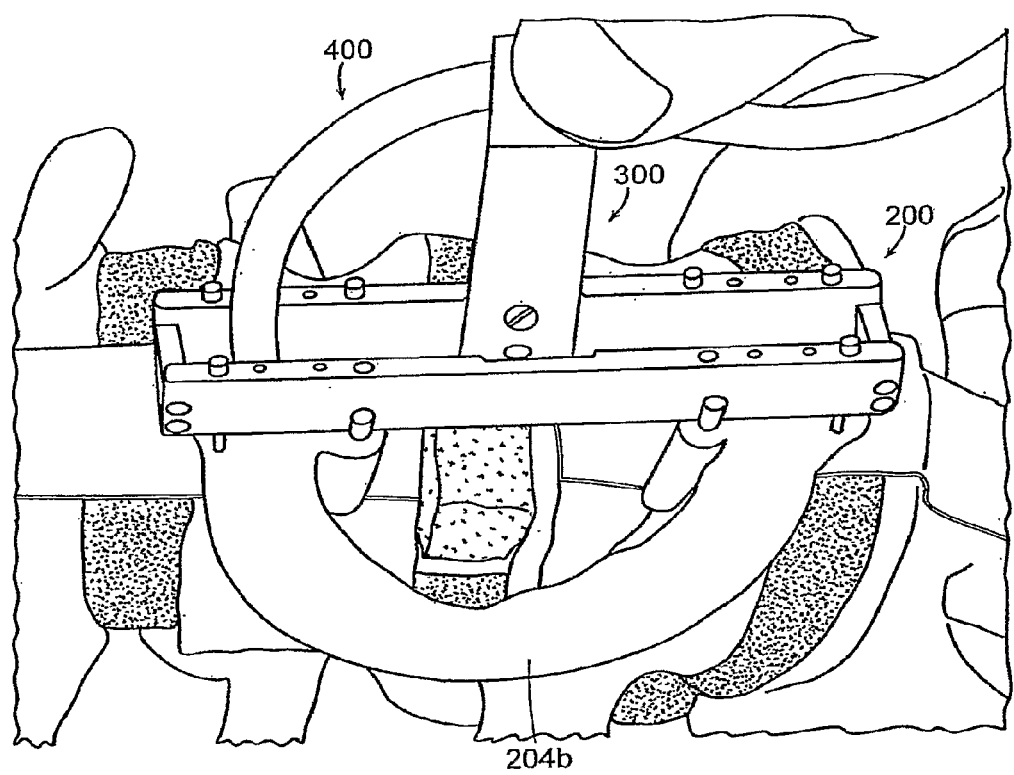
Figure 13I:
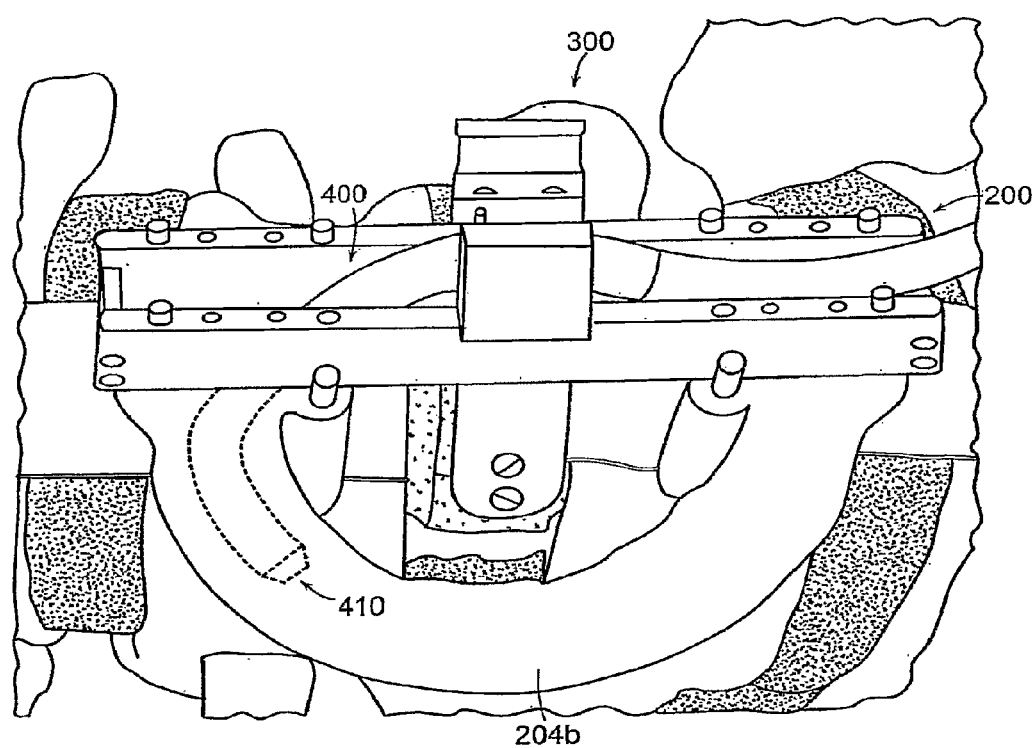
Figure 13J:
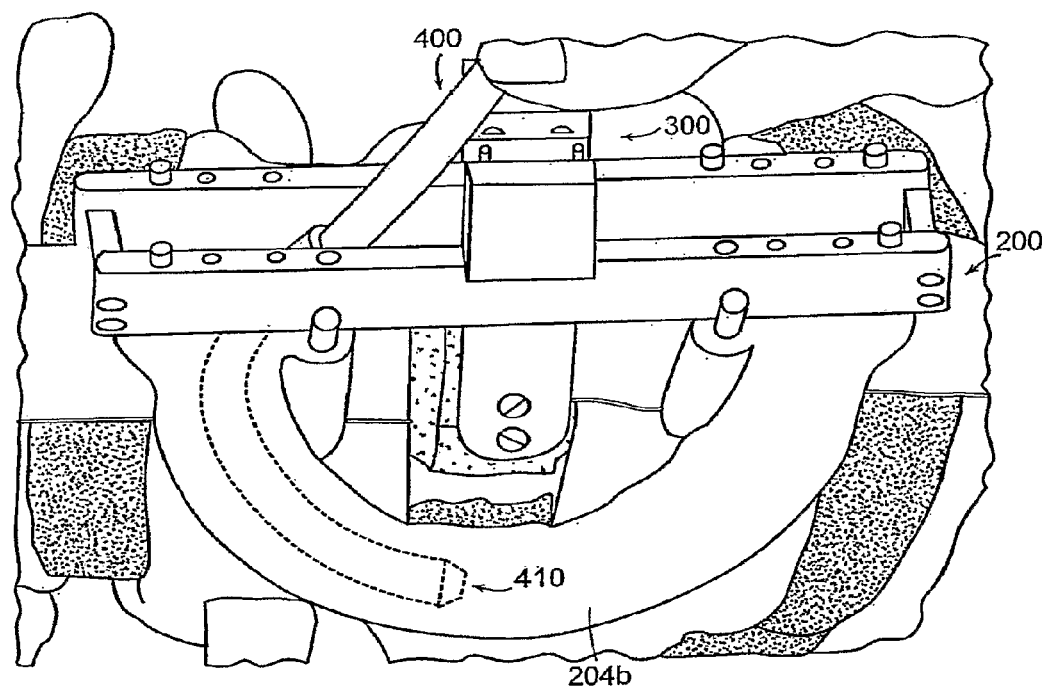
Figure 13K:
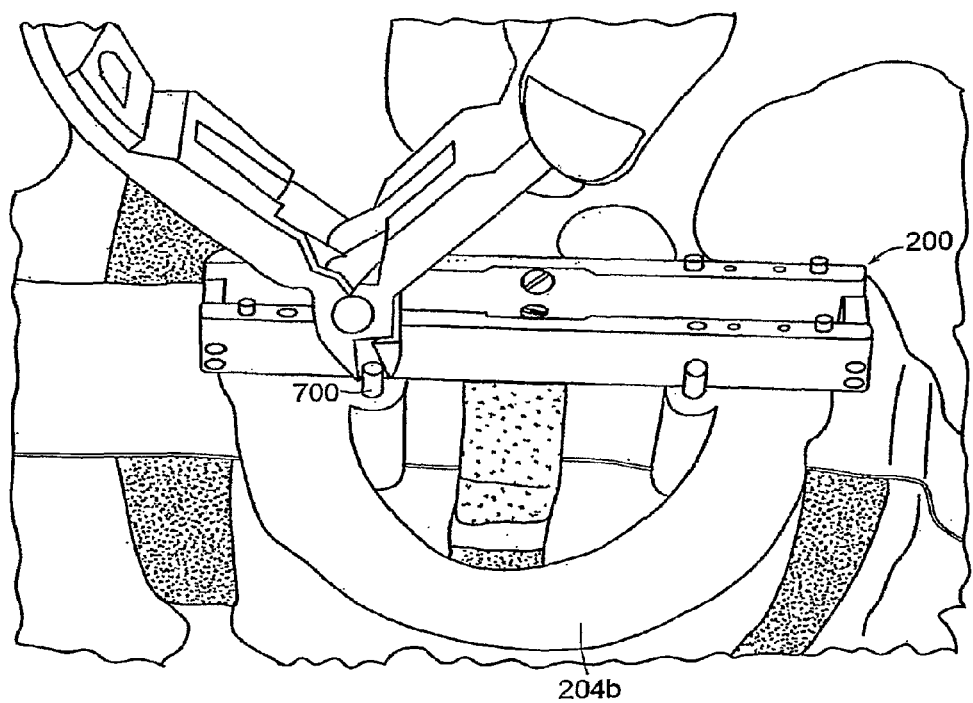
Figure 13L:
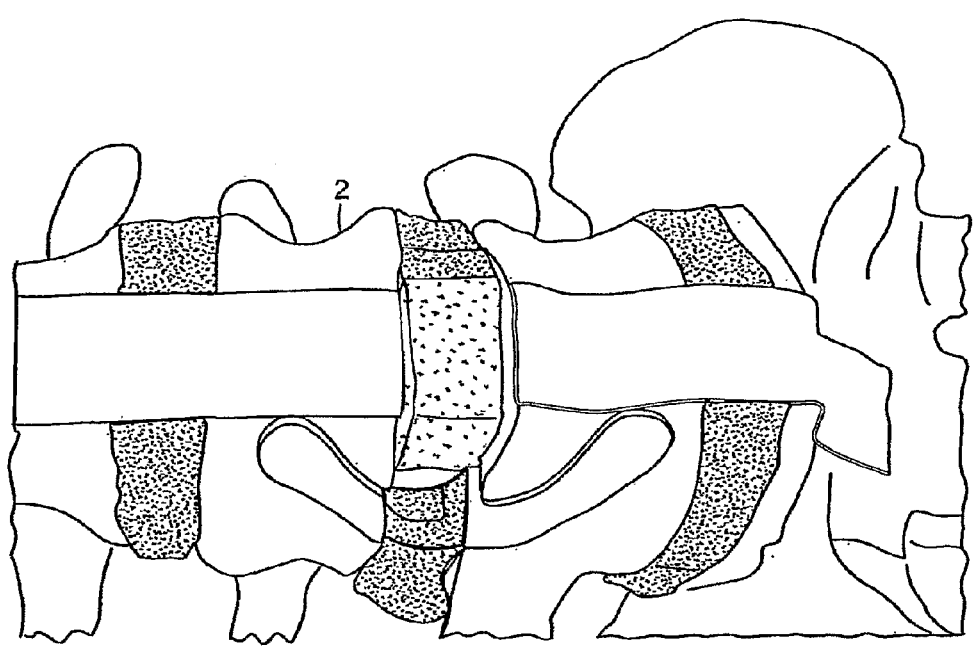

The drill motor 20 is started so as to cause the drill bit 410 to rotate at the desired speed and power, and the pivot arm 302 is rotated about the pivot point thereby causing the drill bit 410 to rotate in a predetermined direction in a downward, circular path as dictated by the frame and the pivot arm. The resulting cut should be made immediately adjacent to the lateral vertebral surface. This cut is complete when the drill bit 410 reaches the disc space as shown in FIG. 13G.

Once the first half of the channel is cut, and with the drive motor 20 turned off and/or disconnected from the adapter 414, the pivot arm is rotated in the opposite direction to return it to the starting position, where the pivot arm assembly 300 can be removed from the frame 202. After removing the pivot arm assembly 300 from the frame 202, the pivot arm assembly is flipped to the opposites side of the frame and reconnected to the frame. In this way, a matching channel can be cut into the other vertebra adjacent to the operative level. See FIG. 13H. As with the first cut, the drive motor 20 is turned on and the pivot arm rotated so the drill bit 410 follows a downward, circular path. After the second half of the channel has been cut, the pivot arm is returned to the starting position and the pivot arm assembly 300 is removed from the frame 202. See FIGS. 13I-J.

The temporary placement pins 700 are removed from the vertebral bodies and the frame 202 is removed from the operative site (see FIG. 13K) and a standard osteotome chisel can be used to remove any remaining bone from the channel edges so that the channel is open to receive or accept the curved rod.

Now with reference with FIGS. 14A-D there is shown the process for placing, positioning and attaching or implanting a curved rod 800, including those described in any of U.S. Pat. No. 6,607,530 and U.S. Ser. No. 10/019,265, the teachings of which are incorporated herein by reference. The curved rod 800 is positioned in the channel and secured to the vertebral bodies using interlocking screws 802, 804 that traverse the rod and penetrate the vertebra at an angle that will avoid sensitive neurologic structures. The screws hold the curved rod 800 in place and stabilize the motion segment to facilitate healing of the bone within the disc space.

Figure 14A:
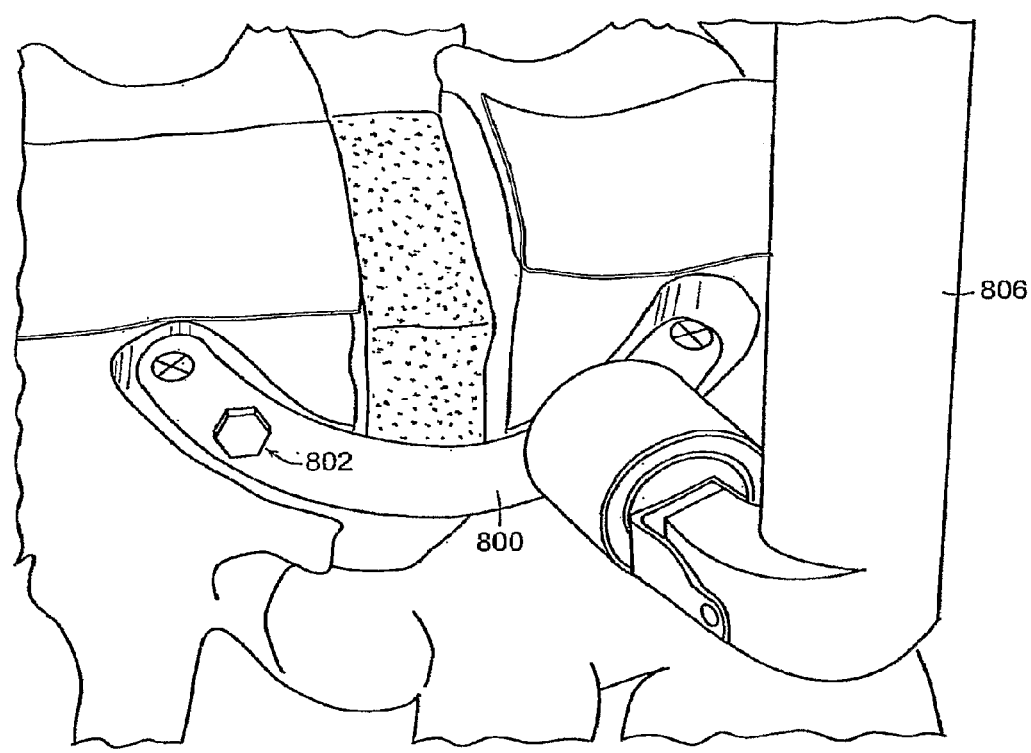
FIGS. 14A-D are illustrations of the process for implanting or attaching a curved rod across the adjacent vertebrae.
Figure 14B:
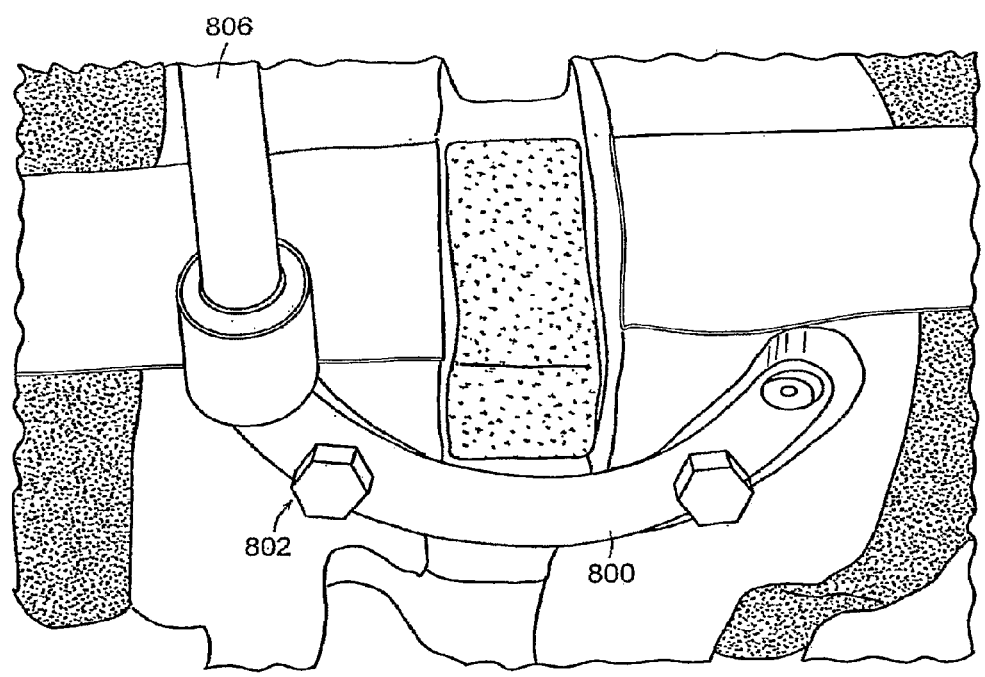
Figure 14C:
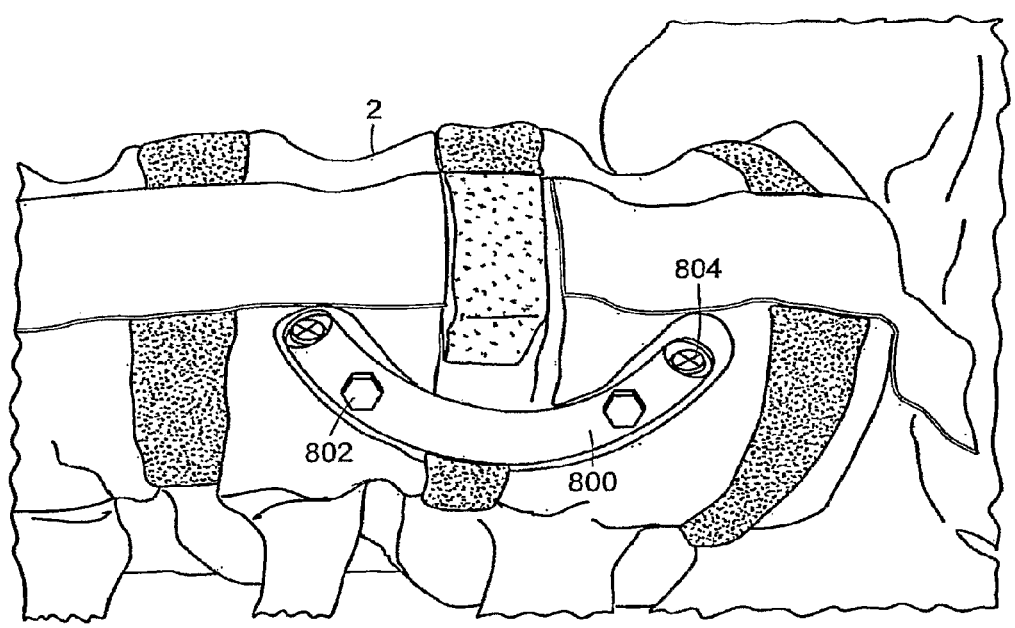
Figure 14D:
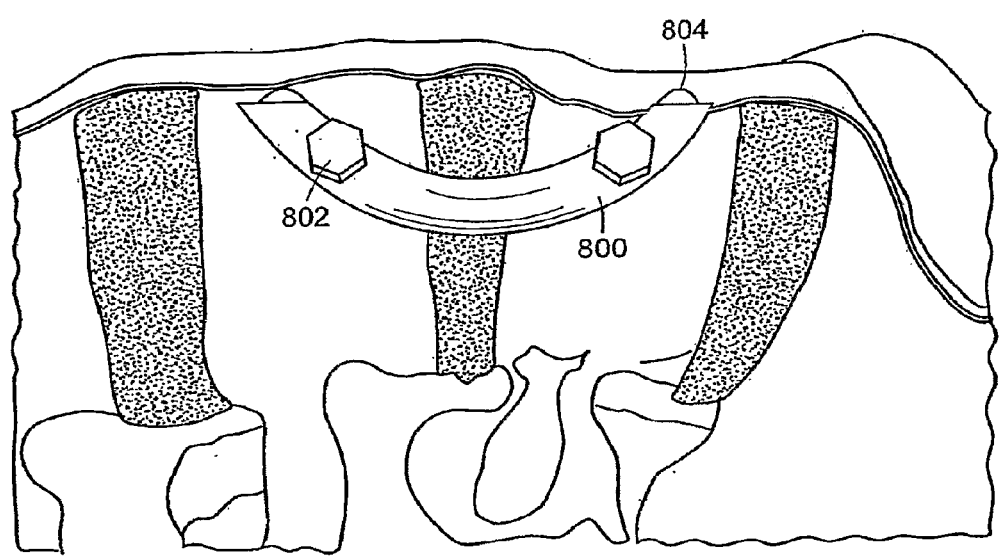

Two lateral screws 802 pass through the lateral holes of the curved rod and set on the lateral surface of the implant. The two end screws 804 are passed through the open ends of the curved rod and each is inserted until the screw head is contained within the hollow of the implant. The lateral and end screws are inserted using for example a Cardan screwdriver 806. As shown in FIGS. 14C-D the curved rod is now securely in place in either of the recess (FIG. 14C) or a surface-mounted configuration (FIG. 14D).

Referring now to FIGS. 15A-H there is shown a series of views illustrating the process for the medial approach. Reference shall also be made to FIGS. 1-11 and 17-18 and the discussion related thereto as well as for FIGS. 13-14 for features and functions not provided in the following discussion. As above, the area of concern is exposed by a surgeon using the appropriate technique and the drilling apparatus frame 202 is aligned such that it is vertical in an anteroposterior orientation and placed as far midline as possible on the anterior aspect of the vertebrae across the operative level. The pointed ends of the nail members 206 are then driven through the platform frame 202 and the first path guards 204 so as to be driven into the vertegral cortex to hold the frame in place while cutting the channel or through aperture. See FIG. 15A-B.

The pivot arm assembly 300 is then secured to the frame 202 and thereby also securing the drill assembly to the frame. The drive motor 20 also is coupled to the drill assembly 300 via the adapter 414 See FIG. 15C. The pivot arm 302 is then rotated until the drill bit 410 and the pivot arm are in the start position, whereat the drill motor 20 is started. See FIG. 15D.

The pivot arm is rotated so as to cause the drill bit to travel in a downward circular path thereby making cuts in the vertebral body. In the case where, the first cut does not cut a complete channel or through aperture, the pivot arm assembly is detached from the frame, flipped, reconnected to the frame and the cutting process described above is repeated until the rest of the channel or through aperture has been cut. See FIGS. 15D-F.

Figure 15A:
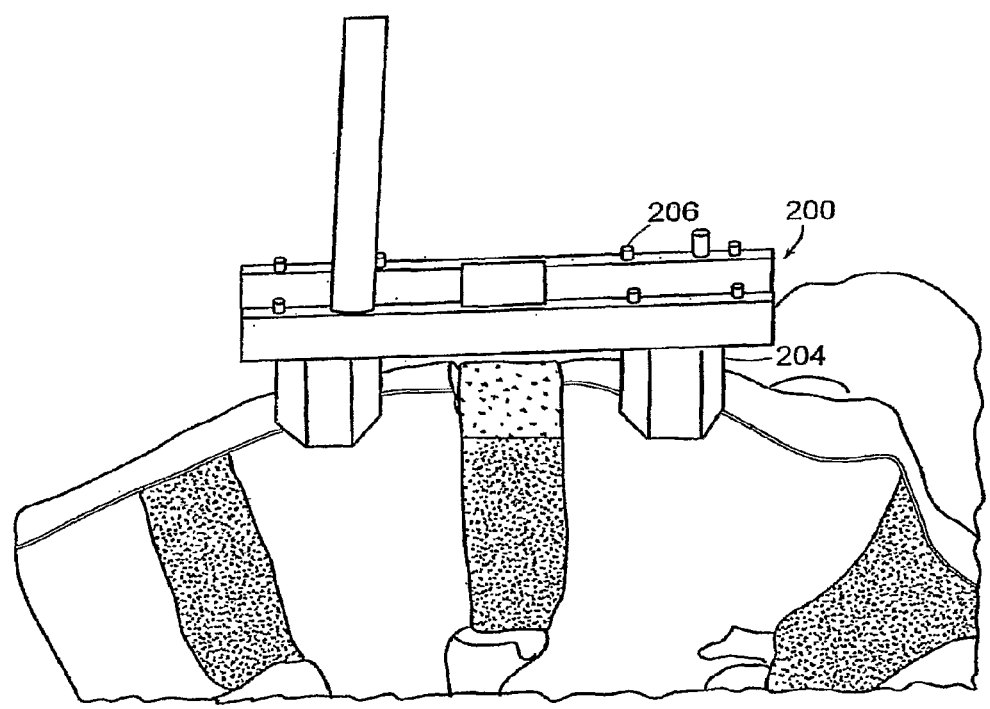
FIGS. 15A-H are illustrations of the process for forming a through aperture in adjacent vertebral bodies.
Figure 15B:
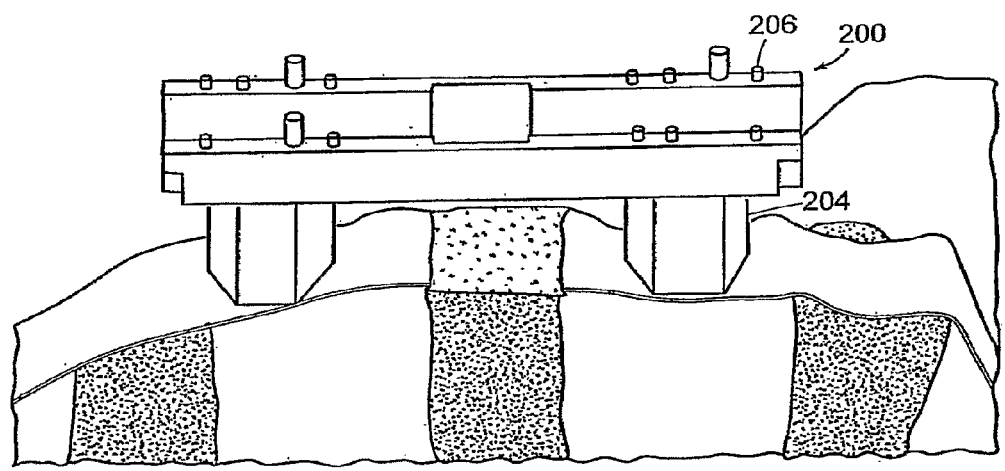
Figure 15C:
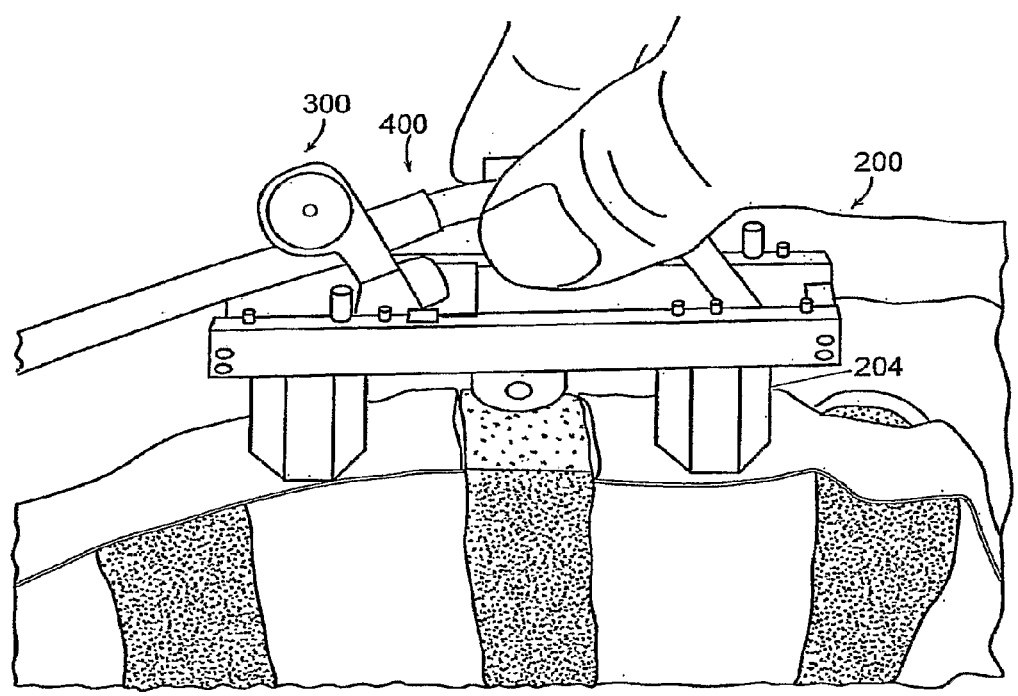
Figure 15D:
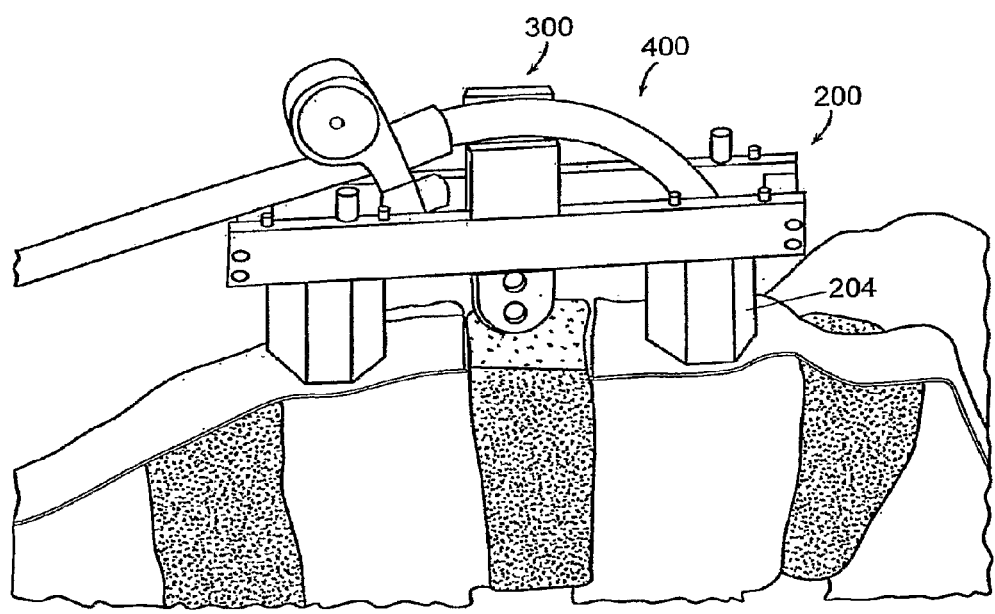
Figure 15E:
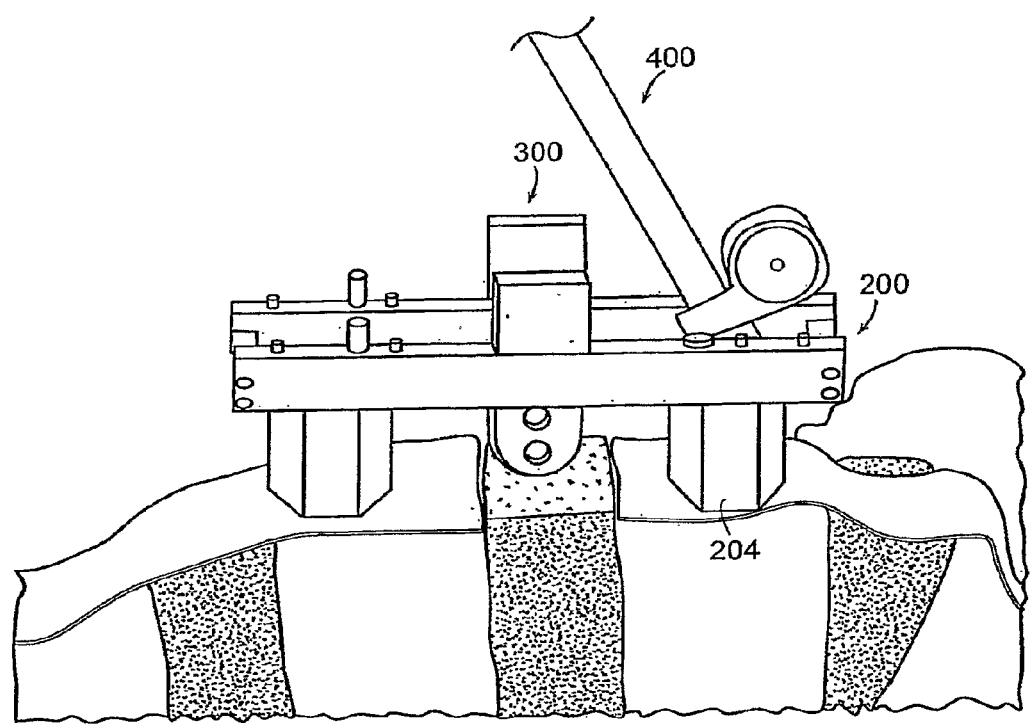
Figure 15F:
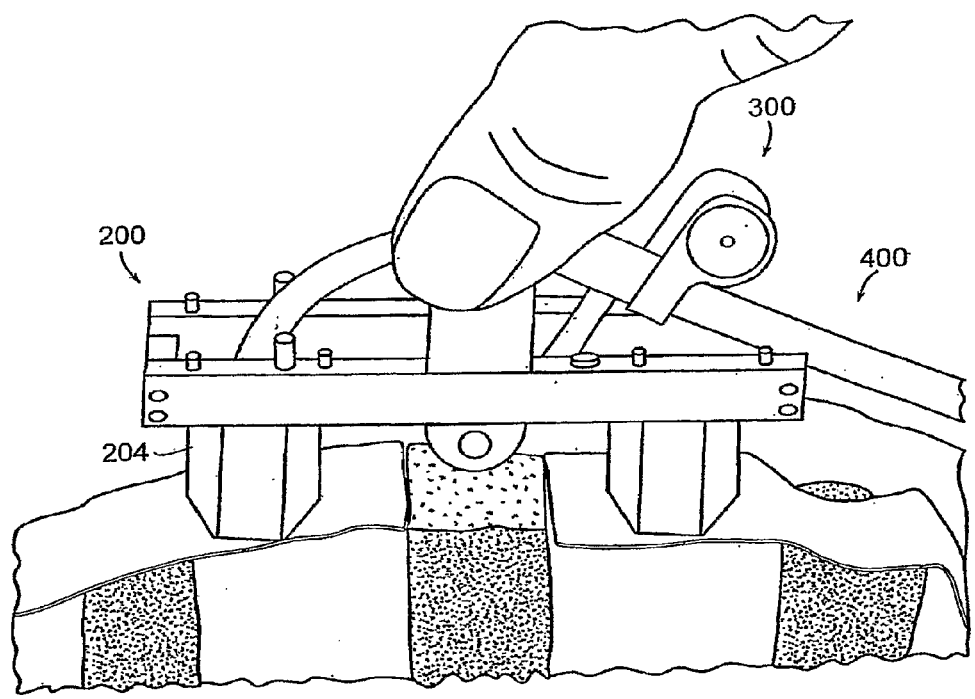
Figure 15G:
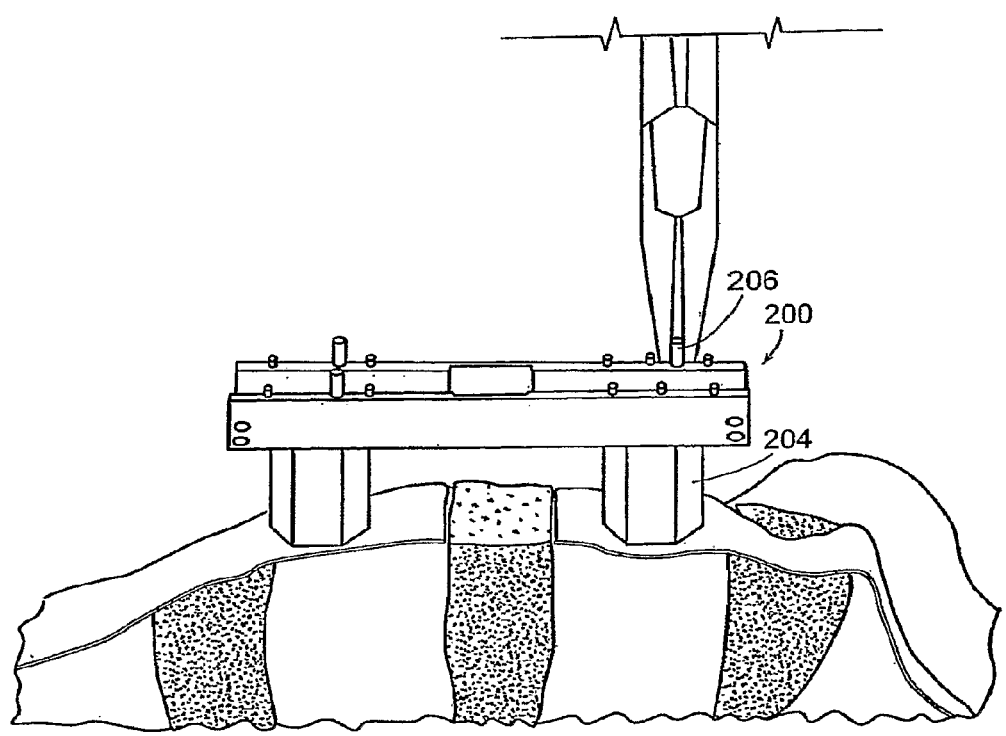
Figure 15H:
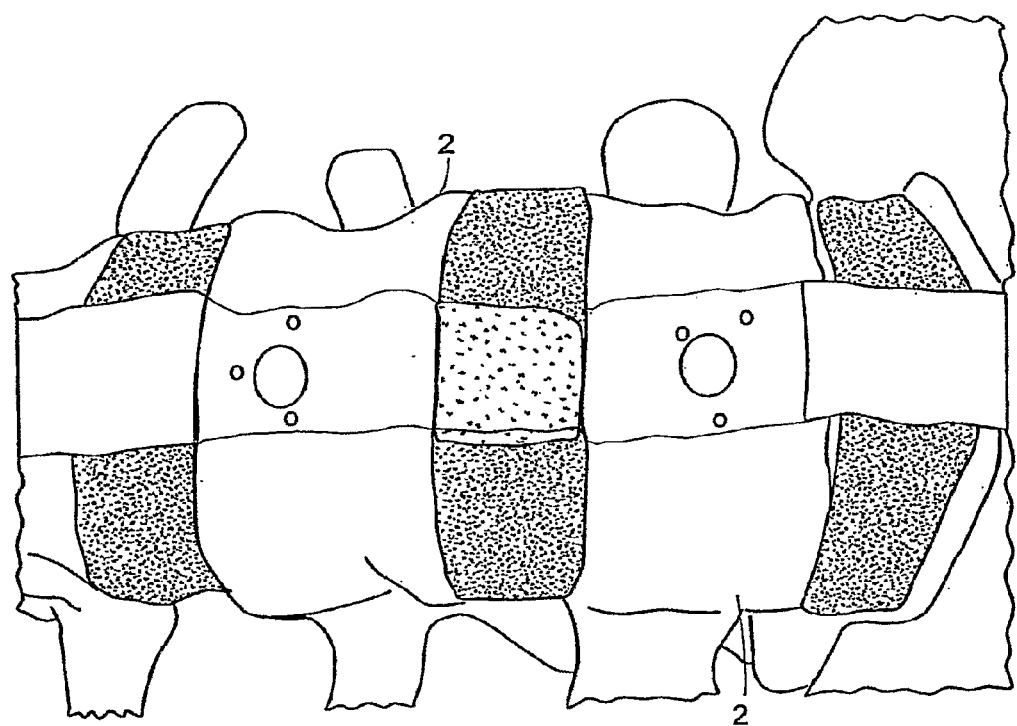
Figure 15I:
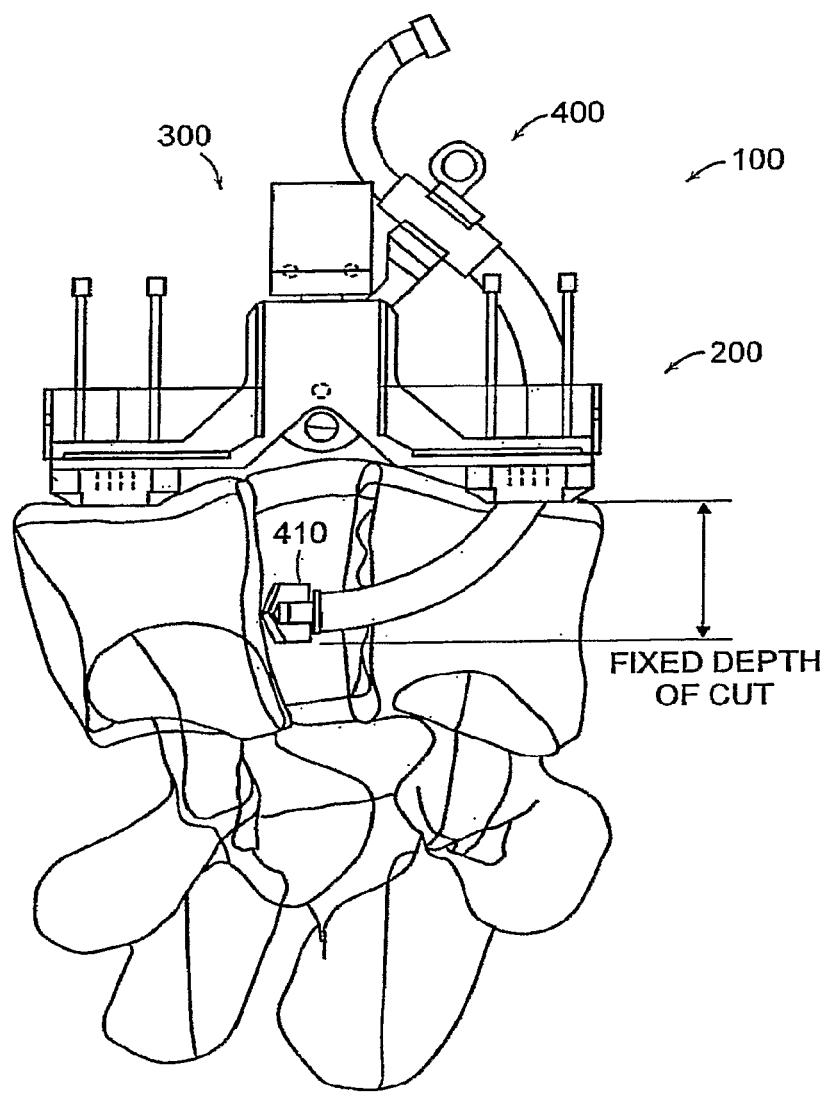
FIG. 15I is an illustrative view of adjacent vertebral bodies illustrating the fixed cutting depth aspect yielded by the drilling apparatus of the present invention.

There is shown in FIG. 15I, a illustrative view of adjacent vertebral bodies with the drilling apparatus 100 of the present invention mounted thereon. As illustrated, the arrangement of the drilling apparatus 100 of the present invention is such that the drilling bit follows a fixed path established by the configuration of the drilling apparatus 100. In this way, a maximum or fixed cutting depth also is set or established by the configuration of the drilling apparatus 100.

After the complete channel or through aperture is cut in the adjacent vertebral bodies, the pivot arm assembly 300 and the drill assembly 400 are detached from the frame 202 and the nail members 206 are removed from the vertebral bodies and the frame or platform assembly 200 is removed from the operative site. As indicated herein, removal of the nail members 206 can be accomplished using the nail member removal device 500 of the present invention. The above process yields a channel opening or through aperture in both vertebral bodies that can accept the curved rod 800. See FIGS. 15G-H.

It should be recognized that it is within the scope of the present invention to cut a channel through or partially through one of the vertebral bodies. Thus, the foregoing process is adaptable for accomplishing this by limiting rotational movement such that a channel is not cut completely through one of the vertebral bodies.

Figure 16A:
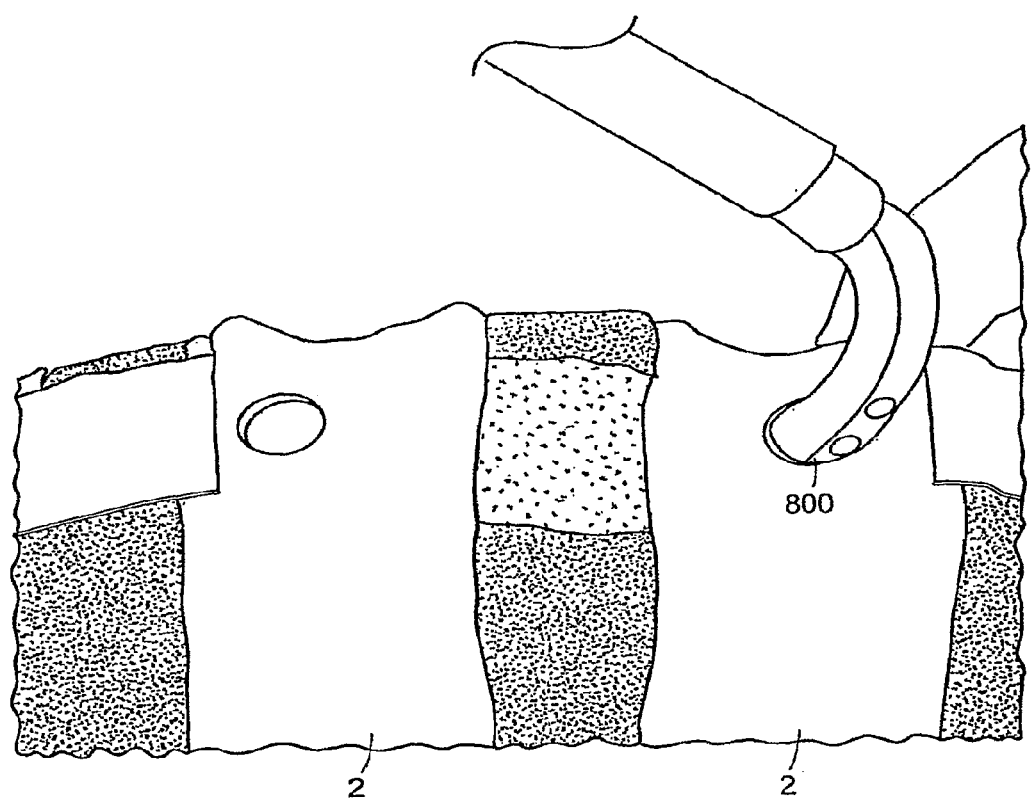
FIGS. 16A-C are illustrations of the process for implanting or attaching a curved rod in the through aperture and across the adjacent vertebrae.
Figure 16B:
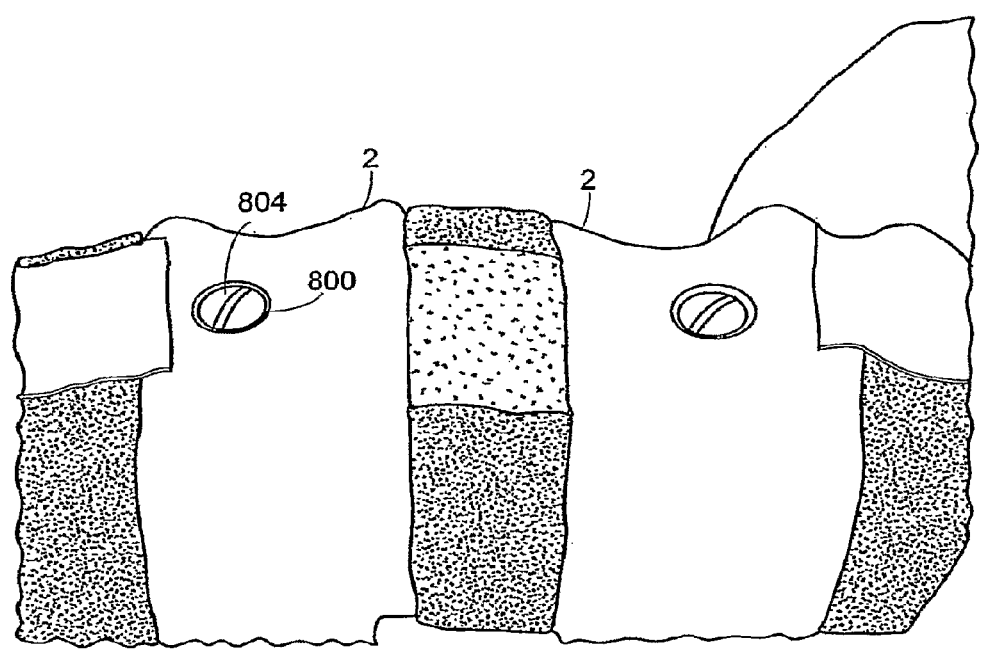
Figure 16C:
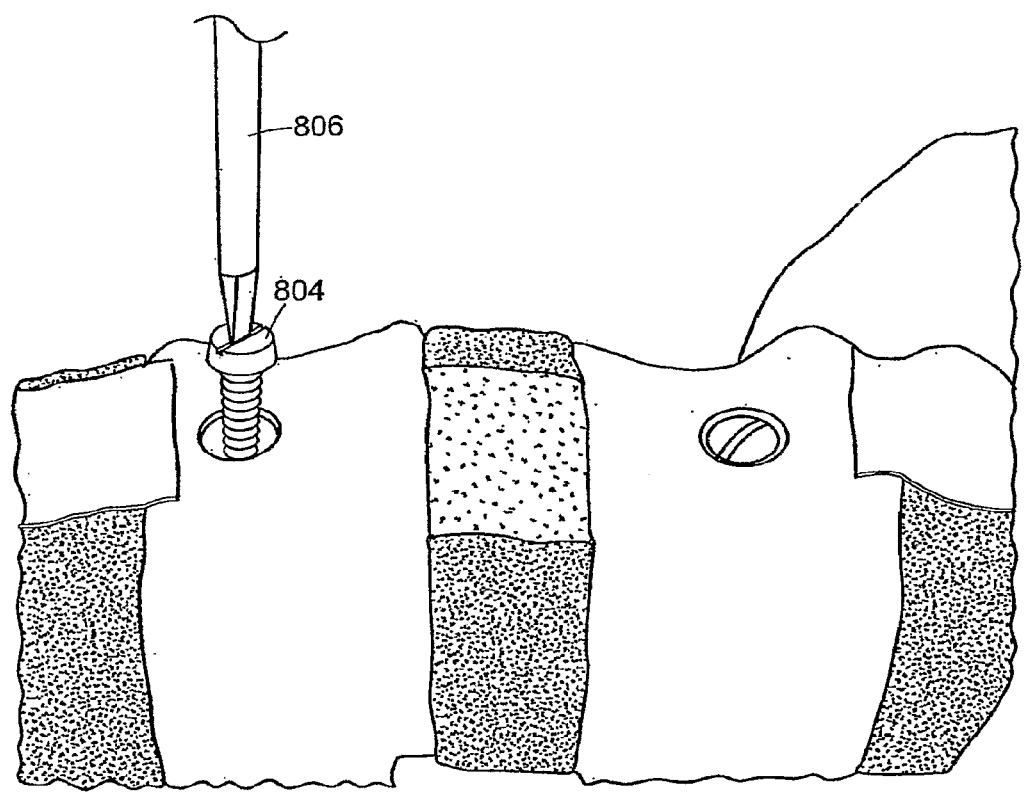

Now with reference to FIGS. 16A-C there is shown the process for placing, positioning and attaching or implanting a curved rod 800, including those described in any of U.S. Pat. No. 6,607,530 and U.S. Ser. No. 10/019,265, the teachings of which are incorporated herein by reference. The curved rod 800 is inserted into the channel and manipulated so that the curved rod is submerged along the midline of the vertebra (see FIGS. 16A-B). The curved rod 800 is now secured to the vertebral bodies using interlocking screws 804 that traverse the rod and penetrate the vertebra at an angle that will avoid sensitive neurologic structures. The screws hold the curved rod 800 in place and stabilize the motion segment to facilitate healing of the bone within the disc space.

Two end screws 804 are passed through the open ends of the curved rod and each is inserted until the screw head is contained within the hollow of the implant. The screws are inserted using for example a Cardan screwdriver 806.

It should be recognized, and as taught in any of U.S. Pat. No. 6,607,530 and U.S. Ser. No. 10/019,265, the teachings of which are incorporated herein by reference, the curved rods 800 can be configured so as to include fenestration or surface artifacts that secure the curved rod within the channel without the retaining screws 804 are described above or in addition to such retaining screws.

Figure 22A:
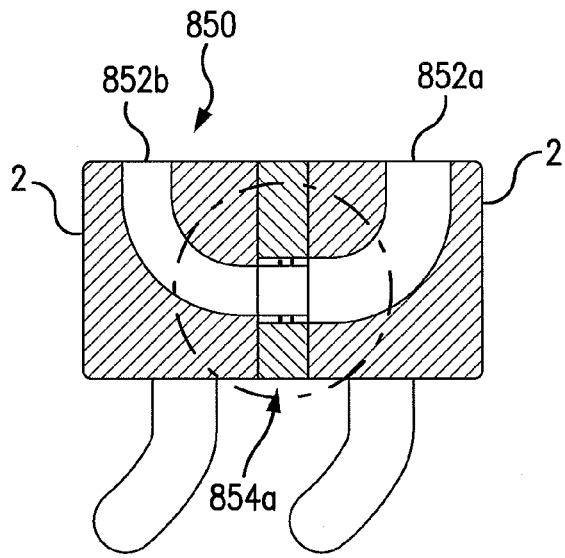
FIG. 22A is a cross-sectional side view that illustrates implanting or attaching a sliding implant device in the through apertures and across the adjacent vertebrae.
Figure 22B:
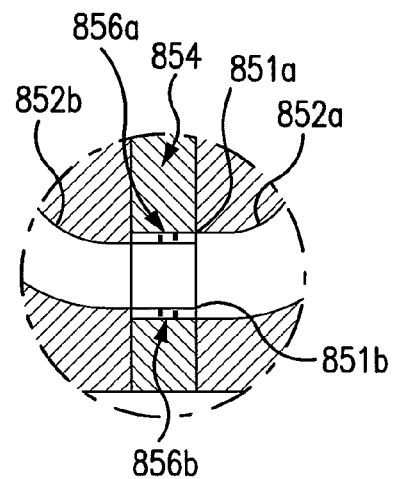
FIG. 22B is a detailed view of sliding connection of the sliding implant device of FIG. 23A.

In addition to the foregoing teachings of any of U.S. Pat. No. 6,607,530 and U.S. Ser. No. 10/019,265 as to the type and form of rod or implant that can be placed, positioned, attached and/or implanted, there are shown in FIGS. 22-24 other implants that are contemplated for use with the methodology, devices and/or apparatuses of the present invention as well as for use in combination with any of a number of other methodologies, devices and/or apparatuses described in U.S. Pat. No. 6,607,530 and U.S. Ser. No. 10/019,265. Now with reference to FIGS. 23A,B there is shown a sliding implant device 850 or a dynamized implant device that includes first and second members that are configured and arranged so as to form a sliding interconnection 854 there between. Such a sliding implant device 850 provides a mechanism to provide stability to the spine while preserving at least some ability of motion in the spine. Such a device provides dynamic stabilization to a patient who needs stability but necessarily fusion of adjacent vertebrae.

In a particular embodiment, the sliding interconnection 854 is formed by having an end 851*a* of the first member 852*a* being slidably disposed with an end 851*b* of the second member 852*b*. As illustrated in FIG. 22B, in the inner diameter of at least the end 851*a* of the first member 852*a* is larger than the outer diameter of the end of the second end 851*b* of the second member 852*b*. This can be achieved using any of a number of techniques known to those skilled in the art. As illustration, in one case the first member end 851*a* is machined or processed so that this end is expanded radially outwardly so as to form a socket for receiving the send member end 851*b*. In another case, the second member 852*b* is formed so the end 851*b* has an outer diameter that is set so as to slidably received within the first member end 851*a*. In yet another case, the first member 852*a* is formed so that the end 851*a* includes a pocket therein and the second member 852*b* is formed so the end 851*b* has an outer diameter that is set so as to slidably received within the pocket of the first member end 851*a*.

In further embodiments, the first member 852*a* is a solid member and the end 851*a* is formed so as to create a pocket or socket within the first member and the second member 852*b* is a solid member and the end 851*a* thereof is formed so as to have a reduced diameter so as to form a plug type end that can be slidably received within the socket/pocket of the first member 852*a*. In this way, the shoulder of the plug end and the lip of the first member end cooperate to stop further relative motion between the first and second members 852*a,b*. In further embodiments, the first and second members 852*a,b* have respective different outer diameters such that the outer diameter of the second member 852*b* is less than the inner diameter of the first member or the pocket/socket on the end 851*a* thereof.

In further particular embodiments, and with reference to FIG. 22B, the respective ends 851*a,b* of the first and second members 852*a,b* also are arranged so as to include stop members 856*a,b* that cooperate to restrict relative movement between the first and second members as well as restrict relative movement between the adjacent vertebrae 2. In exemplary embodiment, the stop members 856*a,b* extend outwardly from opposing surfaces of the first and second members 852*a,b*. The stop members 856*a,b* also are arranged such that when the first and second members are secured within the adjacent vertebrae 2, the stop members are opposed to each other and spaced from each other corresponding to a given spacing between the adjacent vertebrae.

Thus, when the spacing between the adjacent vertebrae changes responsive to relative movement of the adjacent vertebrae (e.g., compression), such relative movement also causes the stop members 856*a,b* to also move with respect to each other. When the stop members 856*a,b* contact each other, however, further relative movement between the first and second members 852*a,b* as well as between the adjacent vertebrae is restrained. Thus, the spacing between the stop members in effects sets the dynamic range of movement for the adjacent vertebrae. In further embodiments, the spacing between the stop members 856*a,b* is adjusted so as to provide different dynamic ranges of movement.

In further exemplary embodiments, each of the stop members 856*a,b* comprise a plurality or more of segments, each segment extending around part of the circumference of the respective first and second members so as to form channels between the adjacent segments of a respective first or second member. These channels form paths through which the stop member segments of the other of the first and second member can pass axially when forming the sliding interconnection. When the first and second members 852*a,b* are assembled to form the sliding interconnection, the stop member segments are rotated with respect to each other so that they are orientated opposed to each other.

In further exemplary embodiments, the stop members 856*a,b* and the stop member segments, are formed integral with the respective first and second members 852*a,b*. In alternative embodiments, the stop members 856*a,b* and the stop member segments, are coupled or secured to the respective first and second members 852*a,b* using any of a number of techniques known to those skilled in the art (e.g., adhesives, welding, brazing, ultrasonic welding, laser welding, or other mechanical connections) and appropriate for the structure forming the first and second members 852*a,b* of the implant device.

Referring now to FIGS. 23A-C there is shown another embodiment of a dynamized implant device 860 that includes first and second members 862*a,b* members, that are configured and arranged so as to form a sliding or piston-like interconnection between opposing ends of the respective first and second members, and a compressive device 864 that is disposed between opposing ends of the respective first and second members. Such a dynamized implant device 860 provides a mechanism to provide stability to the spine while preserving at least some ability of motion in the spine. Such a device provides dynamic stabilization to a patient who needs stability but necessarily fusion of adjacent vertebrae.

The compressive device 864 comprises a spring, a compressive material, for example a bio-compatible foam material or other resilient or compressive material as is known to those skilled in art. In exemplary embodiments, the compressive device is operably coupled or secured to one of the opposing ends and in more particular embodiments is operably coupled to both opposing ends. For example, when a spring comprises the compressive device 864 one end of the spring is secured to the end 861*a* of the first member 862*a* and the other end of the spring is secured to the end 861*b* of the first member 862*a*.

In a further exemplary embodiment, and with reference to FIG. 23B, the ends 861*a',b'* of the respective first and second members 862 *a',b'* are arranged so the first member end 861*a'* is slidably disposed within a pocket 866 in the end 861*b'* of the second member b'. Also, the compressive device 864 is disposed within the pocket and between the ends 861*a',b'* of the first and second members.

In another further exemplary embodiment, and with reference to FIG. 23C, the end 861*a"* of the first member 862*a"* is configured so its cross-section or outer diameter is reduced with respect to that of the rest of the first member so as to from a plug 863*a* or piston-like member. In this arrangement, the plug like member 863, is slidably disposed within a pocket 866 in the end 861*b* of the second member 862*b"*. Also, the compressive device 864 is disposed within the pocket and between the ends 861*a",b"* of the respective first and second members.

Although the foregoing discussion, has generally described the present invention in terms of implanting one arcuate rod or implant device between bony segments such as between adjacent vertebrae, this shall not be construed as a limitation as it is contemplated and thus within the scope of the present invention for a plurality or more of implant devices 900 (FIGS. 24A,B) to be positioned and secured between adjacent bony segments including adjacent vertebrae. In further embodiments, the plurality or more of implant devices 900 can both have the same general makeup or constitution or the plurality or more of implant devices 900 can be different. Thus, and in addition to the foregoing teachings of any of U.S. Pat. No. 6,607,530 and U.S. Ser. No. 10/019,265 as well as that described hereinabove, the methods of the present invention can further include placing, positioning and attaching or implanting a plurality of implants 900.

Figure 24A:
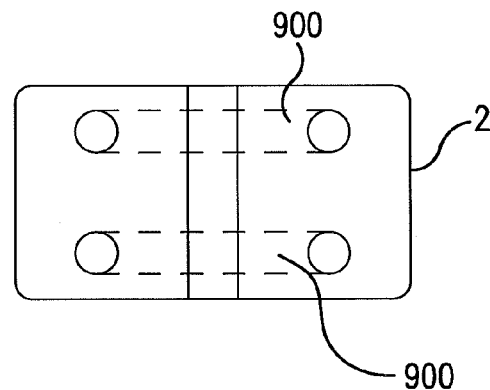
FIG. 24A illustrates implanting or attaching two curved implants in the through apertures and across the adjacent vertebrae.
Figure 24B:
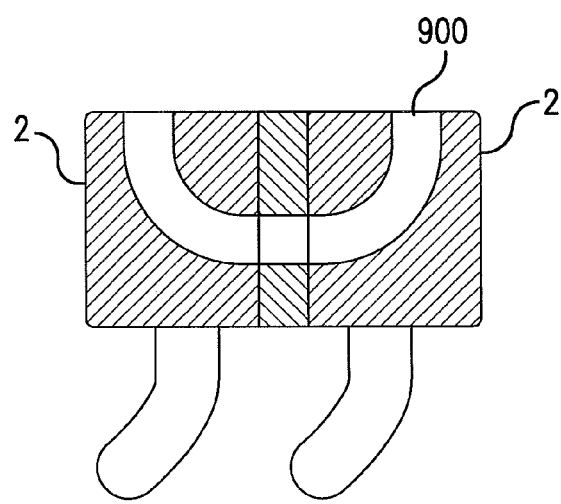
FIG. 24B is a cross-sectional side view of the implants within and across the adjacent vertebrae of FIG. 22A.
Figure 24C:
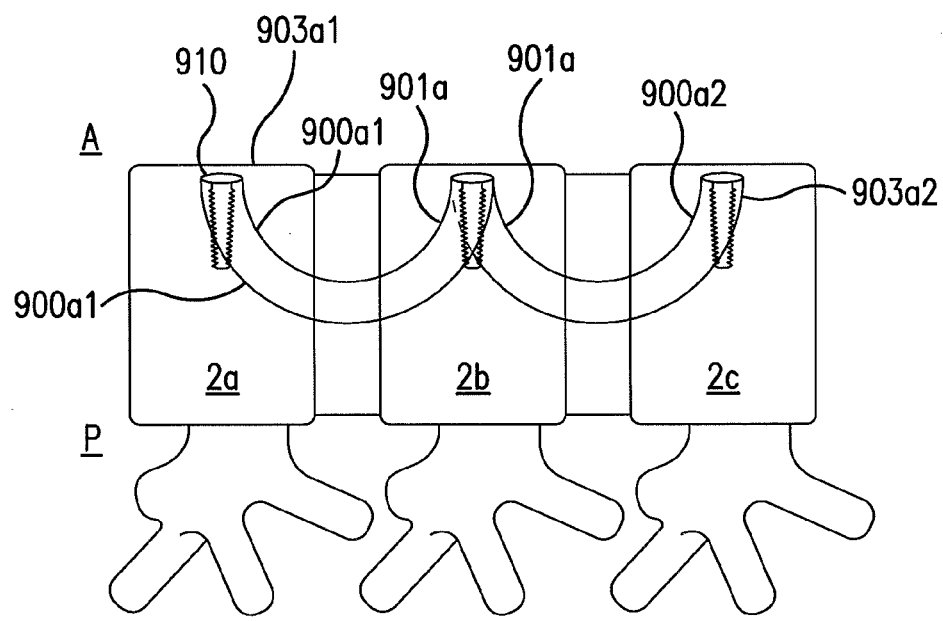
FIG. 24C is a lateral view of the spine showing an illustrative embodiment of stacked overlaid implant devices or arcuate rods in multiple adjacent vertebrae.
Figure 24D:
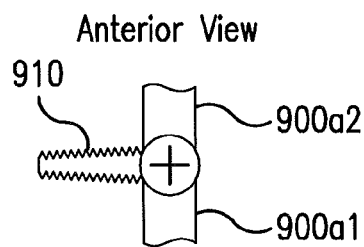
FIG. 24D is an anterior view of the crossing point of adjacent implant devices.

In addition to securing a plurality of implant devices in adjacent vertebrae is also is contemplated and thus within the scope of the present invention to position and secure one or more arcuate rods or implant devices in three or more adjacent vertebrae. Referring now to FIG. 24C, there is shown an illustrative embodiment in which two or more arcuate rods or implant devices 900a1,a2 are stacked or overlaid so that there is an implant device 900a1 extending between adjacent vertebrae 2a,b and another implant device 900a2 extending between adjacent vertebrae 2b,2c. In this illustrative embodiment, an end 901a1,901a2 of each implant device 900a1, 900a2 is located and secured in the same vertebrae 2b by a screw 910 or other type of device known to those skilled in the art. The other end 903a1, 903a2 is secured in the respective vertebrae 2a,2c by a screw 910. In particular embodiments, and with reference to the anterior view shown in FIG. 24D, the ends 901a1, 901a2 being secured in the middle vertebrae 2b are configured and arrange so that one end 901a2 is configured so as to be disposed about the other end 901a1.

Figure 24E:
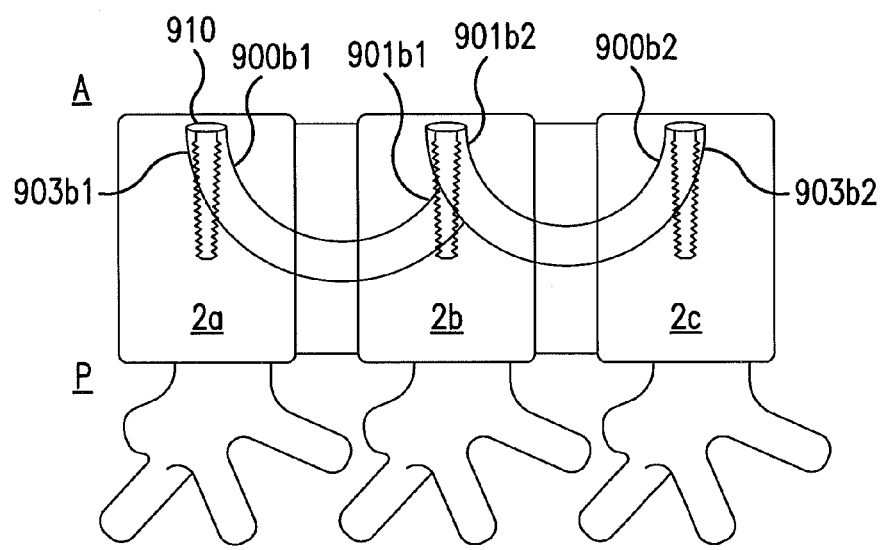
FIG. 24E is a lateral view of the spine showing another illustrative embodiment of stacked overlaid implant devices or arcuate rods in multiple adjacent vertebrae.

Referring now to FIG. 24E there is shown another illustrative embodiment, in which the one arcuate rod or implant device 900b1 is configured so as to be shorter than the other implant device 900b2. As with the embodiment described above, one end 903b1, 903b2 of each implant device 900b1, b2 is secured in the respective vertebrae 2a,2c by a screw 910. The shorter implant device 900b1 is configured so an end 901b1 thereof is disposed about a portion of the longer implant device 900b2 that is proximal to the end 901b2 that is to be secured in the middle vertebrae 2b by the screw 910. The end 901b1 of the shorter implant device also is configured so that the screw 910 exiting from the longer implant device 900b2 also passes through the end 901b1 so as to secure both ends 901b1,b2 in the middle vertebrae 2b.

Figure 19A:
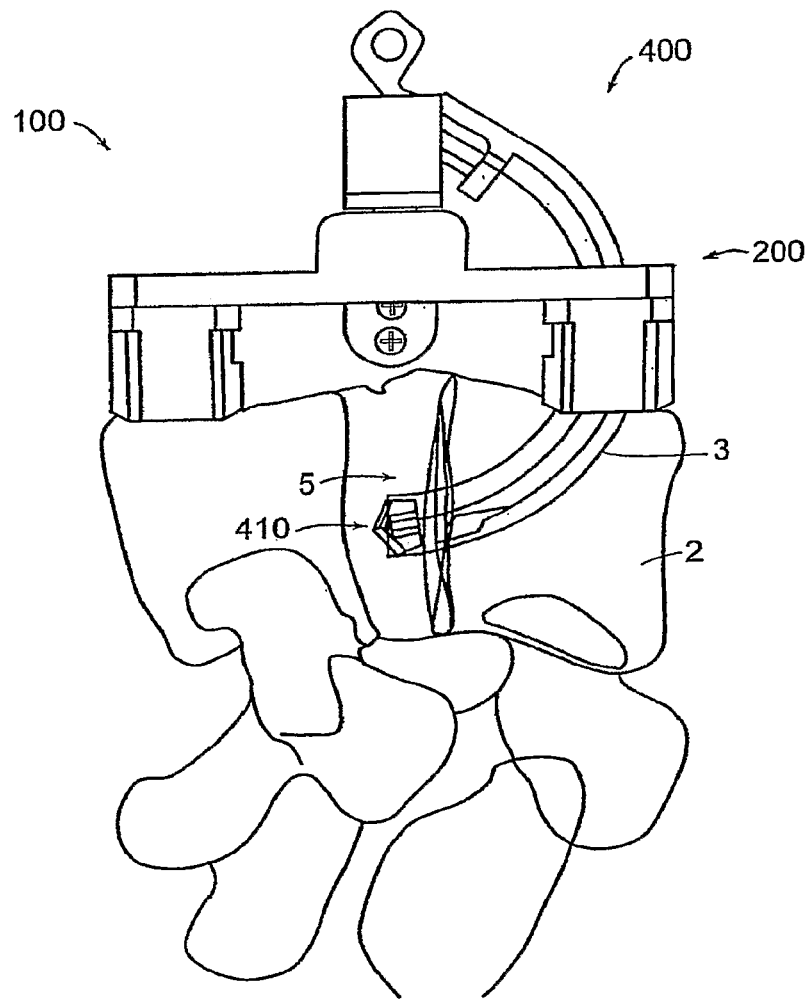
FIG. 19A is a perspective view of a portion of a spine on which is mounted a drilling apparatus of the present invention for creating a channel, passage or hole for a disk repair procedure.

As indicated herein, the drilling apparatus of the present invention is adaptable for use in a wide range of spinal repair procedures including but not limited to a repair procedure for an intervertebral disk 5 (FIGS. 19A,B). Although the following discussion refers to the drilling apparatus 100 according to one aspect/embodiment of the present invention, it is contemplated that any of the drilling apparatuses herein described are adaptable for use to perform such a disk repair procedure. Also, it is contemplated that a disk repair procedure according to the present invention also can be accomplished using any of the devices, apparatuses or mechanisms described in and as taught in any of U.S. Pat. No. 6,607,530 and U.S. Ser. No. 10/019,265.

Figure 19B:
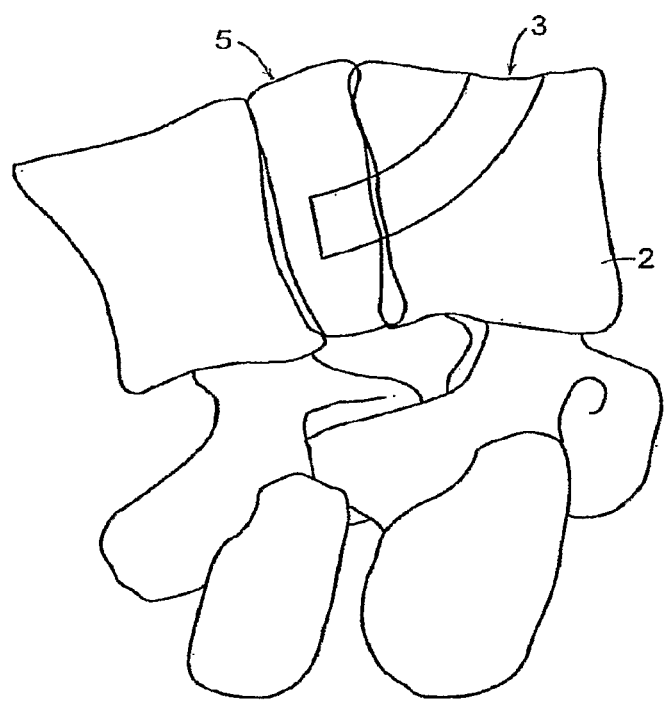
FIG. 19B is a perspective view of the portion of the spine illustrating the channel, passage or hole through an adjacent vertebrae allowing access to the nucleus.
Figure 20:
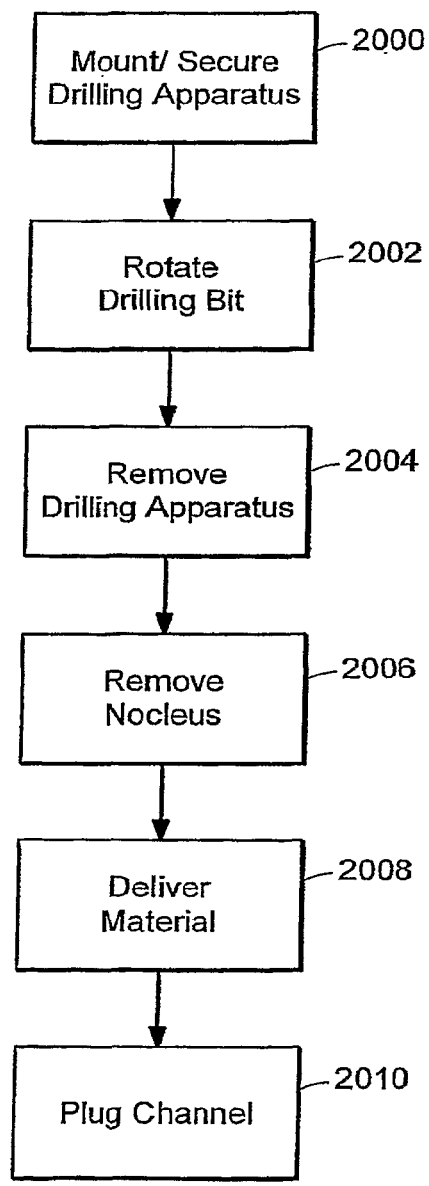
FIG. 20 is a flow diagram briefly describing a disk repair procedure according to the present invention.

Referring now to FIGS. 19A-B, there is shown a drilling apparatus 100 mounted/secured upon a spine, more specifically adjacent vertebrae 2, Step 2000. Such mounting and securing is accomplished using the methods and techniques for doing so as described herein. Reference shall be made to FIGS. 1-9 and the discussion related thereto, for further details of the drilling apparatus not provided below. Reference also should be made to the process flow diagram illustrated in FIG. 20.

In further embodiments, the drill bit 410 of the drilling apparatus 100 and related components are selected so that the channel, passage or hole 3 in the adjacent vertebrae 2 is sized so as to provide a desired access to the nucleus for carrying out the repair procedure. For example, the hole 3 may be one size if a fluid or gel is to be injected into the nucleus, whereas it may be made larger if a prosthetic or device is to be inserted through the hole so as to reside in the area within the annulus for the disk nucleus.

After the drilling apparatus 100 is so mounted, the surgeon would manipulate the drill bit so as to cause it to rotate and create a curved or arcuate hole 3 in the adjacent vertebrae and into the disk 5, Step 2002. Such a drilling operation advantageously minimizes penetration of the vertebral endplates. Also, the drill as it follows the predetermined curved or arcuate path penetrates the vertebral end plates at essentially a right angle, thereby creating a circular defect. In contrast, the straight drill used in conventional techniques would penetrate the end plate at an angle thereby causing a larger elliptical shaped defect. The near perpendicular access created by the drilling apparatus of the present invention also minimizes trauma and/or disruption to the natural nucleus material. In contrast, a straight drill would need to penetrate more deeply into the disc space to complete the access hole.

In this regard it should be noted that while it is desirous to penetrate the nucleus of the disk, it should be recognized that it is possible that a portion of the annulus also may be drilled during the drilling procedure. Such an occurrence, however, shall not be construed as being unacceptable or outside the scope of the present invention.

Following creating of the hole, the drill bit 410 is extracted or removed from the hole 3 thereby allowing the surgeon access to the hole and thus the nucleus of the disk to be repaired. In particular embodiments, the surgeon would remove the drilling apparatus 100 so as to provide clear access to the opening formed by the hole 3, Step 2004. Thereafter, the surgeon would perform the particulars of the disk repair/replacing/augmentation procedure, such as but not limited to removing nucleus material (Step 2006), delivery of the nucleus augmentation material, artificial disk and/or artificial nucleus (Step 2008) and plugging of the channel, passage or hole 3 made in the adjacent vertebrae 2 (Step 2010). The nucleus material can be removed using any of a number of techniques known to those skilled in the art including but not limited to water jets, chemical agents such as Chymopapain chemonucleolysis, rongers and emulsification technology.

Such augmentation material includes but is not limited to the devices, mechanisms and materials described in U.S. Pat. Nos. 5,824,093, 6,264,695 and U.S. Pat. No. 5,047,055 the teachings of which are herein incorporated by reference. Also, such delivery of the nucleus augmentation material, as well as such repair procedures, can include delivery and positioning of an annulus closure mechanism or device to seal or retain the artificial disc, nucleus and/or nucleus augmentation material or provide a closure for a defect in the annulus (such as but no limited to the devices described in U.S. Pat. Nos. 6,425,919 and 6,593,625, the teaching of which are incorporated herein by reference). As is known to those skilled in the art, when the annulus becomes damaged a defect is formed in the annulus that allows the nucleus for example, to cause the disk to bulge in a given direction. In addition, to delivery of nucleus or annulus repair and augmentation materials, it also is contemplated that drugs, medicaments, or other treatment materials can be delivered to the disk 5, vertebrae 2 or other element of the body.

The plugging of the hole 3 is accomplished using any of a number of techniques known to those skilled in the art, including but not limited to the use of bone/bone graft material. It also is contemplated that an arcuate rod as herein described also can be used to plug the hole 3. Thus, the plugging of the hole 3 becomes a relatively straightforward procedure. Also, the plugging should advantageously create a relatively smooth surface at the end plate and the load forces on the vertebral end plate will be perpendicular to the access hole. Such plugging is particularly advantageous as compared to some conventional techniques as defects in the annulus do not heal; whereas defects in the bone (e.g., the vertebral body) can be plugged with bone, metal, etc. and the bone heals around the plug.

Referring now to FIGS. 25-29 there is shown exemplary frame assemblies for a drilling assembly according to another aspect of the present invention, in which an intervertebral spacer or spacer element is removably secured to and extends from the frame assembly so as to be maintained in a fixed relation to the frame assembly as the channel is being formed in the adjacent bony segments or adjacent vertebral bodies. In particular embodiments, the intervertebral spacer is secured to the frame assembly so as to prevent rotational motion of the intervertebral spacer with respect to the channel. Such an arrangement provides a mechanism thereby also provides a mechanism for maintaining alignment of the spacer to the channel as well as to the position of the drill. The intervertebral spacer also allows the surgeon to maintain extremely accurate disk spacing and also protects the spinal cord.

In further embodiments, the intervertebral spacer is formed so that the drill bit 410 as it is being rotated to form the channel passes through the spacer thereby also forming an aperture in the spacer that has corresponds characteristics as the channel formed in the adjacent bony structure/vertebral bodies (e.g., same curvature, diameter). In another embodiment, the intervertebral spacer is formed so as to include a pre-formed aperture; through which the drill bit 410 passes as the drill bit is being rotated to form the channel in the adjacent bony structure or adjacent vertebral bodies. In yet another embodiment, the intervertebral spacer is formed so as to include a pre-formed aperture smaller than the channel to be formed. The drill bit 410 passes through the portion of the spacer including the pre-formed aperture as the drill bit is being rotated, thereby forming the channel in the adjacent bony structure or adjacent vertebral bodies. Such intervertebral spacers can be made using any of a number of techniques and materials known to those skilled in the art and in particular embodiments, the spacer design is suitably based on a construction that facilitates the selected technique for creating an arcuate aperture. In more particular embodiments, the intervertebral spacers are bone, metal, allograft, autologous, plastic (e.g., PEK) or other material appropriate for the intended use.

In further embodiments, the surgical personnel select an intervertebral spacer that is appropriately sized, so it can accommodate the distended disc space. In yet further embodiments, the mechanism securing the intervertebral spacer to the frame assembly is disengaged thereby releasing the spacer from the drilling apparatus following the drilling or forming of the channel in the adjacent bony segments or vertebral bodies. In this way, the intervertebral spacer remains disposed in the intertertebral disc space. In yet further embodiments, the implant or arcuate rod is inserted into and through the through aperture in the spacer so as to thereby secure the spacer between the intervetebral bodies.

Figure 25A:
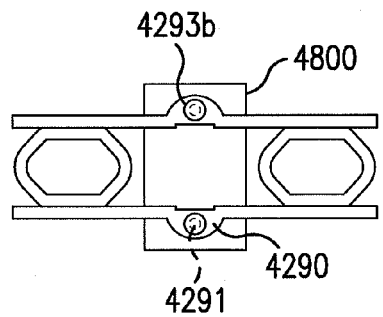
FIGS. 25A,B are top and side views respectively of an illustrative frame according to another aspect of the present invention.
Figure 25B:
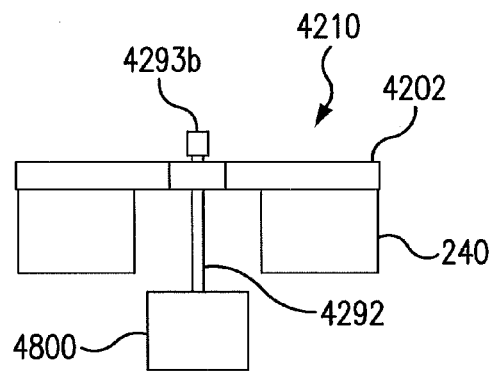
FIG. 25C is a perspective view of a portion of a spine on which is mounted the illustrative frame of FIGS. 25A,B.
Figure 25C:
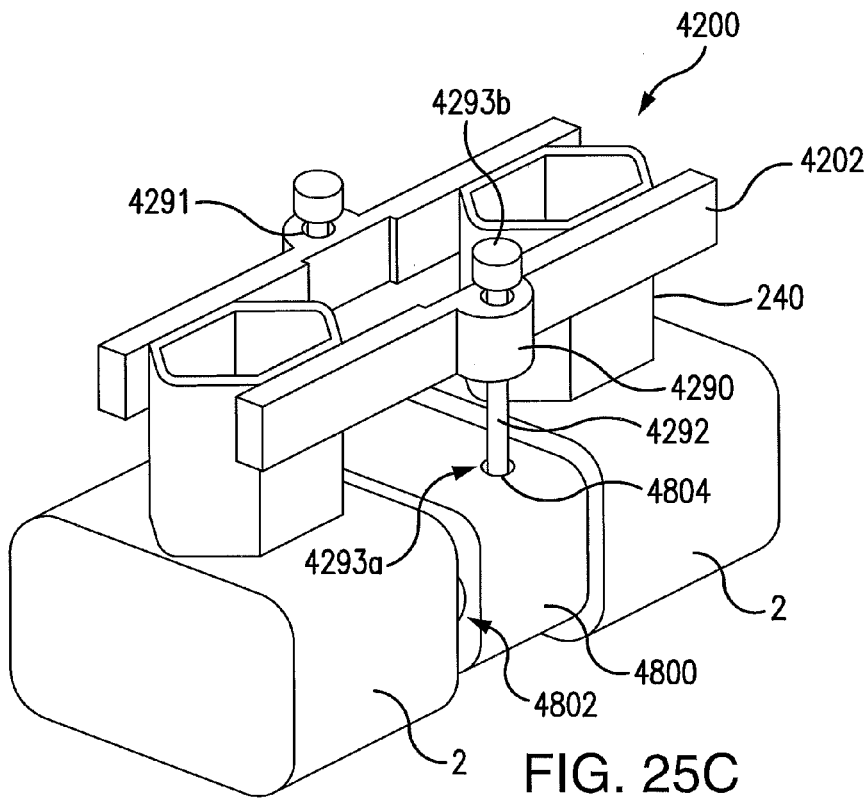

Referring now to FIGS. 25A-C there is shown one embodiment of an exemplary frame assembly 4200 according to this aspect of the present invention, in which the frame 4202 includes a plurality of side protrusions 4290 that are positioned at about the mid-point of the frame and on either side of the frame. Each of the side protrusions includes a through aperture 4291. The exemplary frame assembly 4200 also included a plurality of posts 4292 or connectors; each of which are disposed in one of the protrusion through apertures 4291. The posts 4292 are generally arranged so that an end 4293a thereof is generally directed towards the intervertebral space between the vertebral bodies 2.

In particular embodiments, this end 4293a of the posts 4292 is configured so the post or connector is releasably secured to the intervertebral spacer 4800. In illustrative exemplary embodiments, an aperture 4804 provided in the spacer 4800 and the end 4293a of the posts 4292 are threaded, whereby the spacer is threadably secured to the posts. In further embodiments, the other end 4293b of the posts 4292 is configured so has to have a head or other feature that prevents the post from passing through the protrusion through aperture 4291. In yet further embodiments, the length of each post is established such that when the intervertebral spacer 4800 is so secured to the frame assembly the spacer is appropriately positioned with respect to the travel path of the drill bit 410 as it is being rotated to form the channel. In particular embodiments, the intervertebral spacer 4800 is secured to the frame assembly so the pre-formed aperture 4802 in the spacer is appropriately positioned and so as to be congruent with the travel path of the drill bit 410 as it is being rotated to form the channel.

Figure 26A:
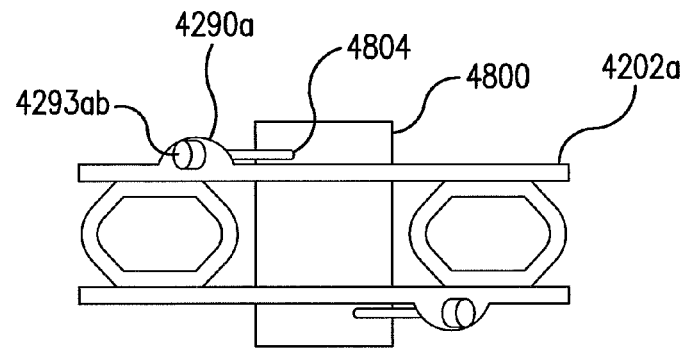
FIG. 26A is a top view of an embodiment of the illustrative frame according to said another aspect of the present invention.
Figure 26B:
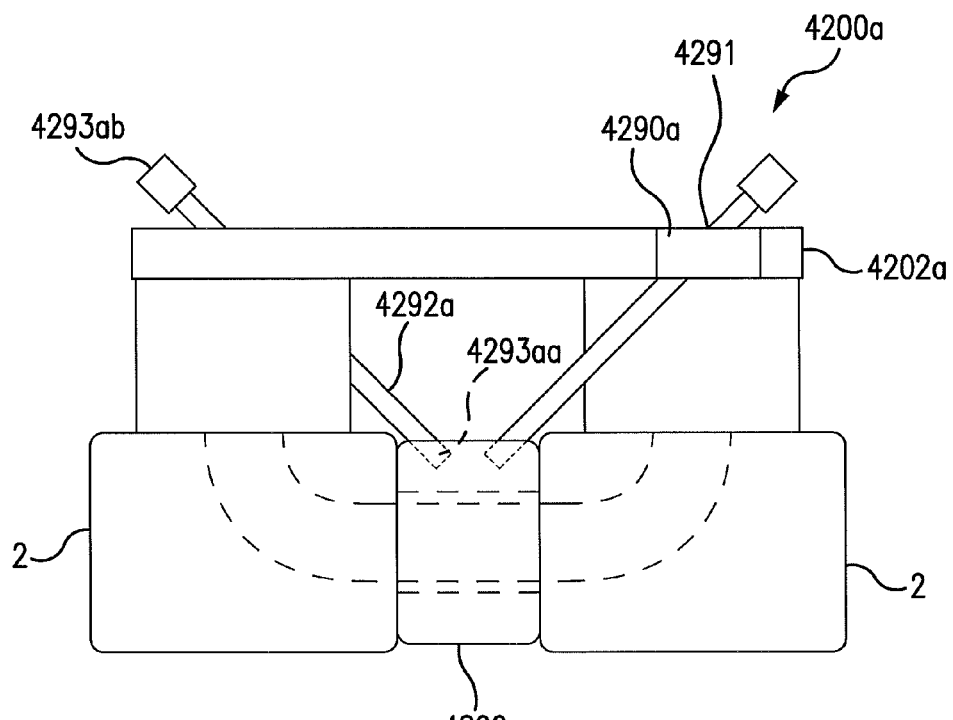
FIG. 26B is a perspective view of a portion of a spine on which is mounted the illustrative frame of FIG. 26A.

Referring now to FIGS. 26A-B there is shown another embodiment of an exemplary frame assembly 4200a according to this aspect of the present invention, in which the frame 4202a includes a plurality of side protrusions 4290a that are positioned away from the mid-point of the frame and on either side of the frame. Each of the side protrusions includes a through aperture 4291. The exemplary frame assembly 4200a also included a plurality of posts 4292a or connectors; each of which are disposed in one of the protrusion through apertures 4291. The posts 4292 are generally arranged so that they extend at an angle from each protrusion and so that an end 4293aa thereof is generally directed towards the intervertebral space between the vertebral bodies 2.

In particular embodiments, this end 4293aa of the posts 4292a is configured so the post or connector is releasably secured to the intervertebral spacer 4800. In illustrative exemplary embodiments, an aperture 4804 provided in the spacer 4800 and the end 4293aa of the posts 4292a are threaded, whereby the spacer is threadably secured to the posts. In further embodiments, the other end 4293ab of the posts 4292 is configured so has to have a head or other feature that prevents the post from passing through the protrusion through aperture 4291. The other end 4293ab also is configured so the surface contacting the frame 4202a complements the angle of the posts. In yet further embodiments, the length of each post 4292aa is established such that when the intervertebral spacer 4800 is so secured to the frame assembly the spacer is appropriately positioned with respect to the travel path of the drill bit 410 as it is being rotated to form the channel. In particular embodiments, the intervertebral spacer 4800 is secured to the frame assembly so the pre-formed aperture 4802 in the spacer is appropriately positioned and so as to be congruent with the travel path of the drill bit 410 as it is being rotated to form the channel.

Referring now to FIGS. 27A-C there is shown another embodiment of an exemplary frame assembly 5200a according to this aspect of the present invention that includes a frame 5202 and a clip mechanism 5210. The clip mechanism 5210 is attached or secured to the frame 5202 using any of a number of techniques known to those skilled in the art so that manipulation of the clip mechanism by a clinician or other medical personnel does not result in the detachment of the clip mechanism. In an illustrative exemplary embodiment, the clip mechanism 5210 includes a recessed portion 5218 in which is received portions of the frame 5202. In more particular embodiments, the clip mechanism 5210 is attached on the interior of the frame 5202 so that the clip portion 5212 thereof extends downwardly through the frame.

The clip mechanism 5210 is made of any of a number of bio-compatible materials, such as stainless steel and/or plastic, that are appropriate for the intended use (e.g., compatible with the material of the frame) and which can be attached or secured to the frame 5202.

The clip portion 5212 of the clip mechanism 5210 is configured so as to releasably hold the intervertebral spacer 4800 in the interior space 5214 of the clip portion. In use the surgeon manipulates the lever arms 5216 thereby causing the clip portion 5212 to release the intervertebral spacer. In particular embodiments, the manipulation of the lever arms 5216 causes the opposing arm segments of the clip portion 5212 to move away from each other so the spacer can pass out of the interior space 5214.

In further embodiments, the clip portion 5212 is configured so as to include a plurality of pairs of arm segments that are spaced from each other along the length of the frame 5202, where each pair of arm segments releasably holds the intervertebral spacer 4800. For example and as illustrated in FIG. 27B, one pair of arm segments can be located forward of the midpoint of the frame and the other pair of arm segments can be located rearward of the frame midpoint. In addition, there also is provided a plurality of pairs of lever arms 5216. In further embodiments, at least one pair of lever arms 5216 is provided for each pair of arm segments of the clip portion 5212 or at least one pair of lever arms segments is provided for a plurality or more of pairs of arm segments of the clip portion. Such an arrangement provides sufficient gripping area and force to hold the intervertebral spacer 4800 to the frame at least during formation of the channel and but allows the clinician to relatively easily open up the arms segments to release the spacer.

In further embodiments, the methods of the present invention further include securing the frame assembly 5200a to adjacent vertebral bodies 2 (FIG. 23C) so that the intervertebral spacer 4800 is disposed in the distended intervertebral space. Such methods further included manipulating the lever arms, for example following drilling or forming of the channel, so the intervertebral spacer 4800 remains disposed in the distended intervertebral space after the frame assembly is removed.

Figure 28A:
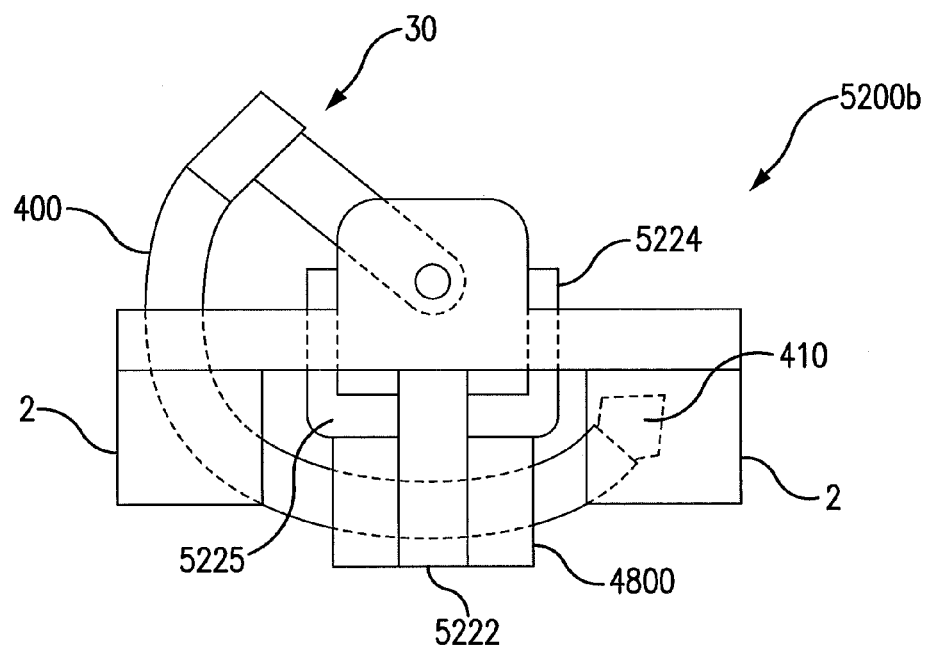
FIG. 28A is an illustrative view of a drilling apparatus including another embodiment of the illustrative frame according to another aspect of the present invention when mounted upon adjacent vertebral bodies.
Figure 28B:
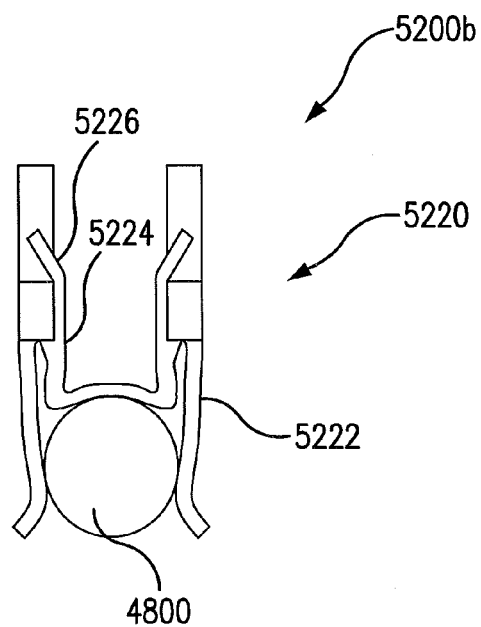
FIG. 28B is a cross-sectional end view of the illustrative frame of FIG. 28A.

Referring now to FIGS. 28A-B there is shown another embodiment of an exemplary frame assembly 5200b according to this aspect of the present invention that includes a frame 5202 and a spring clip mechanism 5220. The clip mechanism 5220 includes arm segments 5222 and a manipulating device 5224. The arm segments 5222 are each attached or secured to the frame 5202 on opposing sides of the frame so as to oppose each other using any of a number of techniques known to those skilled in the art so that manipulation of the clip mechanism by a clinician or other medical personnel does not result in the detachment of the clip mechanism. Also, the arm segments 5222 are attached or secured to the frame 5202 using any of a number of techniques known to those skilled in the art so that the process for forming the channel, including drilling of such a channel in the intervertebral spacer 4800, does not result in the detachment of the clip mechanism or release of the intervertebral spacer. The arm segments 5222 are made of any of a number of bio-compatible materials, such as stainless steel and/or plastic, that are appropriate for the intended use (e.g., compatible with the material of the frame) and can be attached or secured to the frame 5202.

The manipulating device 5224 is removably attached to the frame 5202, more particularly the interior of the frame. In addition, when removably attached to the frame, the manipulating device 5224 is disposed proximal to and above the intervertebral spacer and extending between the arm segments. In use the surgeon manipulates the lever arms 5226 thereby causing the arm segments 5222 to move away from each other and thereby release the intervertebral spacer 4800. In particular embodiments, a lateral segment 5225 extends between a plurality of pairs of lever arms 5226 and the manipulation of the lever arms 5226 causes the manipulation device lateral segment 5225 to urge the arm segments outwardly.

In further embodiments, the clinician or other medical personnel also can manipulate the manipulation device 5224 to detach the manipulation device from the frame. In this way, the intervertebral spacer 4800 can be inserted through the frame interior and secured in place when the manipulation device 5224 is thereafter inserted and secured to the frame.

Such an arrangement provides sufficient gripping area and force to hold the intervertebral spacer 4800 to the frame at least during formation of the channel and but allows the clinician to relatively easily open up the arms segments 5222 to release the intervertebral spacer. Also, as the arms segments 5222 and the manipulation device 52224 are removably attached or secured to the frame, a clinician can select arm segments and manipulations devices that are appropriate sized for locating a spacer in the intervertebral space for a given target site and a patient's particular physiology.

In further embodiments, the methods of the present invention further include securing the frame assembly 5200b to adjacent vertebral bodies 2 so that the intervertebral spacer 4800 is disposed in the distended intervertebral space. Such methods further included manipulating the lever arms 5226, for example following drilling or forming of the channel, so the intervertebral spacer 4800 remains disposed in the distended intervertebral space after the frame assembly is removed.

Figure 29A:
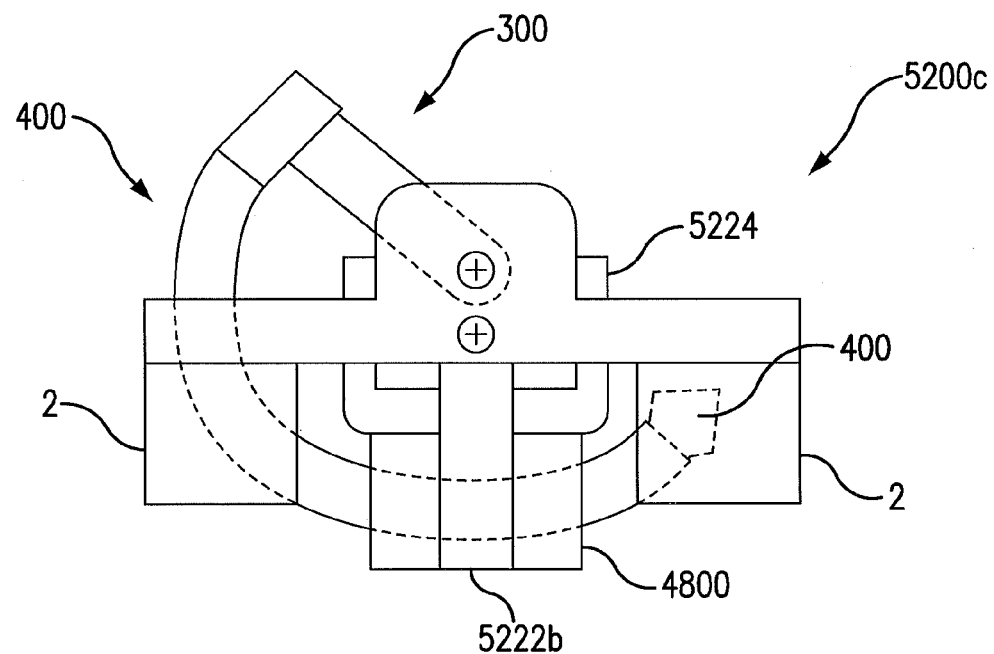
FIG. 29A is an illustrative view of another drilling apparatus including another embodiment of the illustrative frame according to another aspect of the present invention when mounted upon adjacent vertebral bodies.
Figure 29B:
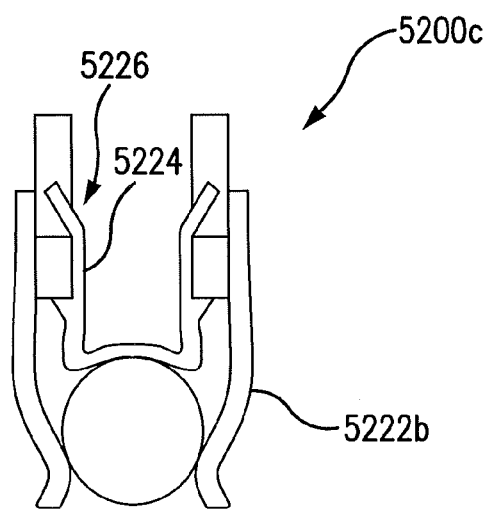
FIG. 29B is a cross-sectional end view of the illustrative frame of FIG. 29A.

Referring now to FIGS. 29A-B there is shown another embodiment of an exemplary frame assembly 5200b according to this aspect of the present invention that includes a frame 5202 and a spring clip mechanism 5220. The clip mechanism 5220 includes arm segments 5222b and a manipulating device 5224. Reference shall be made to the discussion regarding FIGS. 28A-B for details of features in common with this embodiment and not otherwise provided below.

The arm segments 5222b are each removably attached or secured to the frame 5202 on opposing sides of the frame so as to oppose each other using any of a number of techniques known to those skilled in the art so that manipulation of the clip mechanism by a clinician or other medical personnel does not result in the detachment of the clip mechanism. The arm segments 5222b also are each removably attached or secured to the frame 5202 using any of a number of techniques known to those skilled in the art so that the process for forming the channel, including drilling of such a channel in the intervertebral spacer 4800, does not result in the detachment of the clip mechanism or of the intervertebral spacer. The arm segments 5222b are made of any of a number of bio-compatible materials, such as stainless steel and/or plastic, that are appropriate for the intended use (e.g., compatible with the material of the frame) and can be attached or secured to the frame 5202.

The manipulating device 5224 is removably attached to the frame 5202, more particularly the interior of the frame. In addition, when removably attached to the frame, the manipulating device 5224 is disposed proximal to and above the intervertebral spacer and extending between the arm segments 5222b. In use the surgeon manipulates the lever arms 5226 thereby causing the arm segments 5222b to move away from each other and thereby release the intervertebral spacer 4800. In particular embodiments, a lateral segment 5225 extends between a plurality of pairs of lever arms 5226 and the manipulation of the lever arms 5226 causes the manipulation device lateral segment 5225 to urge the arm segments 5222b outwardly.

In further embodiments, the clinician or other medical personnel also can manipulate the manipulation device 5224 to detach the manipulation device from the frame. In this way, the intervertebral spacer 4800 can be inserted through the frame interior and secured in place when the manipulation device 5224 is thereafter inserted and secured to the frame.

Such an arrangement provides sufficient gripping area and force to hold the intervertebral spacer 4800 to the frame at least during formation of the channel and but allows the clinician to relatively easily open up the arms segments 5222b to release the intervertebral spacer. Also, as the arms segments 5222b and the manipulation device 52224 are removably attached or secured to the frame, a clinician can select arm segments and manipulations devices that are appropriate sized for locating a spacer in the intervertebral space for a given target site and a patient's particular physiology.

In further embodiments, the methods of the present invention further include securing the frame assembly 5200b to adjacent vertebral bodies 2 so that the intervertebral spacer 4800 is disposed in the distended intervertebral space. Such methods further included manipulating the lever arms 5226, for example following drilling or forming of the channel, so the intervertebral spacer 4800 remains disposed in the distended intervertebral space after the frame assembly is removed.

It should be recognized that the drilling apparatus, methods and systems of the present invention can be used anteriorally or posteriorally and so that the drill bit of such systems or apparatuses can penetrate or enter the vertebral body through the pedicles.

In addition to securing one or both ends of an arcuate rod or implant device in an vertebrae 2 it also is contemplated and thus within the scope of the present invention to secure the arcuate rod within a spacer that is disposed between adjacent vertebrae. Such securing can be done as an alternative to securing one or both ends of the implant device or in addition to such securing of the ends.

Figure 31:
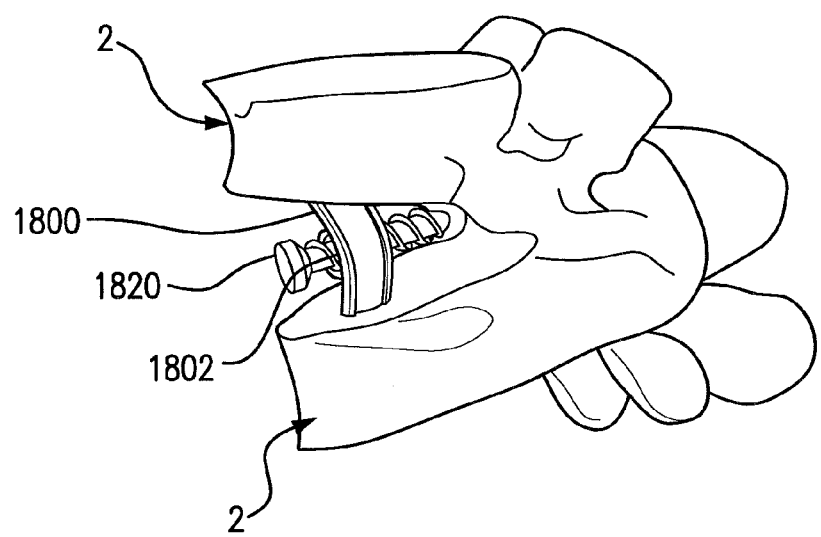
FIG. 31 is an illustrative view of adjacent vertebral bodies illustrating an implanted arcuate rod or implant device and pining member to secure an intervetebral spacer or cage (not shown) to and between the adjacent vertebral bodies.

Additionally, and referring now also to FIG. 31, an arcuate rod or implant device 1800 is additionally configured to include one or more receiving apertures 1802 that is/are located so as to be positioned between the adjacent vertebral bodies 2 when the arcuate rod or implant device is disposed in the adjacent vertebral bodies. The one or more receiving apertures 1802 also are arranged to receive therein a pining member 1820 and also so as to engage the pining member so as to thereby secure the pining member relatively to the arcuate member 1800. Such mechanically engaging includes, but is not limited to threaded connections, snap-fit type of connections or any other connections known to those skilled in the art and otherwise appropriate for the intended use.

In use, after the arcuate member or implant device 1800 is disposed in the adjacent vertebral bodies and the intervertebral spacer 4800 is disposed in the intervertebral space, the pining member 1820 is inserted through the intervertebral spacer and secured to the arcuate member or implant device. It is contemplated and thus within the scope of the present invention to provide or form a preformed aperture in the intervertebral spacer 4800 through which the pining member 1820 passes. In this way, the pining member 1820 in combination with the arcuate rod or implant device 1800 secures the intervetebral spacer 4800 between, and to, the adjacent vertebral bodies 2. Although the foregoing refers to an intervetebral spacer, it is within the scope of the present invention, for the pining member 1820 and arcuate rod or implant device 1800 to be used with any of a number of cages, spacers or other devices known to those in the art or hereinafter developed that is/are disposed between adjacent vertebral bodies 2.

Figure 30A:
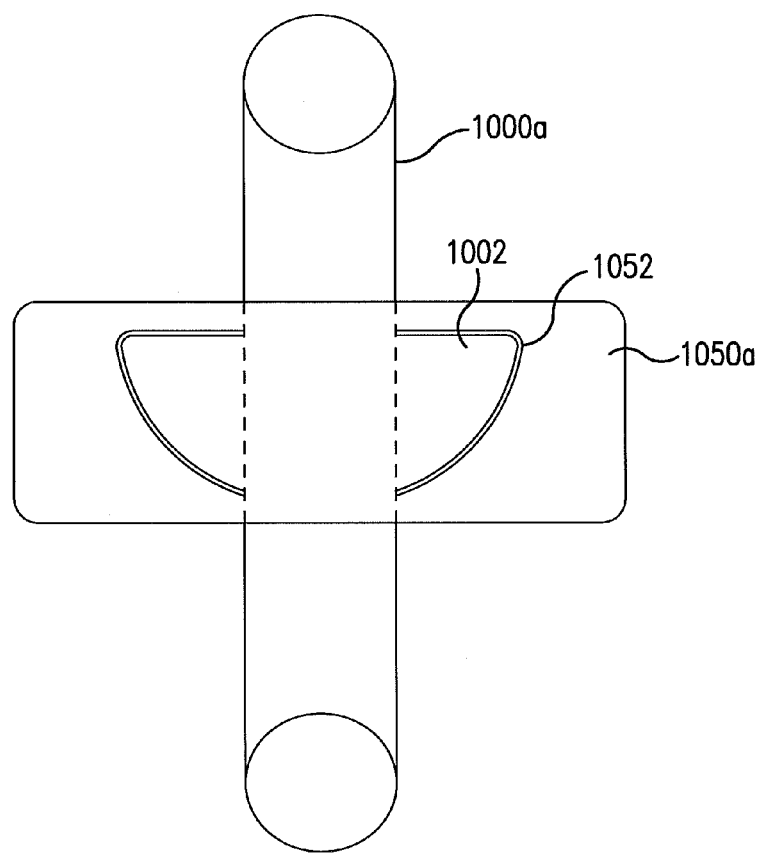
FIGS. 30A-C are views of various illustrative embodiments of securing an arcuate rod or implant device within a spacer.

Referring now to FIG. 30A, there is shown one illustrative embodiment in which an arcuate rod or implant device 1000a that is configured so as to include one or more re-positional elements or wings 1002 and a spacer 1050a including one or more recesses or pockets 1052 that is configured to receive each of the one or more wings 1002 therein. The implant device 1002 also is configured such that the wings 1002 are moveably disposed within the implant device such that the wings do not generally extend beyond the outer circumference of the implant device thereby allowing the implant device to be inserted into the arcuate passages formed in the adjacent vertebrae. The wings 1002 and the implant device also are configured such that when the wings are disposed within the pocket(s) 1052 in the spacer 1050a, the wings extend outwardly from the implant device and into the pocket(s). In an exemplary embodiment, the wings 1002 are pivotably secured to the implant device and are acted upon by a resilient member (e.g., a spring like element) to cause the wings to be displaced outwardly. In this way the wings 1002 become secured in the pocket(s) 1052 and thereby secured within the spacer 1050a.

Figure 30B:
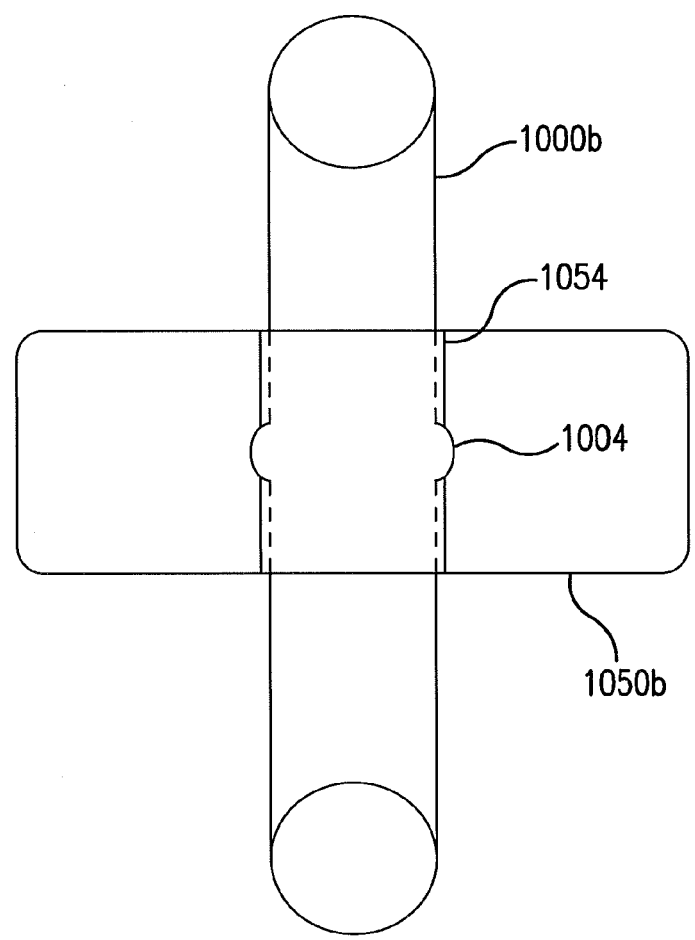

Referring now to FIG. 30B, there is shown another illustrative embodiment in which an arcuate rod or implant device 1000b that is configured so as to include one or more dimples, bumps 1004 or other surface artifacts and a spacer 1050b including one or more recesses or pockets 1052. In particular embodiments, the implant devices 1000b includes a plurality or 3 or more such bumps 1004 that are arranged about the circumference of the implant device. The one or more bumps 1004 also are configured and arranged so that the bumps are in interference fit with the inner wall 154 of the passage through the spacer 1050b. In alternative embodiments, the inner wall 154 further includes one or more depressions in the inner wall in which are received a bump 1004.

Figure 30C:
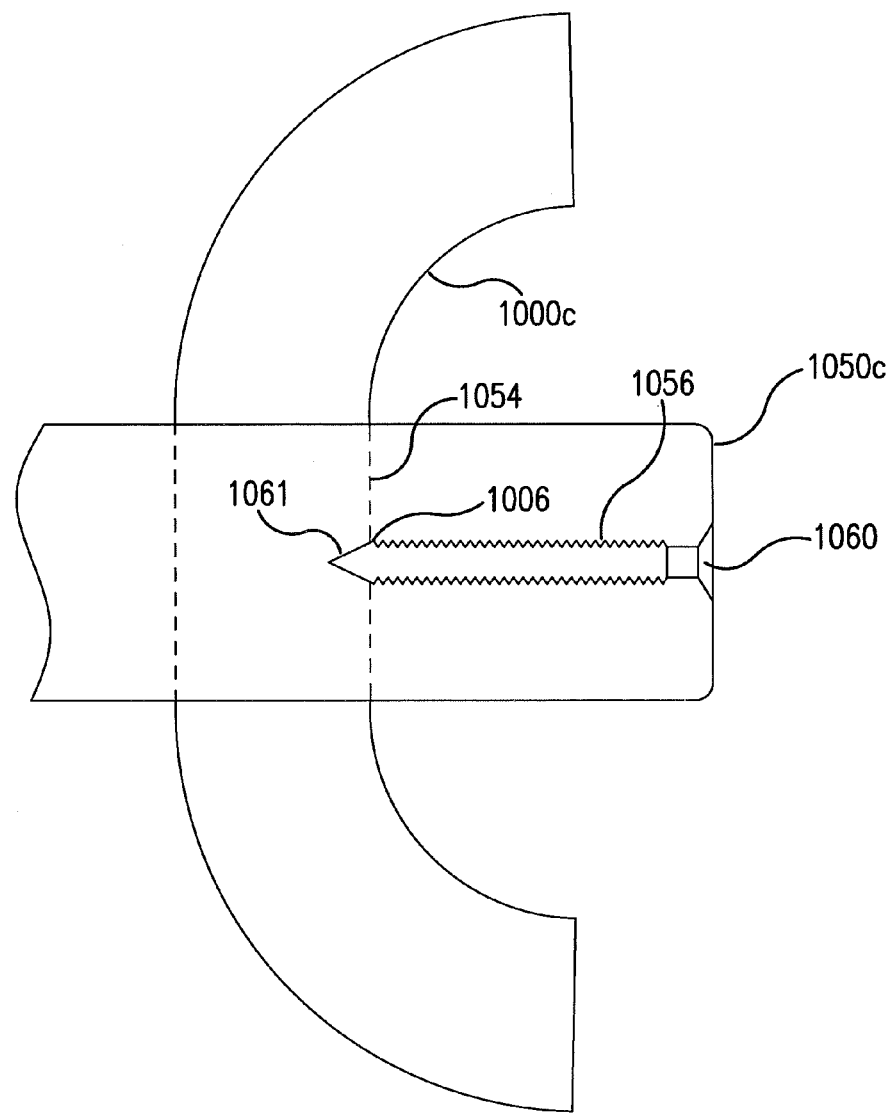

Referring now to FIG. 30C there is shown another illustrative embodiment in which an arcuate rod or implant device 1000c is secured within a spacer 1050c by means of a screw or other device. In use, after the implant device 1000c is positioned within the spacer and adjacent vertebrae, the clinician would screw the screw 1060 through the spacer such that at least the tip 1061 or a portion proximal the tip is received in the implant device. In particular embodiments, the spacer 1050c includes a passage 1056 extending from the exterior to the inner wall 1054 of the spacer, the passage can be threaded to receive the screw 1060 or be a smooth bore. In further particular embodiments, the implant device includes an opening or depression 1006 in which is received the tip 1061. Although a screw with a pointed tip is illustrated, this is not limiting as other types of screws or bolts are contemplated for use with the spacer 1050c and implant device 1000c.

Figure 32A:
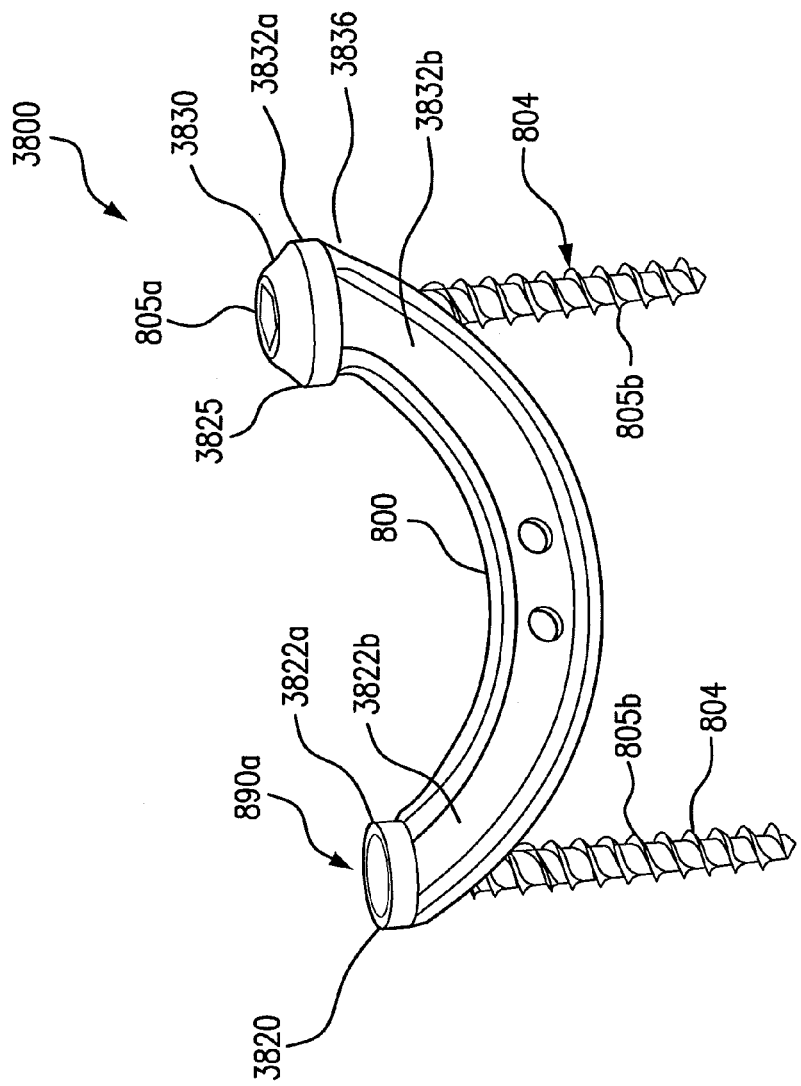
FIGS. 32A,B are various illustrative views of an arcuate rod or implant device, cap and screw assembly according to one illustrative embodiment of the present invention, where the arcuate rod or implant device is shown in cross-section.
Figure 32B:
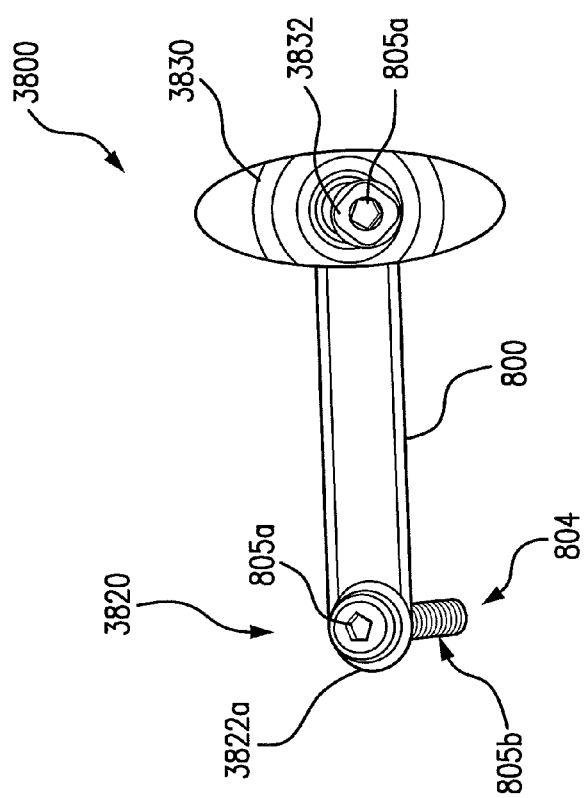
FIG. 32C is an illustrative view of an arcuate rod or implant device, cap and screw assembly according to another illustrative embodiment of the present invention, where the arcuate rod or implant device is shown in cross-section.

Referring now to FIGS. 32A-B there are shown various views of an arcuate rod or implant device, cap and screw assembly 3800 according to one illustrative embodiment of the present invention, where the arcuate rod or implant device 800 is shown in cross-section. Reference also should be made to the foregoing discussion regarding FIGS. 15-16 for features having common reference numerals (e.g., the arcuate rod or implant device 800 and the screw 804). In the illustrated embodiment, a cap member 3820, 3830 is provided at each end of the arcuate rod or implant device 800, which in combination with the screw 804 secures that end and thereby the arcuate rod or implant device to a vertebral body.

Figure 32C:
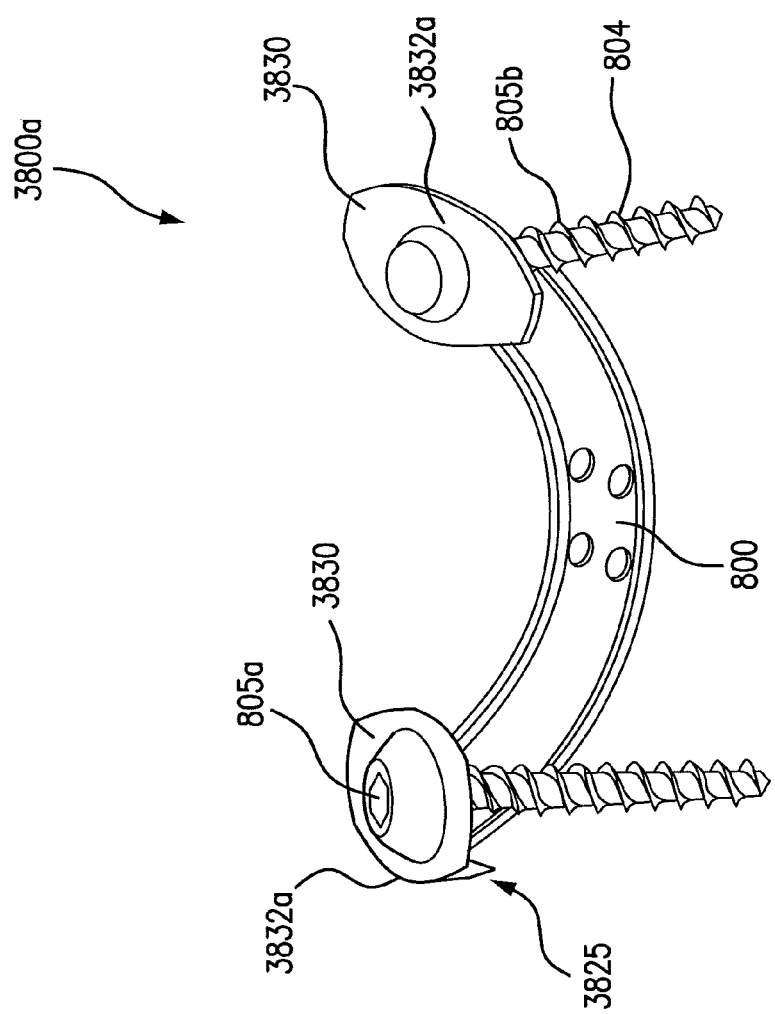

In the illustrated embodiment, two different type of cap members 3820,3830 are shown; however, this shall not be considered as a limitation. For example and as shown in FIG. 32C, an arcuate rod or implant device, cap and screw assembly 3800a according to another embodiment is arranged so the same type of cap member 3830 is provided at each end of the arcuate rod or implant device 800. Thus, it is contemplated and within the scope of the present invention for different type cap members or the same type of cap member to be provided at each end of the arcuate rod or implant device 800.

Figure 33A:
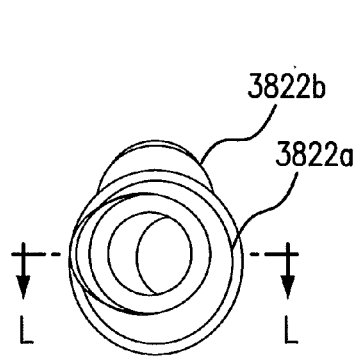
FIGS. 33A-D are top, bottom and side views respectively of one illustrative embodiment of a cap according to the present invention.
Figure 33B:
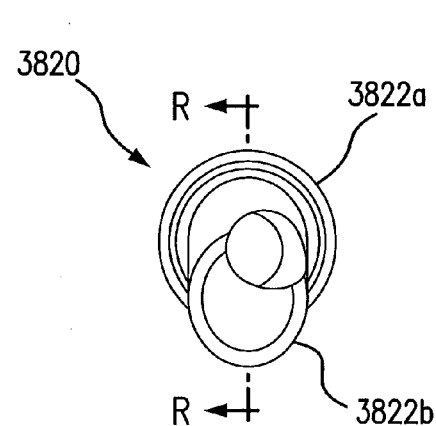
Figure 33C:
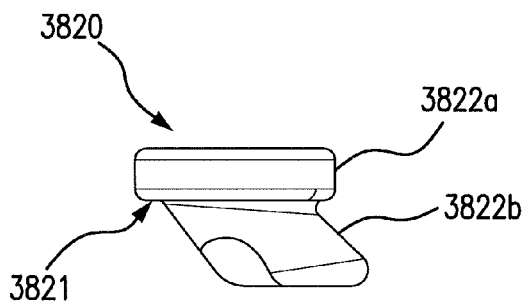
Figure 33D:
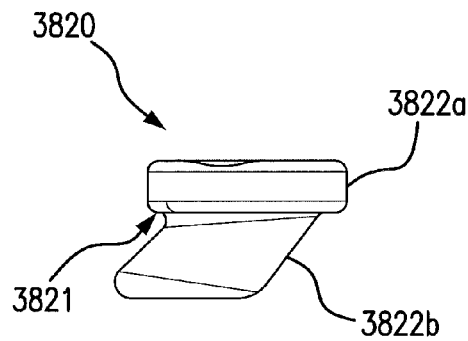
Figure 33E:
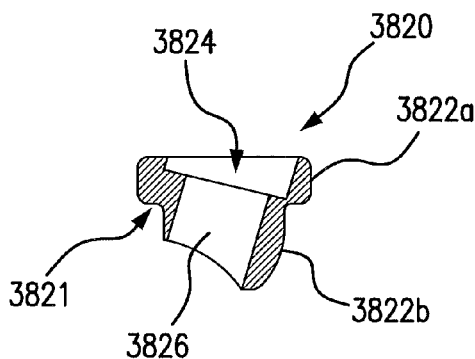
FIG. 33E is a cross-section view along section L-L of FIG. 33A.
Figure 33F:
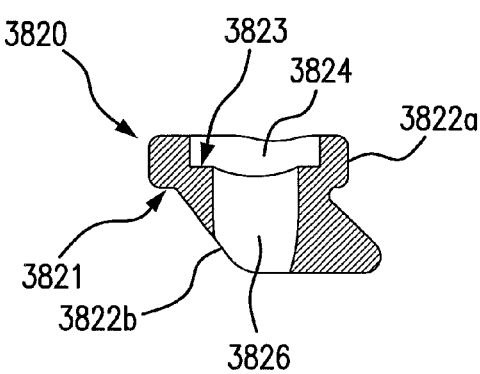
FIG. 33F is a cross-section view along section R-R of FIG. 33B.

Referring now to FIGS. 33A-F, there is shown one of the illustrated cap members, cap member 3820, The cap number 3820 includes an upper portion 3822a and a lower portion 3822b which is secured to, or formed with, the upper portion so as to extend along an arcuate path from the first portion. This arcuate path is such that the curvature of the lower potion essentially matches that of the arcuate rod or implant device 800 so that the lower portion can be received in the lumen of the arcuate rod or implant device. As shown in FIGS. 33C-D, the lower portion 3822b also is curved to match the left or right hand direction of the arcuate rod or implant device. Inparticular embodiments the lower portion 3822b is sized so as to limit or substantially prevent lateral movement of the lower portion in then lumen.

The upper portion 3822a is generally sized and arranged so as to form a flange like structure 3821 that extends outwardly so the flange like structure at least rests upon the end of the arcuate rod or implant device 800. In further embodiments, the radius of the flange like structure 3821 such that the upper portion does not generally extend beyond the region defined by the end of the arcuate rod or implant device.

The upper portion 3822a includes a stepped through aperture 3824 that is coupled to and communicates with a through aperture 3826 provided in the lower portion 3824b. The stepped through aperture 3824 and lower portion through aperture 3826 are arranged so the threaded portion 805b of the screw 804 extends downwardly and in a direction that allows the threaded portion to exit from the arcuate rod or implant device 800 and thereby be secured to the vertebral body 2 (e.g., such as that shown in FIG. 24C). The stepped through aperture 3824 also is formed so that the head 805a of the screw 804 should contact a contact surface 3823; thus limiting the motion of the screw. In further embodiments, the stepped through aperture 3824 including the contact surface 3823 are arranged so as to compliment the shape of the head 805a of the screw 804. For example, the stepped through aperture and contact surface form a dished shaped structure such as that illustrated in FIG. 34D.

Referring now to FIGS. 34A-G, there is shown another illustrated cap members 3830. The cap member 3830 includes an upper portion 3832a and a lower portion 3832b that is secured to, or formed with, the upper portion so as to extend along an arcuate path from the first portion. See also the discussion above reguarding the lower portion of 3822b for further details.

The upper portion 3832a includes a flange like structure 3831 and a raised section 3833 that extends outwardly from a surface of the flange like structure. The flange like structure 3831 is generally sized and arranged so it extends outwardly so at least a portion of the flange like structure extends beyond the end of the arcuate rod or implant device 800 and extends over, and thus adjoins or rests upon, a surface of the vertebral body (such as for example that illustrated in FIGS. 35A,B). In further embodiments, the flange like structure 3831 forms an elliptical shape, whose long or major axis is arranged so as to be at a predetermined angle with respect to the arcuate rod or implant device. The predetermined angle is such that the portion of the flange like structure along the long or major axis of the elliptical structure is positioned so the one or more downwardly extending spikes 3838 are in a desired location with respect to the vertebral body 2. In exemplary embodiments the flange like structure 3831 is arranged so the major or long axis is substantially perpendicular to the arcuate rod or implant device 800.

The raised section 3833 of the upper portion 3832a is generally arranged to receive the screw 804, in particular the head 805a thereof. The upper portion 3832a including the raised portion 3833 and the flange like structure are arranged so as to include a stepped through aperture 3834 that is coupled to and communicates with a through aperture 3836 provided in the lower portion 3832b. The stepped through aperture 3834 and lower portion through aperture 3832b are arranged so the threaded portion 805b of the screw 804 extends downwardly and in a direction that allows the threaded portion to exit from the arcuate rod or implant device 800 and thereby be secured to the vertebral body 2 (e.g., such as that shown in FIG. 24C). The stepped through aperture 3834 also is formed so that the head 805a of the screw 804 should contact a contact surface 3833; thus limiting the motion of the screw. In further embodiments, the stepped through aperture 3834 including the contact surface 3833 are arranged so as to compliment the shape of the head 805a of the screw 804. For example, the stepped through aperture and contact surface can form a dished shaped structure such as that illustrated in FIG. 34D.

As indicated above, one or more spikes 3838 extend downwardly from the flange like structure 3831 from a surface there of that opposes the vertebral body 2. The spikes 3838 are sized and arranged so as to engage at least the hard bony structure of the vertebral body 2 (e.g., cortical bone of the vertebral body). In this way, the engagement of the spikes 3838 with the cortical bone also fixes the rod with respect to the vertebrae. In more particular embodiments, a plurality of spikes extend downwardly. In exemplary embodiments, four spikes extend downwardly from the flange like structure, the spikes being arranged so that there are two spikes along each of the ends of the flange like structure and spaced from each other such as shown in FIG. 34B.

Although the spikes 3038 are illustrated as cylinders with a pointed end, this is not limiting as the spikes may comprise any other structure known in the art that provides a similar effect or funtion. Without being bound by any particular theory, the above described cap member 3820, 3830 when secured to the vertebral body 2 as described above is expected to create a structure that prevents the screw 804 from rotating or creating a windshield wiper effect within the cancellous bone of a vertebral body 2.

Figure 35A:
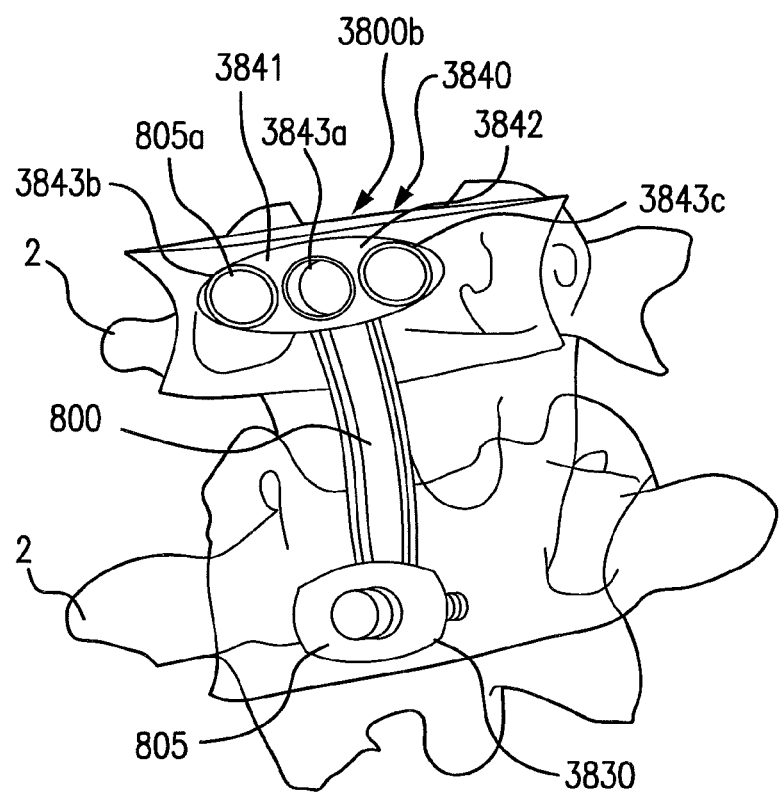
FIGS. 35A-B are various illustrative axonometric views of adjacent vertebral bodies illustrating yet an arcuate rod or implant device, cap and screw assembly according to yet another illustrative embodiment of the present invention, where the arcuate rod or implant device is shown in cross-section.
Figure 35B:
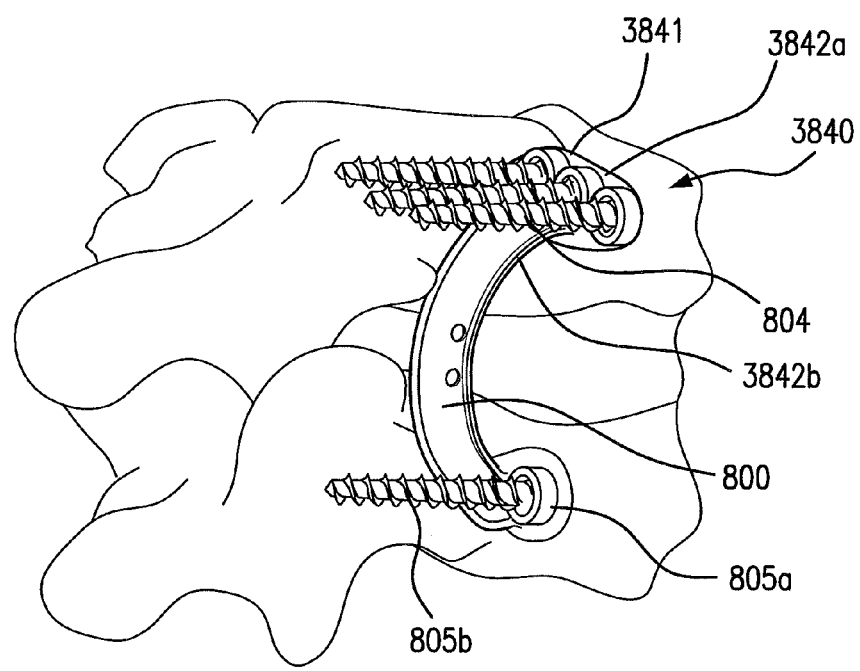

Referring now to FIGS. 35A-B there is shown various illustrative axonometric views of adjacent vertebral bodies 2 that illustrates yet another arcuate rod or implant device, cap and screw assembly 3800b according to yet another illustrative embodiment of the present invention, where the arcuate rod or implant device is shown in cross-section. The arcuate rod or implant device, cap and screw assembly 3800b according to this embodiment includes a cap member 3840 which is provided at one end of the arcuate rod or implant device 800, although it is within the scope of the present invention for such a cap member to be provided at both ends of the arcuate rod or implant device.

Such a cap member 3840 includes an upper portion 3842a and a lower portion 3842b. The upper portion 3842a includes a flange like structure 3831 and a plurality of raised sections 3843a-c that extend outwardly from a surface of the flange like structure. The flange like structure 3841 extends substantially in one direction at an angle with respect to the arcuate rod or implant device 800.

The raise sections 3843a-c are arranged on the flange like structure so that a first raised section 3843a, the flange like structure 3841 and the lower portion 3842b cooperate as described above in regards to the discussion for FIGS. 34A-G so that a screw 804 passes therethrough and through the arcuate rod or implant device. Thus, reference shall be made to the foregoing discussion of FIGS. 34A-G for further details.

Each of the other of the plurality of raised sections 3843b,c and the flange like structure 3841 are configured so as to provide a stepped through aperture to receive a screw 804 therein. Reference shall be made to the foregoing discussion for FIGS. 34A-G as to the details of such a stepped through aperture. Also, each of the other of the plurality of raise sections 3843a,b are spaced from the first raised section 3843. In particular embodiments, these other raised sections 3843b,c are laterally disposed with respect to, and on opposite sides of, the first raised section 3843a. In use, a screw 804 is passed through the stepped aperture in each of these other raised sections 3843b,c and is screwed into the vertebral body 2 until the head 805a of the screw 804 contacts the contact surface of the stepped through aperture. In this way, each of these laterally disposed screws as well as the screw passing through and secured to the first raised section 3843a thereby further fixates the cap member 3840 and thus the arcuate rod and implant device 800 to the vertebral body.

Although a preferred embodiment of the invention has been described using specific terms, such description is for illustrative purposes only, and it is to be understood that changes and variations may be made without departing from the spirit or scope of the following claims.

It should be clear that the methods, systems, and devices of the invention are not limited to securing a pair of vertebrae, but rather any combination of multiple vertebrae segments. It also should be clear that the methods, systems, and devices of the present invention are in no way limited to vertebrae segments. In particular, the invention enables securing any solid substrates, particularly bone substrates, without use of protruding screws or plates. It also should be understood that the invention is applicable to a wide variety of fixation configurations, including bone-to-bone with a gap; bone-to-bone without a gap; bone-to-bone with bony spacers; and bone-to-bone with a non-bony spacer such as a metal, polymer, or a biodegradable material.

INCORPORATION BY REFERENCE

All patents, published patent applications, US patent application and other references disclosed herein are hereby expressly incorporated by reference in their entireties by reference.

EQUIVALENTS

Those skilled in the art will recognize, or be able to ascertain using no more than routine experimentation, many equivalents of the specific embodiments of the invention described herein. Such equivalents are intended to be encompassed by the following claims.

What is claimed is:

1. A method for forming a channel in adjacent vertebra of a portion of a lower spine, said method comprising the steps of:
    providing a frame assembly including spacing elements at least one spacing element for each of the adjacent vertebra, where a length of each spacing element is set so that the frame assembly is in a desired orientation with respect to the adjacent vertebra;
    positioning the frame assembly proximal the treatment or surgical site;
    securing the frame assembly to the adjacent vertebra;
    providing a pivot arm assembly which includes a pivot arm and a pivot pin bracket operatively coupled to the pivot arm;
    removably attaching the pivot arm assembly to the frame assembly by sliding the pivot pin bracket into the frame assembly for engagement with the frame assembly; and
    operatively coupling a drill bit to the pivot arm and rotating the pivot arm and drill bit about a pivot point in fixed relation to the frame assembly to form the channel in the surface or sub-surface of the vertebra.

2. The method of claim 1, wherein said securing further includes mechanically engaging a securing mechanism to the frame assembly and to the adjacent vertebra, wherein the frame assembly is maintained in fixed relation by such mechanical engagement.

3. The method of claim 2, wherein the frame assembly is maintained in fixed relation by such mechanical engagement and lateral stiffness of the securing mechanism.

4. The method of claim 2, wherein each of the plurality of frame assembly spacing elements further include a plurality of through apertures, each through aperture including a constricted portion and a plurality of securing members and wherein said securing further includes:
    driving each of the plurality of securing members through the through apertures and the constricted portion and into the vertebra at the site, whereby the frame assembly is secured in fixed relation to the vertebra by the engagement of the constricted portion with the securing member.

5. The method of claim 4, wherein the frame assembly is secured in fixed relation by the lateral stiffness of the securing members.

6. The method of claim 1, further comprising:
    providing a drill assembly including a drill bit;
    attaching the drill assembly to the frame assembly so the drill bit follows a predetermined path in fixed relation with respect to the frame assembly; and
    moving the drill bit through the predetermined path while the drill bit is rotating thereby cutting the channel with the drill bit.

7. The method of claim 1, further comprising the step of determining if the movement of the drill bit in a first direction formed one of a complete channel or a partial channel and in the case where it is determined that a partial channel was formed, detaching and re-attaching the drill bit so as to be moveable in a second direction that is different from the first direction and moving the drill bit in the second direction.

8. The method of claim 1, further comprising the step of determining if the rotation of the pivot arm in a first direction formed one of a complete channel or a partial channel and in the case where it is determined that a partial channel was formed, detaching and re-attaching the pivot arm so as to be rotatable in a second direction that is different from the first direction and rotating the pivot arm in the second direction.

9. The method of claim 1, further comprising the step of: locating an implant in the channel.

10. The method of claim 9, further comprising the step of: attaching the implant within the channel to the vertebra, wherein said attaching includes securing the implant to the vertebra using one or more securing devices.

11. The method of claim 1, wherein one of the adjacent vertebra is a lumbar vertebrae and the other of the adjacent vertebra is the sacrum.

12. The method of claim 11, wherein said providing includes setting the length of one of the plurality of spacing elements so the frame assembly is spaced from the sacrum and is in a desired orientation with respect to the sacrum and the one of the lumbar vertebrae.

13. The method of claim 11, wherein said one of the lumbar vertebrae is the L-5 lumbar vertebrae.

14. The method of claim 1, wherein said providing includes adjusting a contacting surface of each of the plurality of spacing elements so as to complement the surface of the adjacent vertebra opposing the contact surface and so the frame assembly is in a desired orientation with respect to the adjacent vertebra.

15. The method of claim 14, wherein one of the adjacent vertebra is a lumbar vertebrae and the other of the adjacent vertebra is the sacrum.

16. The method of claim 15, wherein said providing includes adjusting the contacting surface of one of the plurality of spacing elements so the contacting surface complements the opposing surface of the sacrum and so the frame assembly is in a desired orientation with respect to the sacrum and the one of the lumbar vertebrae.

17. The method of claim 15, wherein said one of the lumbar vertebrae is the L-5 lumbar vertebrae.

18. A method for forming a plurality of channels in a treatment or surgical site of one or more segments of a bony structure or adjacent vertebra of a spine, said method comprising the steps of:
   positioning a frame assembly proximal one location of the treatment or surgical site;
   securing the frame assembly to adjacent segments of the one or more segments of the bone or bony structure or adjacent vertebra;
   providing a pivot arm assembly which includes a pivot arm and a pivot pin bracket operatively coupled to the pivot arm;
   removably attaching the pivot arm assembly to the frame assembly by sliding the pivot pin bracket into the frame assembly for engagement with the frame assembly;
   operatively coupling a drill bit to the pivot arm and rotating the pivot arm and drill bit about a pivot point in fixed relation to the frame assembly to form one of the plurality of channels in the surface or sub-surface of the bone, bony structure or vertebra;
   repositioning the frame assembly proximal to another location of the treatment or surgical site; and
   repeating said steps of securing, removably attaching, and rotating at said another location.

19. The method of claim 18, wherein said securing further includes mechanically engaging a securing mechanism to the frame assembly and to the adjacent segments of the bone or bony structure or adjacent vertebra, wherein the frame assembly is maintained in fixed relation by such mechanical engagement.

20. The method of claim 18, wherein
   the frame assembly includes spacing elements with at least one spacing element for each of the adjacent vertebra, where a length of each spacing element is set so that the frame assembly is in a desired orientation with respect to the adjacent vertebra.

21. The method of claim 20, wherein one of the adjacent vertebra is a lumbar vertebrae and the other of the adjacent vertebra is the sacrum, and wherein said providing includes setting the length of one of the plurality of spacing elements so the frame assembly is spaced from the sacrum and is in a desired orientation with respect to the sacrum and the one of the lumbar vertebrae.

22. The method of claim 21, wherein said one of the lumbar vertebrae is the L-5 lumbar vertebrae.

23. The method of claim 20, wherein said providing includes adjusting a contacting surface of each of the plurality of spacing elements so as to complement the surface of the adjacent vertebra opposing the contact surface and so the frame assembly is in a desired orientation with respect to the adjacent vertebra.

24. The method of claim 23, wherein one of the adjacent vertebra is a lumbar vertebrae and the other of the adjacent vertebra is the sacrum, and wherein said providing includes adjusting the contacting surface of one of the plurality of spacing elements so the contacting surface complements the opposing surface of the sacrum and so the frame assembly is in a desired orientation with respect to the sacrum and the one of the lumbar vertebrae.

25. The method of claim 24, wherein said one of the lumbar vertebrae is the L-5 lumbar vertebrae.

26. The method of claim 1, wherein the pivot pin bracket has opposed spring members, and the pivot arm assembly is removably attached to the frame assembly by sliding the opposed spring members into the frame assembly for engagement with opposed inner surfaces defined by the frame assembly.

\* \* \* \* \*